(12) United States Patent
Zhang

(10) Patent No.: US 8,969,373 B2
(45) Date of Patent: Mar. 3, 2015

(54) HCV PROTEASE INHIBITORS

(75) Inventor: Suoming Zhang, Shanghai (CN)

(73) Assignee: Shanghai Tangrun Pharmaceuticals Co., Ltd., Shanghai (CN)

( * ) Notice: Subject to any disclaimer, the term of this patent is extended or adjusted under 35 U.S.C. 154(b) by 0 days.

(21) Appl. No.: 14/236,468

(22) PCT Filed: Jul. 23, 2012

(86) PCT No.: PCT/CN2012/078990
§ 371 (c)(1),
(2), (4) Date: Jan. 31, 2014

(87) PCT Pub. No.: WO2013/017026
PCT Pub. Date: Feb. 7, 2013

(65) Prior Publication Data
US 2014/0163219 A1 Jun. 12, 2014

(30) Foreign Application Priority Data
Aug. 2, 2011 (CN) .......................... 2011 1 0220053

(51) Int. Cl.
C07D 491/048 (2006.01)
C07D 495/04 (2006.01)
C07D 207/16 (2006.01)
A61K 31/4355 (2006.01)
A61K 31/4365 (2006.01)
A61K 31/437 (2006.01)
C07K 5/08 (2006.01)
C07K 5/083 (2006.01)

(52) U.S. Cl.
CPC ............ C07D 495/04 (2013.01); C07K 5/0802 (2013.01); C07K 5/0808 (2013.01); C07D 491/048 (2013.01); C07D 207/16 (2013.01)
USPC ............. 514/285; 514/291; 540/460; 546/62; 546/80; 546/89

(58) Field of Classification Search
USPC .......... 540/460; 546/62, 80, 89; 514/285, 291
See application file for complete search history.

(56) References Cited

U.S. PATENT DOCUMENTS

| | | | |
|---|---|---|---|
| 2009/0111757 A1* | 4/2009 | Lin et al. .......................... | 514/18 |
| 2009/0286814 A1* | 11/2009 | Lin et al. ........................ | 514/267 |
| 2011/0065737 A1* | 3/2011 | Liu et al. ........................ | 514/267 |
| 2011/0178107 A1* | 7/2011 | Wang et al. .................... | 514/267 |

* cited by examiner

*Primary Examiner* — Bruck Kifle
(74) *Attorney, Agent, or Firm* — Wang Law Firm, Inc.; Li K. Wang; Stephen Hsu

(57) ABSTRACT

A compound of general formula (I);

A is O, S, CH, NH or NR', when O links with $Z_3$, $Z_1$ is N or $CR_{Z1}$, $Z_2$ is $CR_{Z2}$, when $Z_1$ links with O, $Z_2$ is CH, $Z_3$ is C—Ar; Ra, Rb, Rc and Rd independently is H, OH, halogen or —$Y^1$—$R^m$; $A_1$ is NH or $CH_2$; $R_1'$ is alkyl, aryl, cycloalkyl, heterocycloalkyl or heteroaryl; $A_2$ is N, O or linking bond; $R_1$ is hydrogen, or, $R_1$ linking covalently with $R_3$ forms $C_5$-$C_9$ saturated or unsaturated hydrocarbon chain substituted by O or N; $R_3$ is alkyl, cycloalkyl, heterocycloalkyl, alkyl substituted by cycloalkyl etc; $R_4$ is alkoxy-CO, alkyl-NHCO, (alkyl)$_2$NCO, or formyl substituted by aryl, cycloalkyl, heterocycloalkyl.

19 Claims, No Drawings

HCV PROTEASE INHIBITORS

FIELD OF THE INVENTION

The invention relates to a kind of compound having anti-virus activity, more particularly to a kind of hepatitis C virus protease inhibitor.

BACKGROUND OF THE INVENTION

Viral hepatitis can be divided into seven types of A, B, C, D, E, F and G Hepatitis C is the most common one and is a kind of infectious disease targeting liver organs caused by hepatitis C virus (hepatitis C virus, HCV). About 3 percent of the global population has been infected with the hepatitis C virus.

Hepatitis C virus (HCV) is a positive-strand RNA of about 9.6 Kb including 5' untranslated region (5'-UTR), open reading frame (ORF) and 3' untranslated region (3'-UTR). ORF is translated into a polypeptide chain which is subsequently processed into at least 10 different proteins including one nucleocapsid protein, two envelope proteins (E1 and E2) and non-structural proteins (NS2, NS3, NS4A, NS4B, NS5A and NS5B).

At present, there are about 17 anti-HCV compounds (such as ABT-450, BMS-650032, BI 201335, TMC-435, GS 9256, ACH-1625, MK-7009, etc) which have been into the stage of the pre-clinical and clinical development. All of them are designed to target HCV NS3/4A serine protease inhibitors. For example, the drug boceprevir developed by the pharmaceutical giant Merck (Merck) and the drug telaprevir developed by Vertex Pharmaceuticals, Inc. (Vertex), both are designed to target NS3/4A serine protease of HCV, which were approved by U.S. FDA in 2011. Showed clinically is that the cure rate of both drugs combined with standard treatment can be increased to approximately 75%.

Nevertheless, these drugs are just the beginning. Researchers are developing drugs targeting to more than one biological characteristic of hepatitis C virus. These drugs by combined administration are expected to solve the drug-resistant problem of HCV.

SUMMARY OF THE INVENTION

The first aim of the present invention is to provide an anti-virus compound having the general formula (I), or a pharmaceutically acceptable prodrug, salt or hydrate thereof,

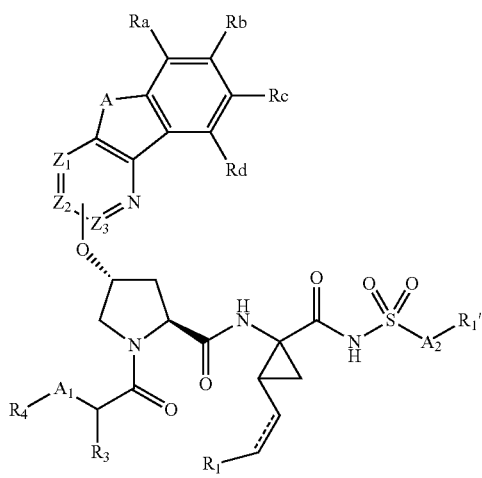

(I)

wherein,

A is O, S, CH, NH or NR', wherein, R' is $C_1$-$C_6$ alkyl substituted or unsubstituted by halogen which includes 0~3 heteroatom(s) of O, S or N.

Ra, Rb, Rc and Rd independently is H, OH, halogen or —$Y^1$—$R^m$, $Y^1$ is linking bond, O, S, SO, $SO_2$ or NR"; $R^m$ is hydrogen, or, $R^m$ is an unsubstituted substituent or one substituted by 1~3 $R^{m'}$ which is selected from the following group: ($C_1$-$C_8$) alkyl, N≡C—($C_1$-$C_6$) alkyl, ($C_2$-$C_8$) alkenyl, ($C_2$-$C_8$) alkynyl, ($C_3$-$C_7$) cycloalkyl, ($C_3$-$C_7$ cycloalkyl) ($C_1$-$C_6$) alkyl, and 5~6 membered aryl or heteroaryl including 0~2 heteroatom(s) independently selected from N, O, S;

R" is H, ($C_1$-$C_6$) alkyl or ($C_3$-$C_6$) cycloalkyl. Wherein, $R^{m'}$ is a substituent selected from the following group: halogen, ($C_1$-$C_6$) alkyl substituted optionally by ($C_1$-$C_6$)alkyl-O— or ($C_3$-$C_6$)cycloalkyl-O—, ($C_1$-$C_6$) haloalkyl, ($C_3$-$C_7$)cycloalkyl, ($C_1$-$C_6$)alkyl-O—, heteroaryl, —$NH_2$, ($C_1$-$C_4$ alkyl)NH— and ($C_1$-$C_4$ alkyl)$_2$N—.

$A_1$ is NH or $CH_2$.

$A_2$ is N, O or linking bond.

$R_1'$ is an unsubstituted substituent or one substituted by 1 to more $R_1"$ which is selected from the following group: $C_1$-$C_6$ alkyl, $C_2$-$C_6$ alkenyl, $C_2$-$C_6$ alkynyl, aryl, (aryl) $C_1$-$C_2$ alkyl, $C_3$-$C_7$ cycloalkyl, ($C_3$-$C_7$ cycloalkyl) $C_1$-$C_2$ alkyl, $C_3$-$C_7$ cycloalkenyl, ($C_3$-$C_7$ cycloalkenyl) $C_1$-$C_2$ alkyl, heterocycloalkyl, (heterocycloalkyl) $C_1$-$C_2$ alkyl, $C_5$-$C_{10}$ heteroaryl and ($C_5$-$C_{10}$ heteroaryl) $C_1$-$C_2$ alkyl;

$R_1"$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$;

preferably, $R_1'$ is

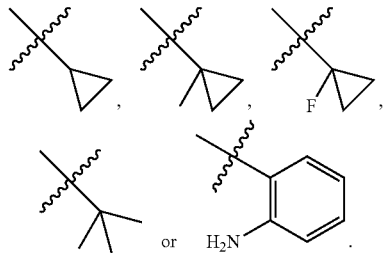

$R_1$ is hydrogen; or; $R_1$ linking covalently with $R_3$ together forms a $C_5$-$C_9$ saturated or unsaturated hydrocarbon chain which can be inserted by 0~2 heteroatom(s) independently selected from N, S and O, or which can be substituted by none or more halogen, O, S or —$NR_pR_q$, wherein, $R_p$ and $R_q$ independently is hydrogen or $C_1$-$C_6$ alkyl; preferably, $R_1$ linking covalently with $R_3$ together forms a $C_5$ alkane chain.

$R_3$ is $C_1$-$C_6$ alkyl, $C_2$-$C_6$ alkenyl, $C_3$-$C_7$ cycloalkyl, $C_3$-$C_7$ cycloalkenyl, heterocycloalkyl, ($C_3$-$C_7$ cycloalkyl) $C_1$-$C_4$ alkyl, ($C_3$-$C_7$ cycloalkenyl) $C_1$-$C_4$ alkyl, (heterocycloalkyl) $C_1$-$C_4$ alkyl, $C_2$-$C_6$ alkylacyl, ($C_1$-$C_4$ alkyl)$_{1-2}$ ($C_3$-$C_7$) cycloalkyl or ($C_1$-$C_6$ alkyl)$_{1-2}$ amino.

$R_4$ is $C_1$-$C_{10}$ alkoxycarbonyl, ($C_1$-$C_{10}$ alkyl)-NHCO, ($C_1$-$C_{10}$ alkyl)$_2$NCO, aryl, heteroaryl or formyl substituted by 3~7 membered cycloalkyl, heterocycloalkyl or cycloalkoxy, which may be unsubstituted or substituted by 1 to more $R_4'$; wherein, $R_4'$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$, ($C_1$-$C_6$ alkyl)-$SO_2$—;

preferably, $R_4$ is

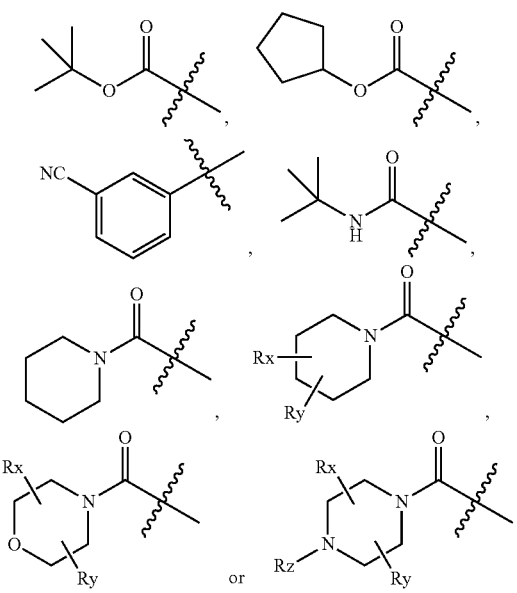

wherein, Rx and Ry independently is F, Cl, $C_1$-$C_6$ alkyl or $C_1$-$C_6$ alkoxyl, Rz is $C_1$-$C_6$ alkyl, $C_1$-$C_6$ alkoxyl, $C_1$-$C_6$ alkylformyl or ($C_1$-$C_6$ alkyl)-$SO_2$—.

When $Z_3$ links with O, $Z_1$ is N or $CR_{Z1}$, $Z_2$ is $CR_{Z2}$, wherein, $R_{Z1}$ is hydrogen, halogen, $C_1$-$C_6$ alkyl, $C_1$-$C_6$ alkoxy, $NH_2$, ($C_1$-$C_6$ alkyl)NH or ($C_1$-$C_6$ alkyl)$_2$N, $R_{Z2}$ is hydrogen, $C_1$-$C_6$ alkyl, $C_1$-$C_6$ alkoxy, aryl or heteroaryl; or $R_{Z1}$, $R_{Z2}$ with carbon atoms linking with them together form a substituted or unsubstituted ring;

when $Z_1$ links with O, $Z_2$ is CH, $Z_3$ is C—Ar, Ar is a substituted or unsubstituted aryl or heteroaryl.

In one preferable embodiment of the present invention, when $Z_3$ links with O, preferably, $R_{Z1}$, $R_{Z2}$ with carbon atoms linking with them together form a 6 membered aromatic ring substituted by Re, Rf, Rg and Rh, shown in formula (Ia), (Ia)

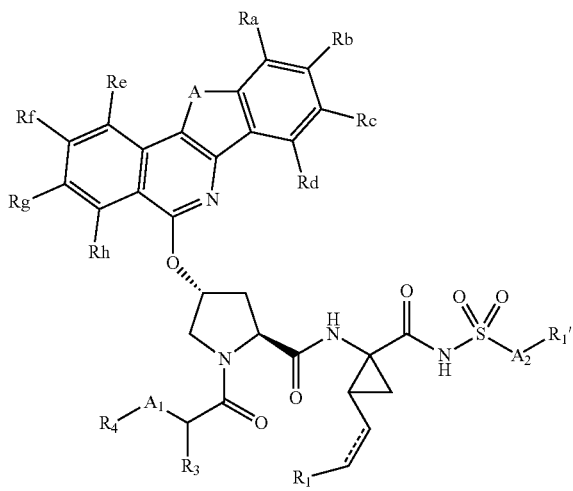

In formula (Ia),

A is O, S, CH, NH or NR', wherein, R' is $C_1$-$C_6$ alkyl substituted or unsubstituted by halogen which includes 0~3 heteroatom(s) of O, S or N.

Ra, Rb, Rc, Rd, Re, Rf, Rg and Rh independently is H, OH, halogen or —$Y^1$—$R'''$, $Y^1$ is linking bond, O, S, SO, $SO_2$ or NR''; R''' is hydrogen, or, R''' is an unsubstituted substituent or one substituted by 1~3 R'''' which is selected from the following group: ($C_1$-$C_8$) alkyl, N≡C—($C_1$-$C_6$) alkyl, ($C_2$-$C_8$) alkenyl, ($C_2$-$C_8$) alkynyl, ($C_3$-$C_7$) cycloalkyl, ($C_3$-$C_7$ cycloalkyl) ($C_1$-$C_6$) alkyl, and 5~6 membered aryl or heteroaryl including 0~2 heteroatom(s) independently selected from N, O, S; R'' is H, ($C_1$-$C_6$) alkyl or ($C_3$-$C_6$) cycloalkyl. Wherein, R'''' is a substituent selected from the following group: halogen, ($C_1$-$C_6$) alkyl substituted optionally by ($C_1$-$C_6$)alkyl-O— or ($C_3$-$C_6$)cycloalkyl-O—, ($C_1$-$C_6$) haloalkyl, ($C_3$-$C_7$)cycloalkyl, ($C_1$-$C_6$)alkyl-O—, heteroaryl, —$NH_2$, ($C_1$-$C_4$ alkyl)NH— and ($C_1$-$C_4$ alkyl)$_2$N—.

$A_1$ is NH or $CH_2$.

$A_2$ is N, O or linking bond.

$R_1'$ is an unsubstituted substituent or one substituted by 1 to more $R_1''$ which is selected from the following group: $C_1$-$C_6$ alkyl, $C_2$-$C_6$ alkenyl, $C_2$-$C_6$ alkynyl, aryl, (aryl) $C_1$-$C_2$ alkyl, $C_3$-$C_7$ cycloalkyl, ($C_3$-$C_7$ cycloalkyl) $C_1$-$C_2$ alkyl, $C_3$-$C_7$ cycloalkenyl, ($C_3$-$C_7$ cycloalkenyl) $C_1$-$C_2$ alkyl, heterocycloalkyl, (heterocycloalkyl) $C_1$-$C_2$ alkyl, $C_5$-$C_{10}$ heteroaryl and ($C_5$-$C_{10}$ heteroaryl) $C_1$-$C_2$ alkyl;

$R_1''$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$;

preferably, $R_1'$ is

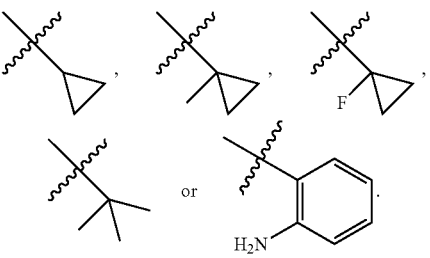

$R_1$ is hydrogen; or; $R_1$ linking covalently with $R_3$ together forms a $C_5$-$C_9$ saturated or unsaturated hydrocarbon chain which can be inserted by 0~2 heteroatom(s) independently selected from N, S and O, or which can be substituted by none or more halogen, O, S or —$NR_pR_q$, wherein, $R_p$ and $R_q$ independently is hydrogen or $C_1$-$C_6$ alkyl; preferably, $R_1$ linking covalently with $R_3$ together forms a $C_5$ alkane chain.

$R_3$ is $C_1$-$C_6$ alkyl, $C_2$-$C_6$ alkenyl, $C_3$-$C_7$ cycloalkyl, $C_3$-$C_7$ cycloalkenyl, heterocycloalkyl, ($C_3$-$C_7$ cycloalkyl) $C_1$-$C_4$ alkyl, ($C_3$-$C_7$ cycloalkenyl) $C_1$-$C_4$ alkyl, (heterocycloalkyl) $C_1$-$C_4$ alkyl, $C_2$-$C_6$ alkylacyl, ($C_1$-$C_4$ alkyl)$_{1-2}$ ($C_3$-$C_7$) cycloalkyl or ($C_1$-$C_6$ alkyl)$_{1-2}$ amino.

$R_4$ is $C_1$-$C_{10}$ alkoxycarbonyl, ($C_1$-$C_{10}$ alkyl)-NHCO, ($C_1$-$C_{10}$ alkyl)$_2$NCO, aryl, heteroaryl or formyl substituted by 3~7 membered cycloalkyl, heterocycloalkyl or cycloalkoxy, which may be unsubstituted or substituted by 1 to more $R_4'$; wherein, $R_4'$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$, ($C_1$-$C_6$ alkyl)-$SO_2$—;

preferably, R₄ is

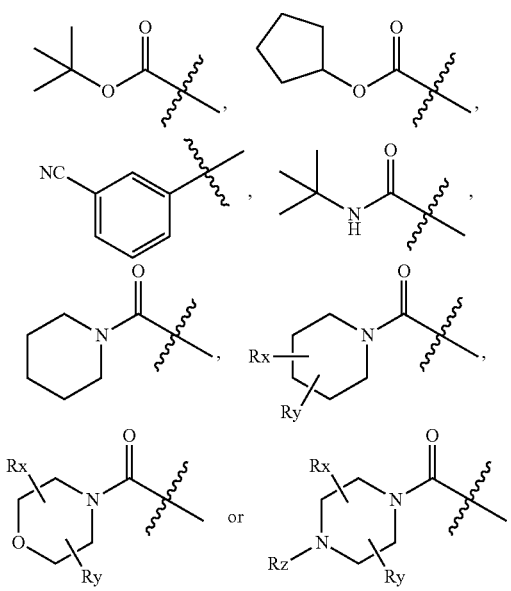

wherein, Rx and Ry independently is F, Cl, $C_1$-$C_6$ alkyl or $C_1$-$C_6$ alkoxyl, Rz is $C_1$-$C_6$ alkyl, $C_1$-$C_6$ alkoxyl, $C_1$-$C_6$ alkylformyl or ($C_1$-$C_6$ alkyl)-$SO_2$—.

In second preferably embodiment of the present invention, when $Z_1$ links with O, preferably, $R_1$ is hydrogen, $R_3$ is $C_1$-$C_6$ alkyl, $C_2$-$C_6$ alkenyl, $C_3$-$C_7$ cycloalkyl, $C_3$-$C_7$ cycloalkenyl, heterocycloalkyl, ($C_3$-$C_7$ cycloalkyl) $C_1$-$C_4$ alkyl, ($C_3$-$C_7$ cycloalkenyl) $C_1$-$C_4$ alkyl, (heterocycloalkyl) $C_1$-$C_4$ alkyl, $C_2$-$C_6$ alkylacyl, ($C_1$-$C_4$ alkyl)$_{1-2}$($C_3$-$C_7$) cycloalkyl or ($C_1$-$C_6$ alkyl)$_{1-2}$ amino. In this case, the general formula (I) turns into formula (Ib1),

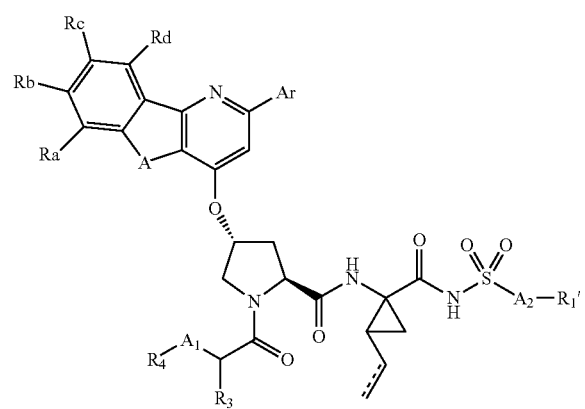

(Ib1)

In formula (Ib1),
Ar is a substituted or unsubstituted aryl or heteroaryl, preferably, Ar is a 6 membered aryl or a 5~6 membered heteroaryl which is substituted optionally by 1 or more $R_{Ar}$; wherein, $R_{Ar}$ is selected from the following substituent group: halogen, amino, $C_1$-$C_6$ alkyl, $C_1$-$C_6$ alkoxyl, $C_1$-$C_6$ hydroxyalkyl and ($C_1$-$C_6$) alkylamido.
A is O, S, CH, NH or NR', wherein, R' is $C_1$-$C_6$ alkyl substituted or unsubstituted by halogen which includes 0~3 heteroatom(s) of O, S or N.

Ra, Rb, Rc and Rd independently is H, OH, halogen or —$Y^1$—$R^{m}$, $Y^1$ is linking bond, O, S, SO, $SO_2$ or NR''; $R^{m}$ is hydrogen, or, $R^{m}$ is an unsubstituted substituent or one substituted by 1~3 $R^{m'}$ which is selected from the following group: ($C_1$-$C_8$) alkyl, N≡C—($C_1$-$C_6$) alkyl, ($C_2$-$C_8$) alkenyl, ($C_2$-$C_8$) alkynyl, ($C_3$-$C_7$) cycloalkyl, ($C_3$-$C_7$ cycloalkyl) ($C_1$-$C_6$) alkyl, and 5~6 membered aryl or heteroaryl including 0~2 heteroatom(s) independently selected from N, O, S;

R'' is H, ($C_1$-$C_6$) alkyl or ($C_3$-$C_6$) cycloalkyl. Wherein, $R^{m'}$ is a substituent selected from the following group: halogen, ($C_1$-$C_6$) alkyl substituted optionally by ($C_1$-$C_6$)alkyl-O— or ($C_3$-$C_6$)cycloalkyl-O—, ($C_1$-$C_6$) haloalkyl, ($C_3$-$C_7$)cycloalkyl, ($C_1$-$C_6$)alkyl-O—, heteroaryl, —$NH_2$, ($C_1$-$C_4$ alkyl)NH— and ($C_1$-$C_4$ alkyl)$_2$N—.

$A_1$ is NH or $CH_2$.
$A_2$ is N, O or linking bond.
$R_1'$ is an unsubstituted substituent or one substituted by 1 to more $R_1''$ which is selected from the following group: $C_1$-$C_6$ alkyl, $C_2$-$C_6$ alkenyl, $C_2$-$C_6$ alkynyl, aryl, (aryl) $C_1$-$C_2$ alkyl, $C_3$-$C_7$ cycloalkyl, ($C_3$-$C_7$ cycloalkyl) $C_1$-$C_2$ alkyl, $C_3$-$C_7$ cycloalkenyl, ($C_3$-$C_7$ cycloalkenyl) $C_1$-$C_2$ alkyl, heterocycloalkyl, (heterocycloalkyl) $C_1$-$C_2$ alkyl, $C_5$-$C_{10}$ heteroaryl and ($C_5$-$C_{10}$ heteroaryl) $C_1$-$C_2$ alkyl;

$R_1''$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$;

preferably, $R_1'$ is

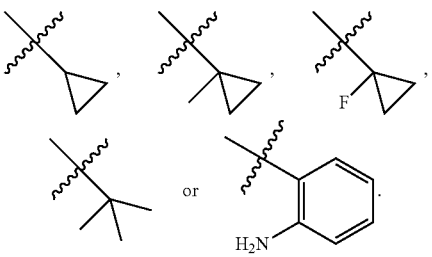

$R_4$ is $C_1$-$C_{10}$ alkoxycarbonyl, ($C_1$-$C_{10}$ alkyl)-NHCO, ($C_1$-$C_{10}$ alkyl)$_2$NCO, aryl, heteroaryl or formyl substituted by 3~7 membered cycloalkyl, heterocycloalkyl or cycloalkoxy, which may be unsubstituted or substituted by 1 to more $R_4'$; wherein, $R_4'$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$, ($C_1$-$C_6$ alkyl)-$SO_2$—;

preferably, $R_4$ is

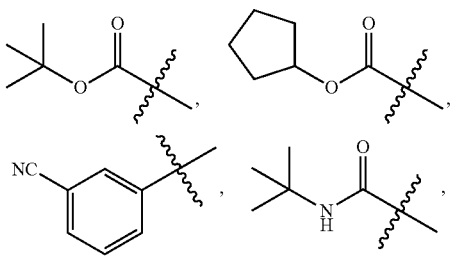

-continued

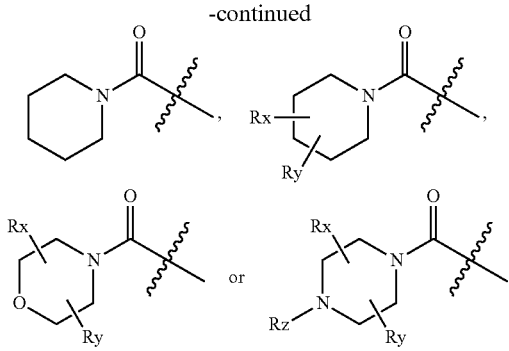

wherein, Rx and Ry independently is F, Cl, $C_1$-$C_6$ alkyl or $C_1$-$C_6$ alkoxyl, Rz is $C_1$-$C_6$ alkyl, $C_1$-$C_6$ alkoxyl, $C_1$-$C_6$ alkylformyl or ($C_1$-$C_6$ alkyl)-$SO_2$—.

In another preferably embodiment of the present invention, when $Z_1$ links with O, preferably, $R_1$ linking covalently with $R_3$ together forms a $C_5$-$C_9$ saturated or unsaturated hydrocarbon chain which can be inserted by 0~2 heteroatom(s) independently selected from N, S and O, or which can be substituted by none or more halogen, O, S or —$NR_pR_q$, wherein, $R_p$ and $R_q$ independently is hydrogen or $C_1$-$C_6$ alkyl. In this case, $A_1$ is preferably $CH_2$ and the general formula (I) turns into formula (Ib2), (Ib2)

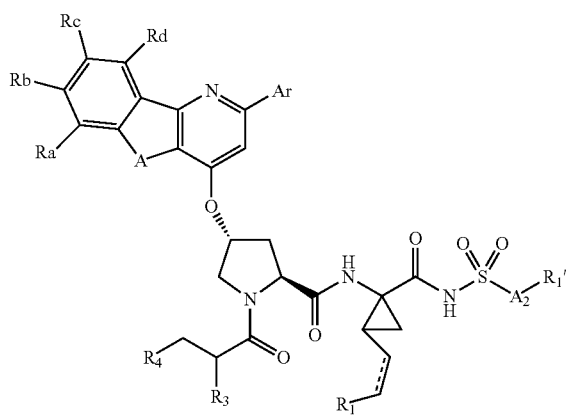

In formula (Ib2),

Ar is a substituted or unsubstituted aryl or heteroaryl, preferably, Ar is a 6 membered aryl or a 5~6 membered heteroaryl which is substituted optionally by 1 or more $R_{Ar}$; wherein, $R_{Ar}$ is selected from the following substituent group: halogen, amino, $C_1$-$C_6$ alkyl, $C_1$-$C_6$ alkoxyl, $C_1$-$C_6$ hydroxyalkyl and ($C_1$-$C_6$) alkylamido.

A is O, S, CH, NH or NR', wherein, R' is $C_1$-$C_6$ alkyl substituted or unsubstituted by halogen which includes 0~3 heteroatom(s) of O, S or N.

Ra, Rb, Rc and Rd independently is H, OH, halogen or —$Y^1$—$R'''$, $Y^1$ is linking bond, O, S, SO, $SO_2$ or NR''; $R'''$ is hydrogen, or, $R'''$ is an unsubstituted substituent or one substituted by 1~3 $R''''$ which is selected from the following group: ($C_1$-$C_8$) alkyl, N≡C—($C_1$-$C_6$) alkyl, ($C_2$-$C_8$) alkenyl, ($C_2$-$C_8$) alkynyl, ($C_3$-$C_7$) cycloalkyl, ($C_3$-$C_7$ cycloalkyl) ($C_1$-$C_6$) alkyl, and 5~6 membered aryl or heteroaryl including 0~2 heteroatom(s) independently selected from N, O, S; R'' is H, ($C_1$-$C_6$) alkyl or ($C_3$-$C_6$)

cycloalkyl. Wherein, $R'''$ is a substituent selected from the following group: halogen, ($C_1$-$C_6$) alkyl substituted optionally by ($C_1$-$C_6$)alkyl-O— or ($C_3$-$C_6$)cycloalkyl-O—, ($C_1$-$C_6$) haloalkyl, ($C_3$-$C_7$)cycloalkyl, ($C_1$-$C_6$)alkyl-O—, heteroaryl, —$NH_2$, ($C_1$-$C_4$ alkyl)NH— and ($C_1$-$C_4$ alkyl)$_2$N—.

$A_2$ is N, O or linking bond.

$R_1'$ is an unsubstituted substituent or one substituted by 1 to more $R_1''$ which is selected from the following group: $C_1$-$C_6$ alkyl, $C_2$-$C_6$ alkenyl, $C_2$-$C_6$ alkynyl, aryl, (aryl) $C_1$-$C_2$ alkyl, $C_3$-$C_7$ cycloalkyl, ($C_3$-$C_7$ cycloalkyl) $C_1$-$C_2$ alkyl, $C_3$-$C_7$ cycloalkenyl, ($C_3$-$C_7$ cycloalkenyl) $C_1$-$C_2$ alkyl, heterocycloalkyl, (heterocycloalkyl) $C_1$-$C_2$ alkyl, $C_5$-$C_{10}$ heteroaryl and ($C_5$-$C_{10}$ heteroaryl) $C_1$-$C_2$ alkyl;

$R_1''$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$;

preferably, $R_1'$ is

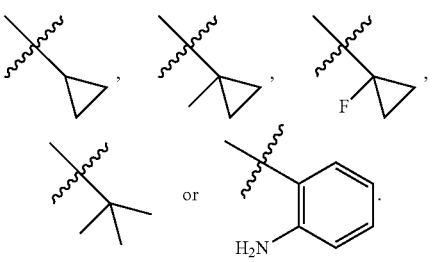

$R_4$ is $C_1$-$C_{10}$ alkoxycarbonyl, ($C_1$-$C_{10}$ alkyl)-NHCO, ($C_1$-$C_{10}$ alkyl)$_2$NCO, aryl, heteroaryl or formyl substituted by 3~7 membered cycloalkyl, heterocycloalkyl or cycloalkoxy, which may be not substituted or substituted by 1 or more $R_4'$; wherein, $R_4'$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)-NH— and —N($C_1$-$C_6$ alkyl)$_2$, ($C_1$-$C_6$ alkyl)-$SO_2$—;

preferably, $R_4$ is

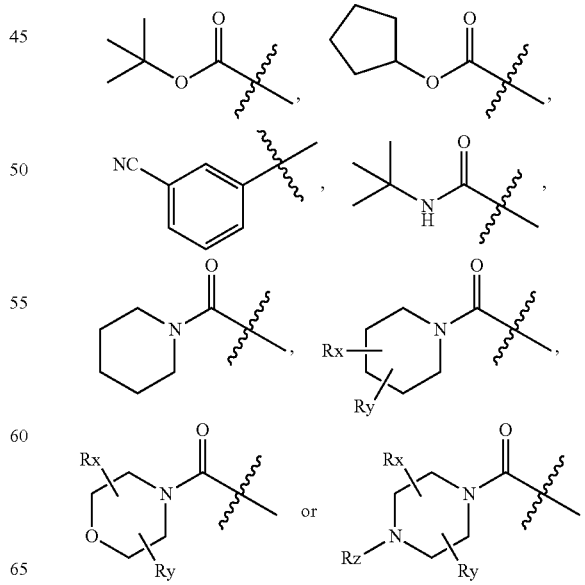

wherein, Rx and Ry independently is F, Cl, $C_1$-$C_6$ alkyl or $C_1$-$C_6$ alkoxyl, Rz is $C_1$-$C_6$ alkyl, $C_1$-$C_6$ alkoxyl, $C_1$-$C_6$ alkylformyl or ($C_1$-$C_6$ alkyl)-$SO_2$—.
In the present invention, ═══ means that it can be double bond or single bond either.
In the present invention, the detailed compound is preferably as follows:
I1
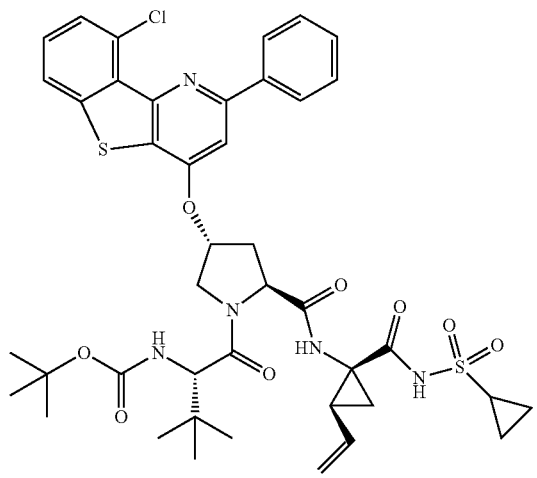
I2
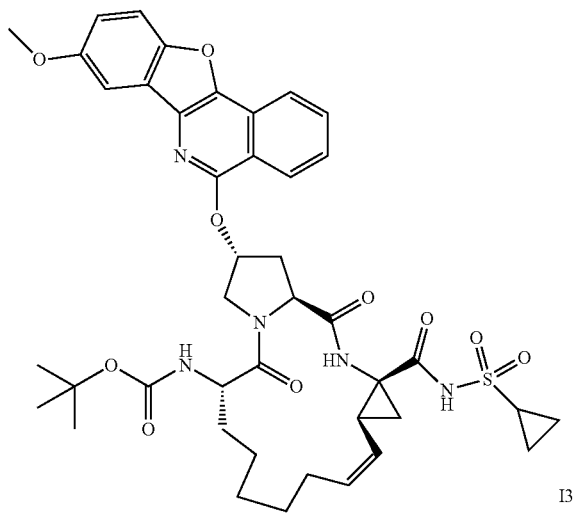
I3
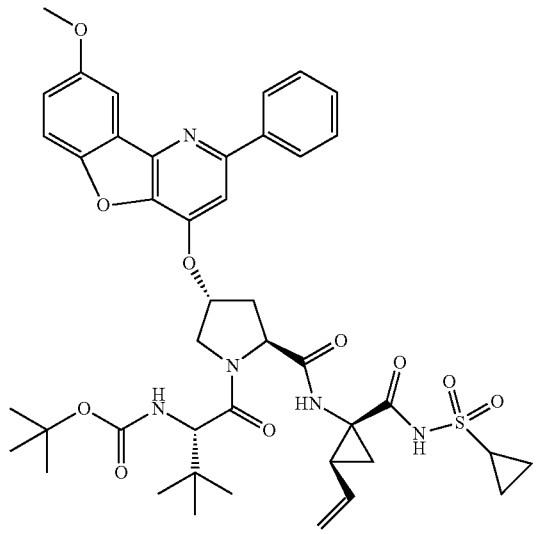
I4
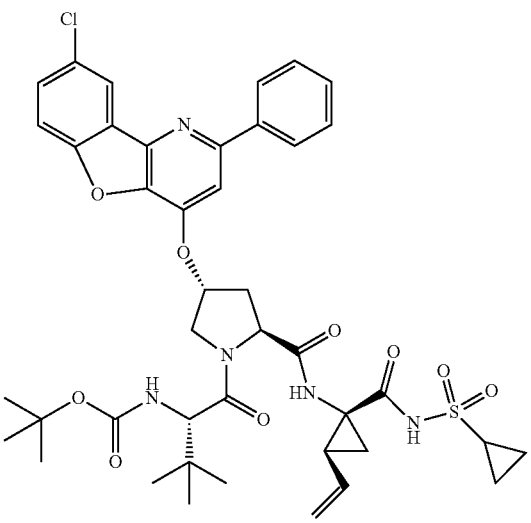
I5
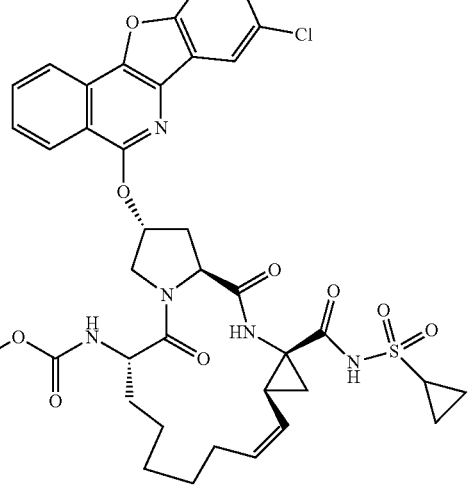
I6
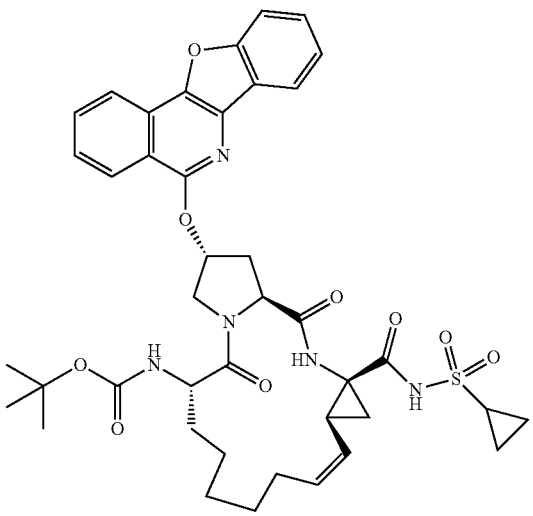

I7
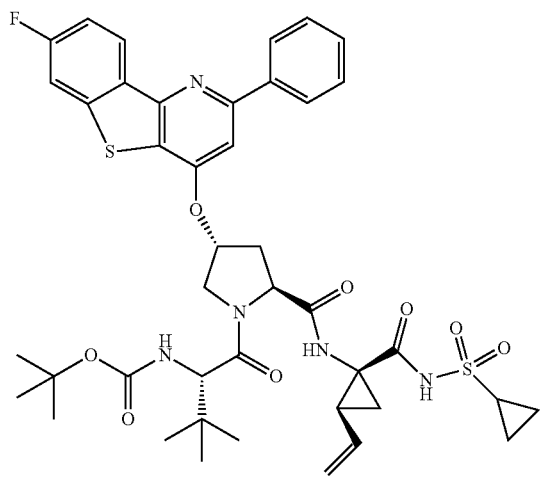
I8
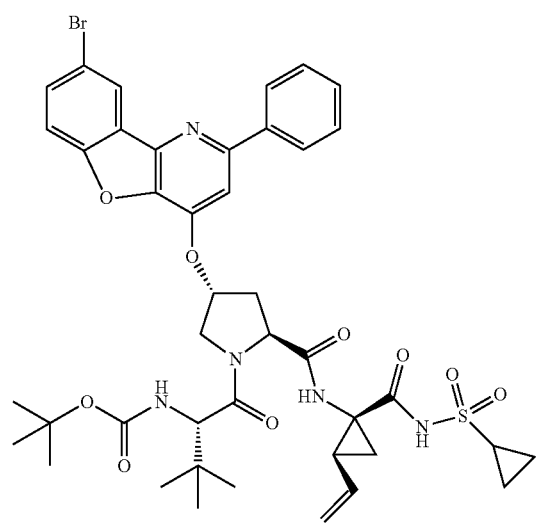
I10
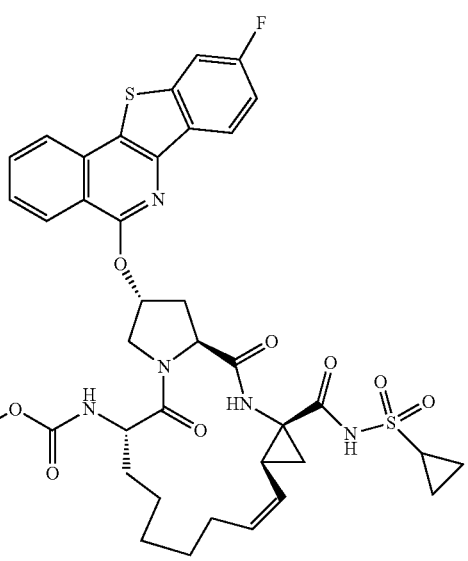
I11
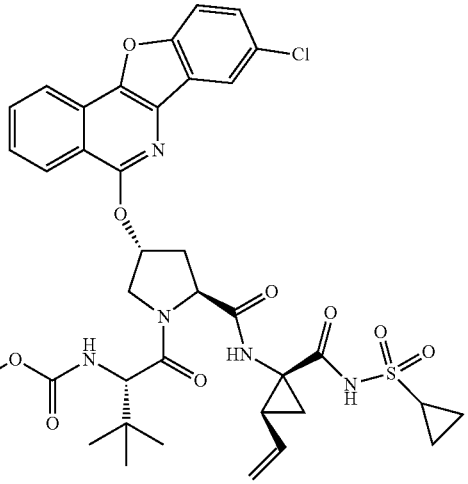
I12
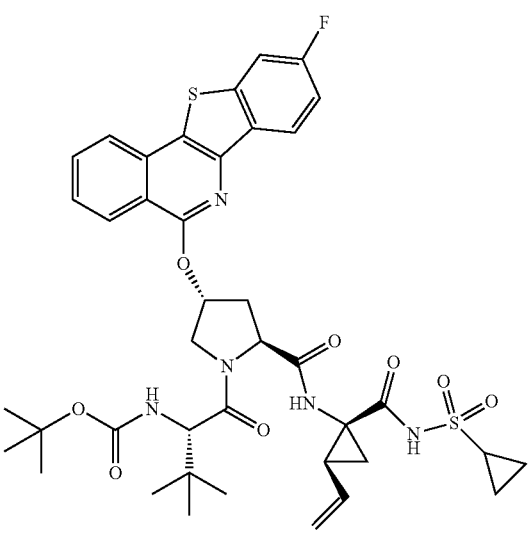

I13
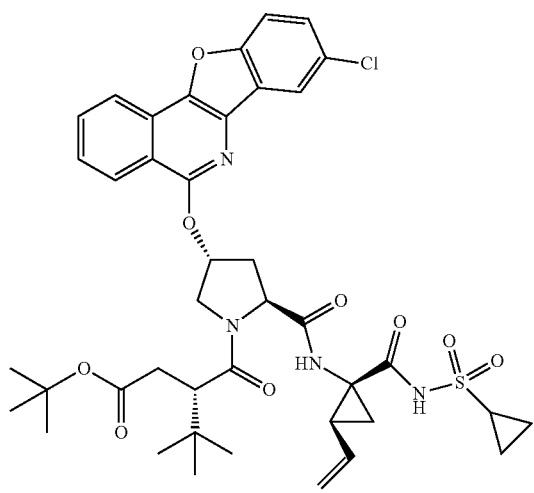
I14
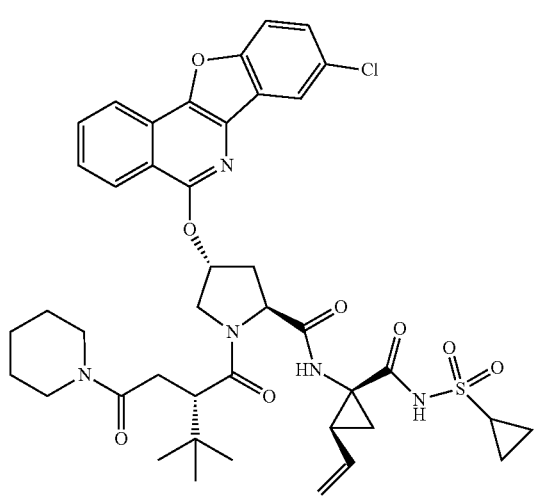
I15
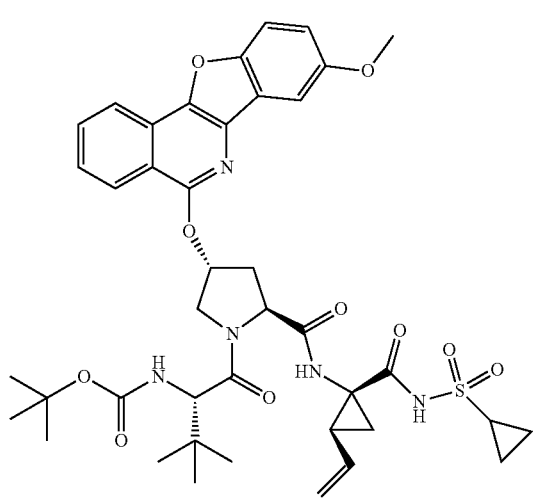
I16
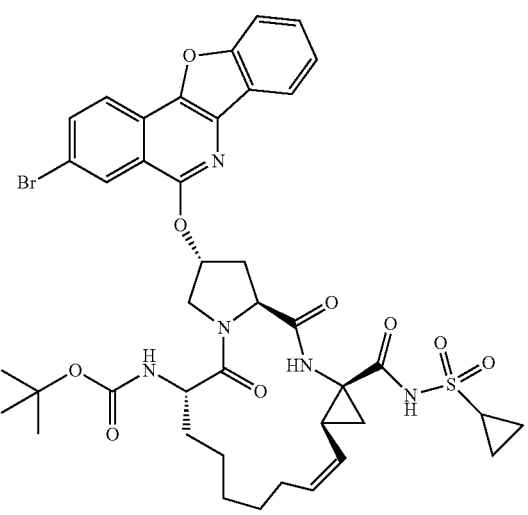
I17
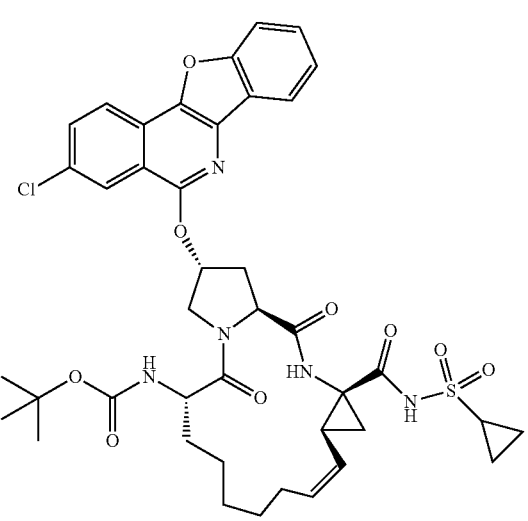
I18
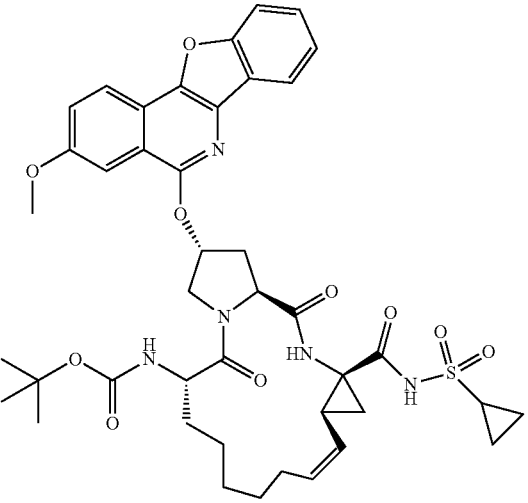

I19
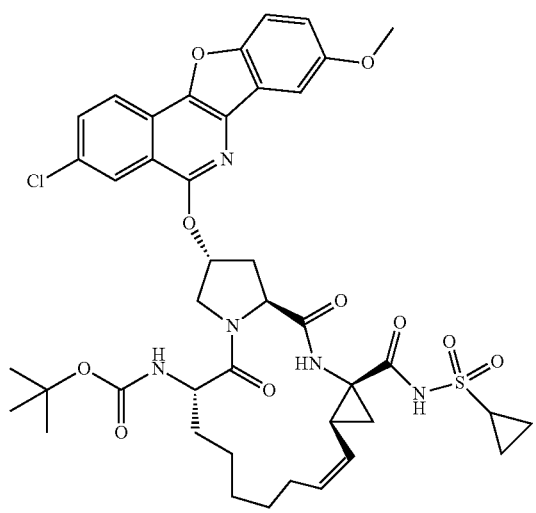
I22
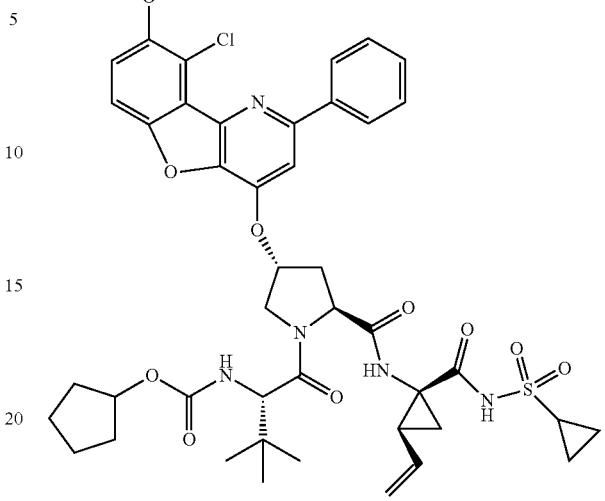
I20
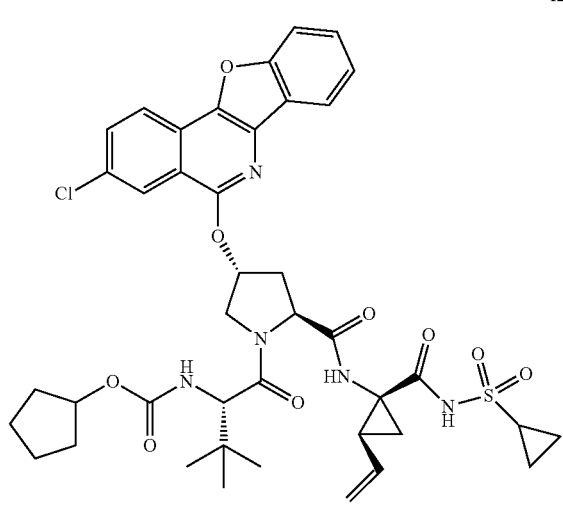
I23
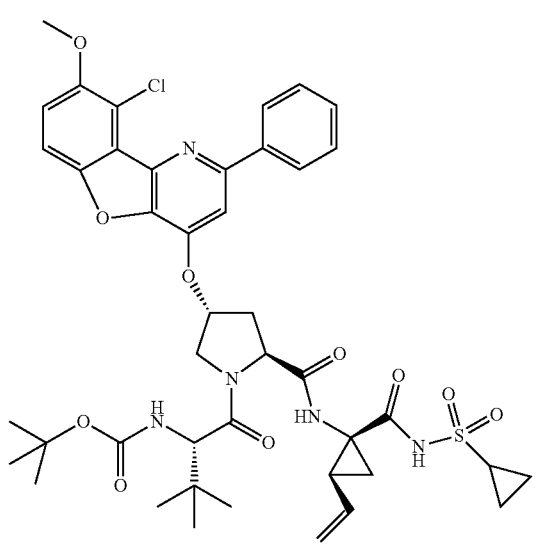
I21
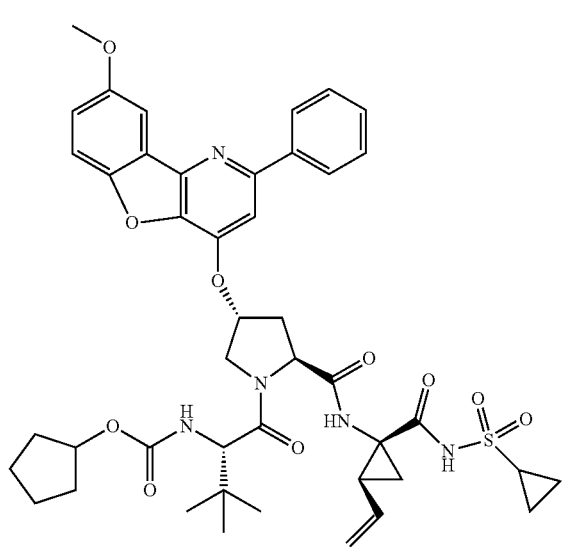
I24
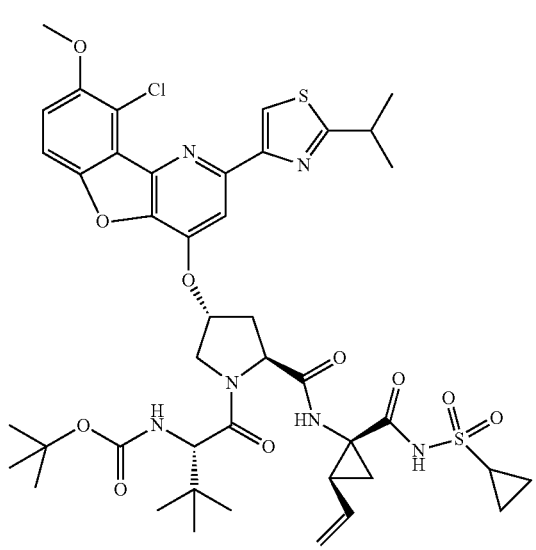

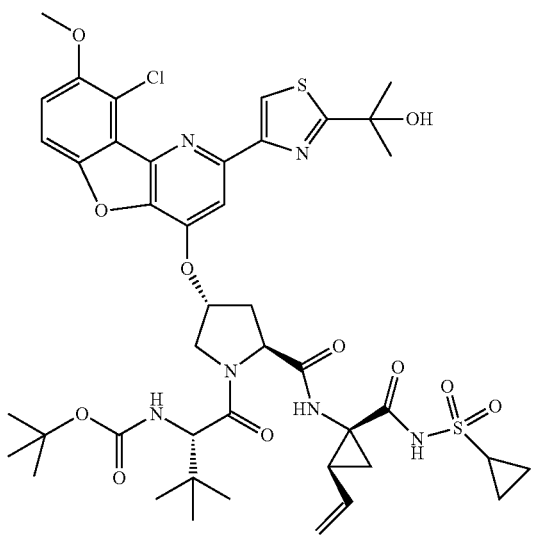
I25
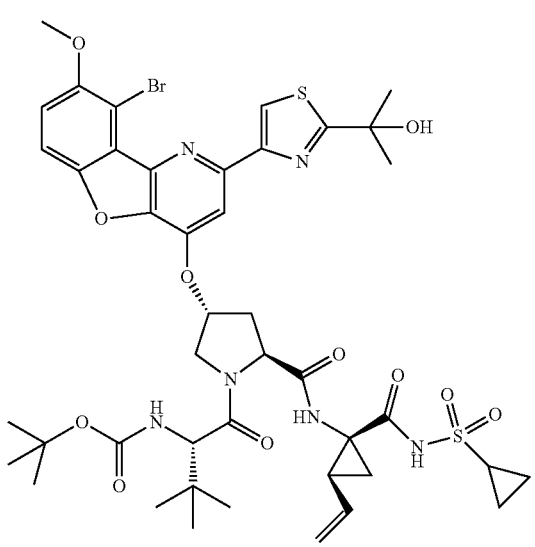
I26
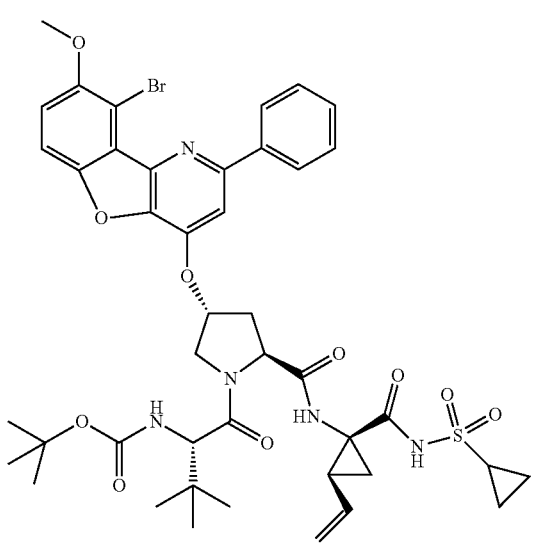
I27
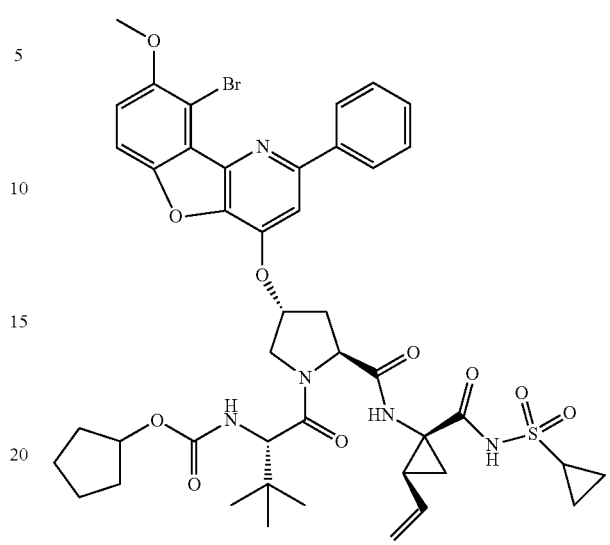
I28
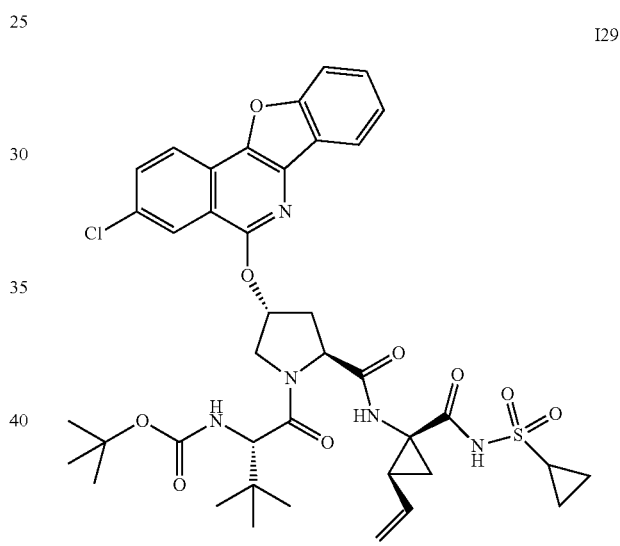
I29
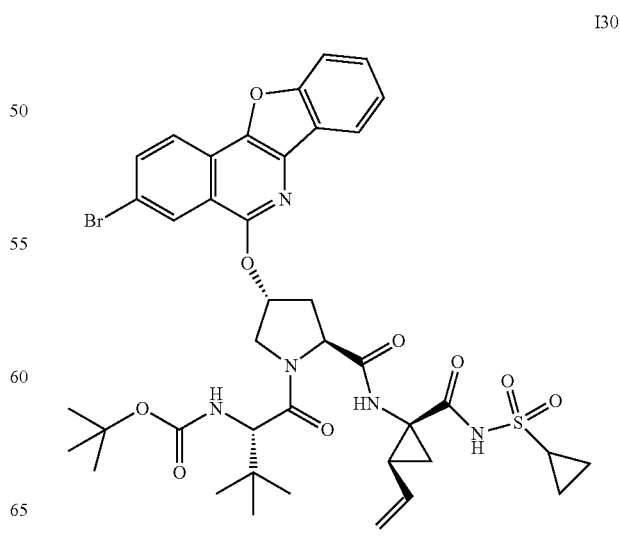
I30

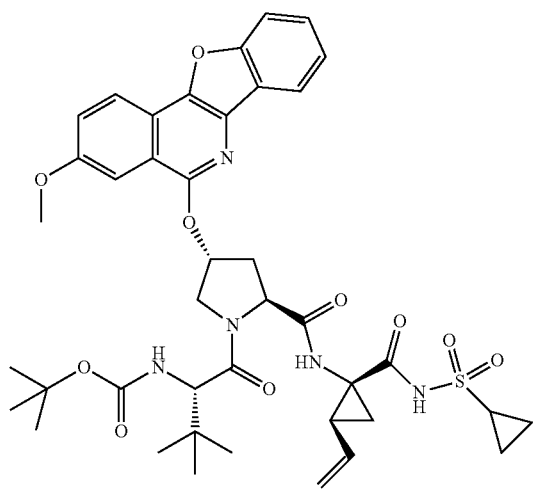
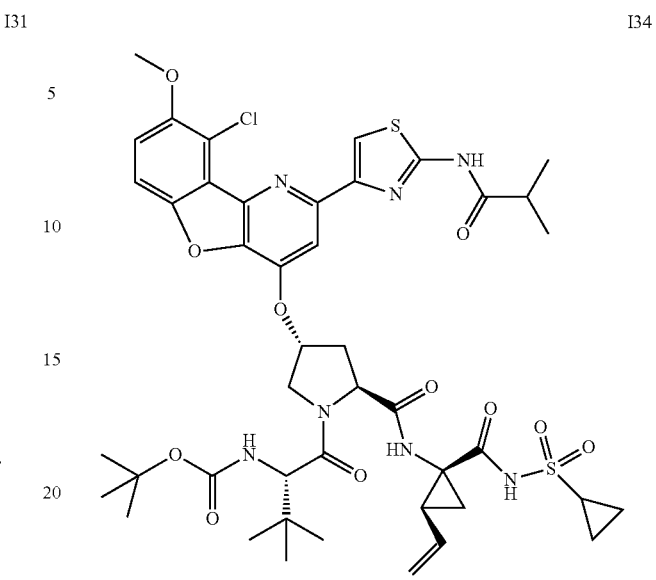

-continued
I37
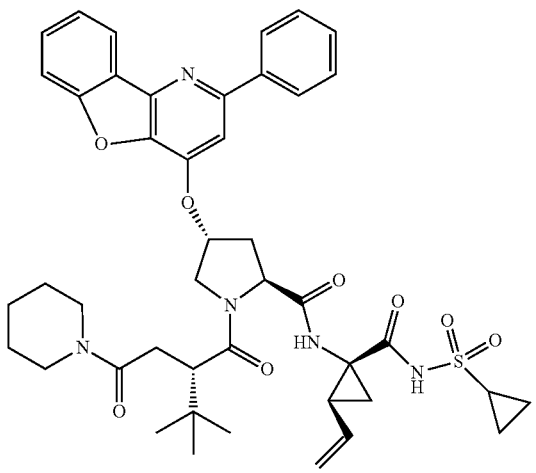
I38
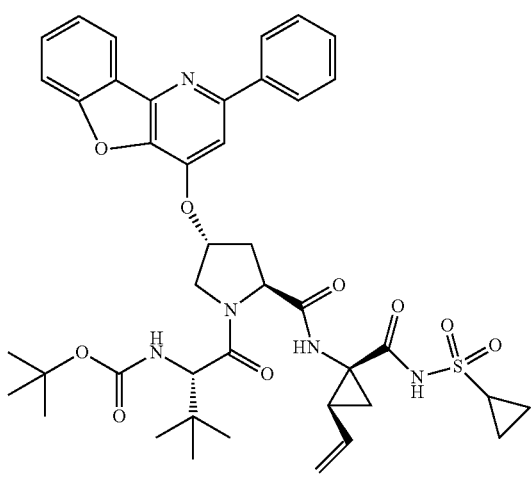
I39
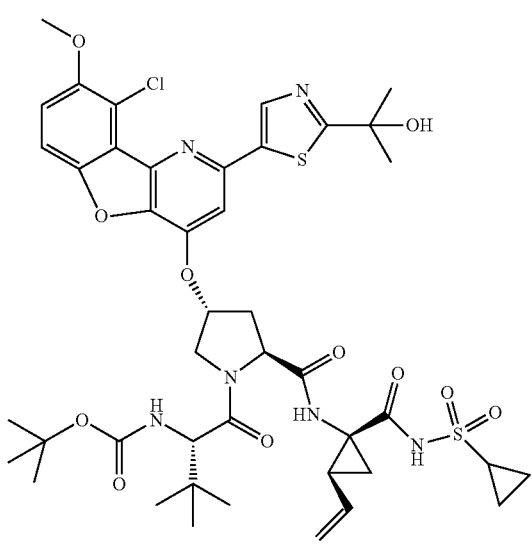
-continued
I40
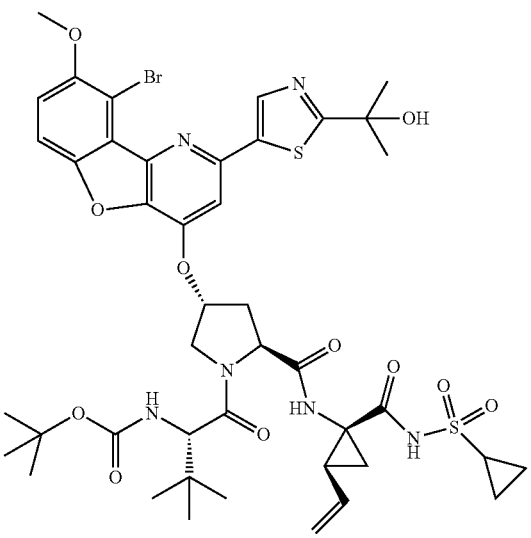
I41
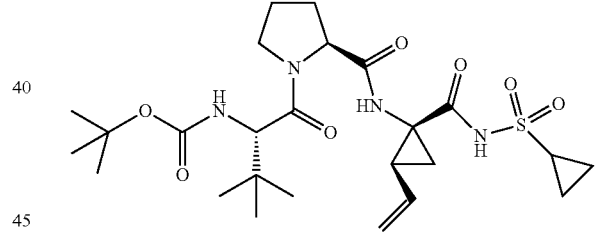
I42
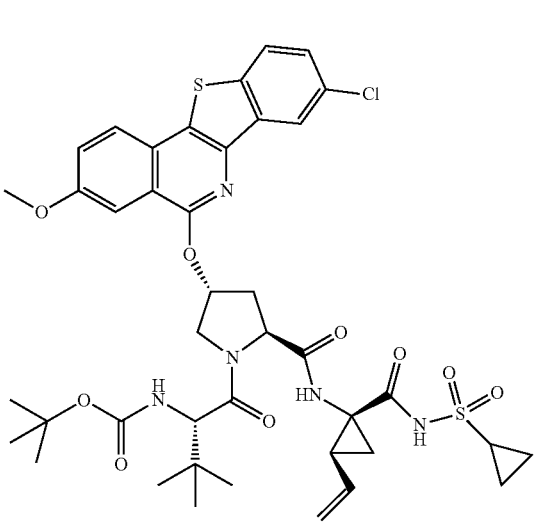

The second aim of the present invention is to provide a pharmaceutical composition that comprises the compound having the general formula (I) of the present invention and pharmaceutically acceptable carrier(s). Wherein, the pharmaceutical composition of the present invention can also be used in combination with other anti-virus drugs such as interferon or ribavirin.

The third aim of the present invention is to provide a use of the compound of the present invention in preparation of a drug for preventing virus infection or antivirus, wherein, said virus is preferably hepatitis virus, more preferably hepatitis C virus.

The forth aim of the present invention is to provide a method where an effective amount of the compound of the present invention is administered to a patient infected with hepatitis virus, more preferably with HCV.

The synthesis process of the compound having the formula (I) of the present invention is as follows:

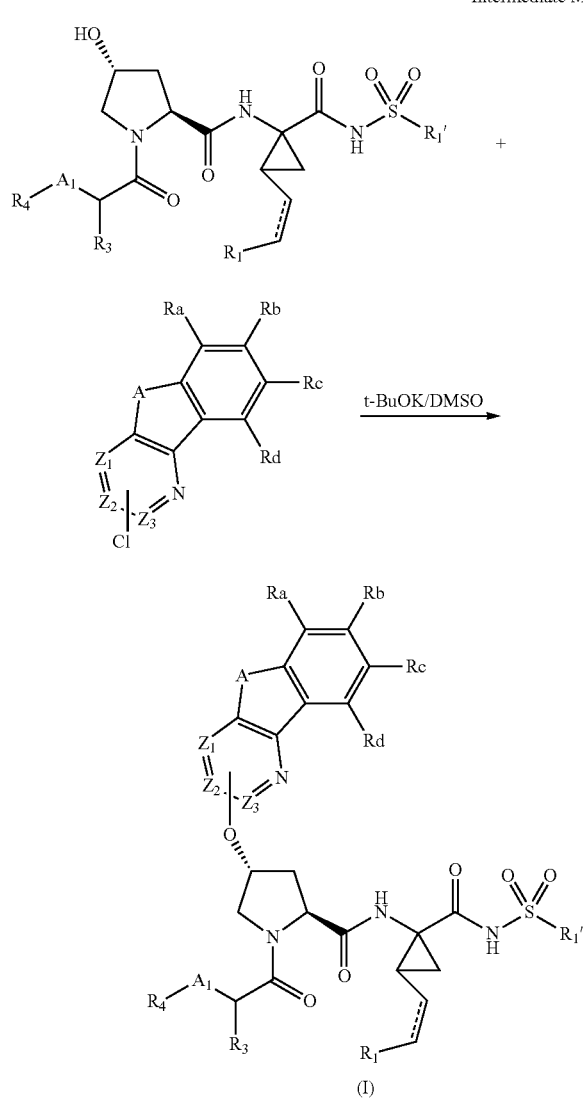

Specifically, when $Z_3$ links with O, the synthesis of intermediate M that used to synthesize the compound having the formula (Ia) is as follows:

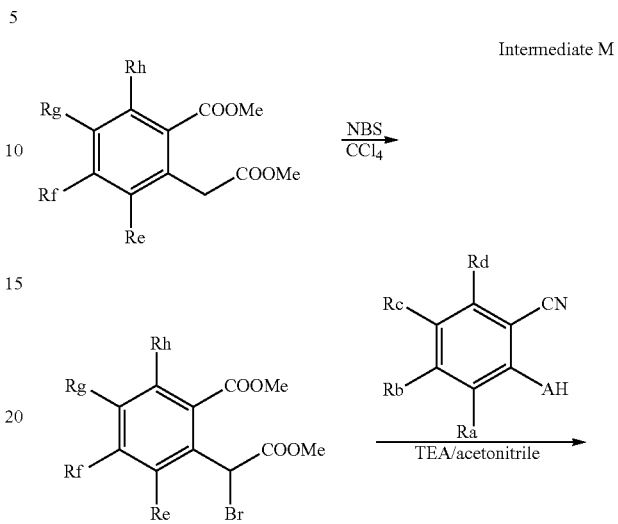

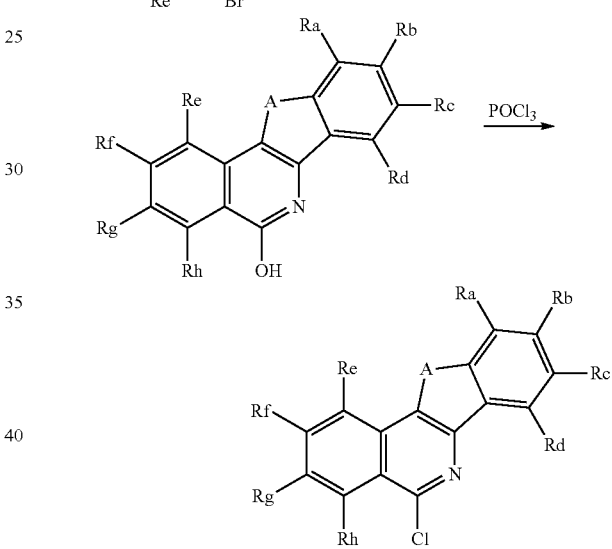

Specifically, when $Z_1$ links with O, the synthesis of intermediate M that used to synthesize the compound having the formula (Ib1) and the formula (Ib2) is as follows:

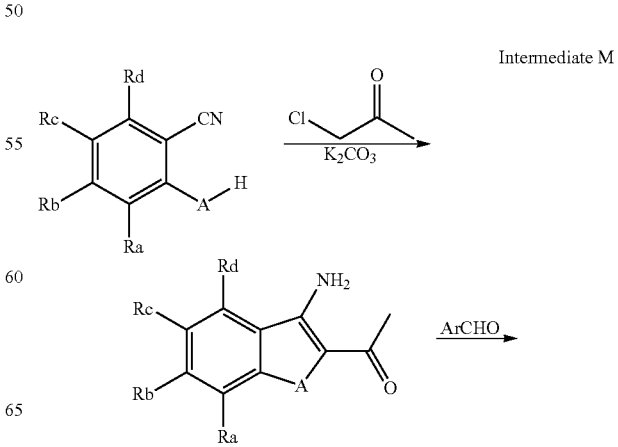

25

-continued

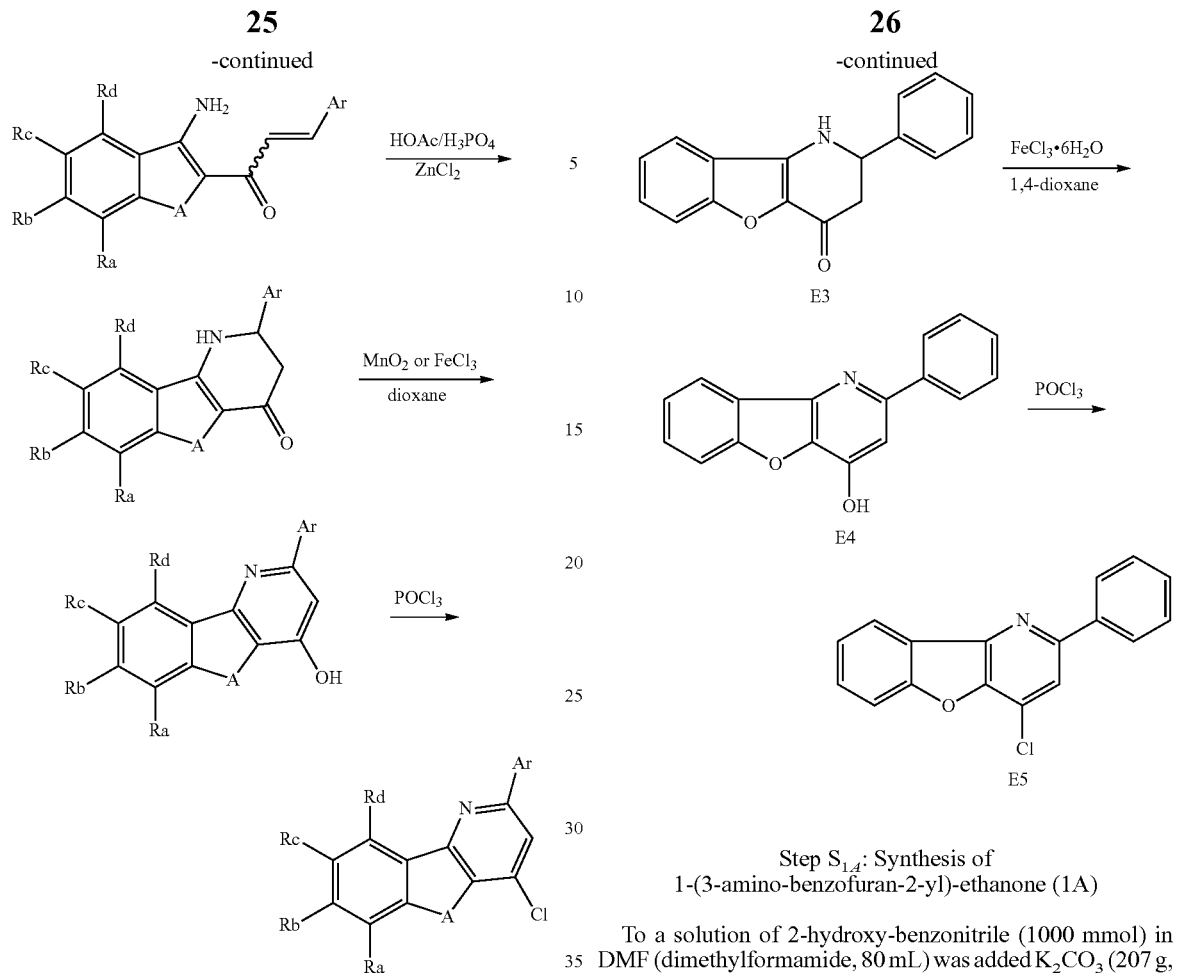

DETAILED DESCRIPTION OF THE INVENTION

EXAMPLE 1

Intermediate 1 (Abbreviated as M1, Same as Following)

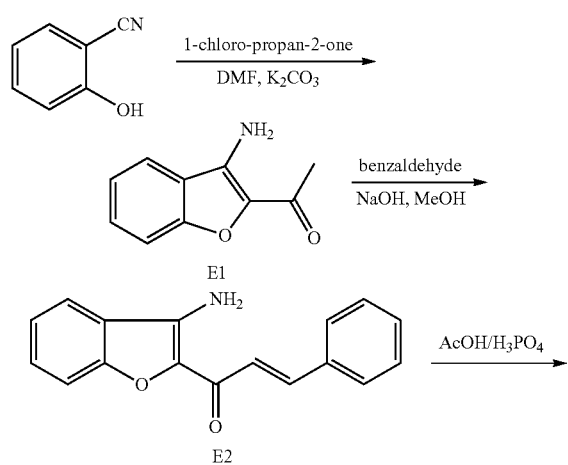

26

-continued

Step S$_{1A}$: Synthesis of 1-(3-amino-benzofuran-2-yl)-ethanone (1A)

To a solution of 2-hydroxy-benzonitrile (1000 mmol) in DMF (dimethylformamide, 80 mL) was added K$_2$CO$_3$ (207 g, 1.5 mol) portionwise under stirring, followed by 1-chloro-propan-2-one (139 g, 1.5 mol). After addition, the mixture was heated to 120° C. and stirred at that temperature for 2 hours. TLC showed the reaction was completed. The reaction mixture was cooled to room temperature and filtered. The filtrate was extracted with ethyl acetate, washed with brine, dried and concentrated. The residue was washed with dichloromethane, filtered and dried to give 112 g of 1-(3-amino-benzofuran-2-yl)-ethanone (1A).

$^1$H-NMR (DMSO): δ (ppm): 7.98 (d, J=8.0 Hz, 1H), 7.52 (m, 2H), 7.28 (dt, J=6.4, 1.6 Hz, 1H), 6.95 (brs, 2H), 2.37 (s, 3H). MS (ESI): M$^+$+1=176.18.

Step S$_{1B}$: Synthesis of (E) 2-cinnamoyl-3-amino-benzofuran (1B)

To a solution of 1A (114 mmol) in MeOH (200 mL) was added NaOH (18.2 g, 445 mmol). The reaction was exothermic. After cooled to room temperature, benzaldehyde (14.5 g, 137 mmol) was added. The mixture was stirred overnight under N$_2$. TLC monitored the reaction. After the reaction completed, the reaction mixture was poured into ice-water under stirring. The solids precipitated out and were collected by filtration, and dried to give 1B (26 g).

$^1$H-NMR (DMSO): δ (ppm): 8.03 (d, J=8 Hz, 1H), 7.80 (dd, J1=7.6 Hz, J2=1.6 Hz, 2H), 7.70 (d, J=16 Hz, 1H), 7.55-7.59 (m, 3H), 7.47 (m, 3H), 7.44-7.48 (m, 3H). MS (ESI): M$^+$+1=265.3.

Step S$_{1C}$: Synthesis of 2-phenyl-2,3-dihydrobenzofuron[3,2-b]pyridin-4(1H)-one (1C)

1B (98 mmol) was dissolved in a mixture of AcOH (150 ml) and H$_3$PO$_4$ (150 mL) The reaction mixture was heated to 120° C., and reacted under stirring for 4 hours. TLC monitored the reaction. After the reaction completed, the mixture was cooled and poured into ice-water, filtered and dried to give 1C (21 g).

¹H-NMR (DMSO): δ (ppm): 7.98 (s, 1H), 7.97 (d, J=8.4 Hz, 2H), 7.59 (q, J1=10.4 Hz, J2=7.6 Hz,4H), 7.45 (t, J=7.2 Hz, 2H), 7.39 (t, J=7.4 Hz, 1H), 7.32 (m, 1H), 4.98 (dd, J1=14 Hz, J2=4.4 Hz, 1H), 2.86 (dd, J=14, 16.4 Hz, 1H), 2.57 (dd, J=16.4, 4.4 Hz, 1H). MS (ESI): M⁺+1=264.3.

Step S$_{1D}$: Synthesis of 2-phenyl-4-hydroxyl-benzo[4,5]furo[3,2-b]pyridine (1D)

To a solution of 1C (79.7 mmol) in 1,4-dioxane (100 mL) was added FeCl$_3$.6H$_2$O (110 g, 400 mmol). The mixture was refluxed for 3 hours. TLC showed the reaction completed. The mixture was cooled and poured into cold diluted hydrochloric acid aqueous solution under stirring. The solids were precipitated out and collected by filtration, dried to give 1D (14 g).

¹H-NMR (DMSO-d$_6$): δ (ppm): 10.61 (s, 1H), 8.55 (s, 1H), 8.15 (d, J=7.6 Hz, 1H), 8.02 (d, J=8.4 Hz, 2H), 7.55-7.63 (m, 4H), 7.38 (t, J=4.6 Hz, 1H), 7.33 (t, J=3.8 Hz, 1H). MS (ESI): M⁺+1=262.27.

Step S$_{1E}$: Synthesis of 4-chloro-2-phenyl-benzofuro[3,2-b]pyridine (M1)

1D (53.6 mmol) was added to POCl$_3$ (90 mL), heated to dissolve and stirred at 110° C. for 2.5 hours. TLC showed the reaction completed. POCl$_3$ was evaporated under reduced pressure. The residue was cooled and poured into ice-water under stirring. The solids were collected by filtration and dried to give the desired product M1 (11.5 g).

¹H-NMR (DMSO-d$_6$): δ (ppm): 8.29 (s, 1H), 8.22-8.27 (m, 3H), 7.91 (d, J=8.0 Hz, 1H), 7.76 (dt, J=8.2, 1.6 Hz, 1H), 7.49-7.59 (m, 4H). MS (ESI): M⁺+1=280.7.

EXAMPLE 2

Intermediate 2 (M2)

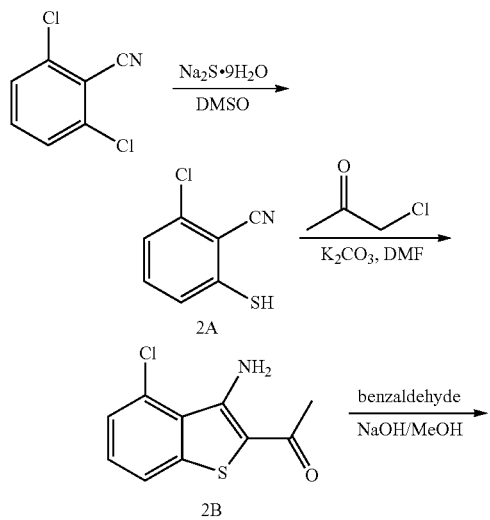

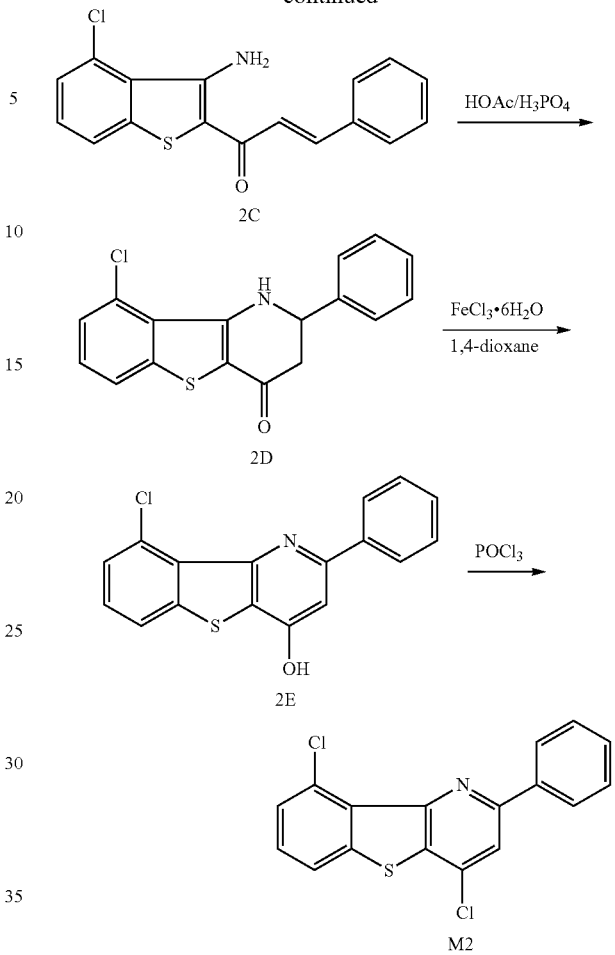

Step S$_{2A}$: Synthesis of 2-chloro-6-mercapto-benzonitrile (2A)

The solution of 2,6-dichloro-benzonitrile (20 mmol) in DMSO (dimethyl sulfoxide, 30 mL) was heated to 70° C., followed by addition of Na$_2$S.9H$_2$O portionwise under stirring. The mixture was stirred for 1 hour. TLC monitored the reaction. After the reaction completed, the mixture was cooled and extracted between water and ethyl acetate. The aqueous layer was acidified by hydrochloric acid to pH=3~4 under stirring. The formed solids were collected by filtration and dried to give 2.3 g of 2-chloro-6-mercapto-benzonitrile (2A). MS (ESI): M⁺+1=170.6.

Step S$_{2B}$: Synthesis of 1-(3-amino-4-chloro-benzothiophen-2-yl)-ethanone (2B)

The procedure was similar to step S$_{1A}$, while the starting material was 2-chloro-6-mercapto-benzonitrile (2A) in stead of 2-hydroxy-benzonitrile.

¹H-NMR (DMSO-d$_6$): δ (ppm): 7.89 (dd, J=8 Hz, J=0.8 Hz, 1H), 7.84 (b, 2H), 7.53 (t, J=16 Hz, 1H), 7.45 (dd, J1=7.6 Hz, J2=1.2 Hz, 1H), 2.37 (s, 3H). MS (ESI): M⁺+1=226.7.

Step S$_{2C}$: Synthesis of (E) 2-cinnamoyl-3-amino-4-chloro-benzo[b]thiophene (2C)

The procedure was similar to step S$_{1B}$, while the starting material was 2B in stead of 1A.

$^1$H-NMR (DMSO-d$_6$): δ (ppm): 8.19 (b, 2H), 7.92 (d, J=8.4 Hz, 1H), 7.79 (m, 2H), 7.70 (d, J=15.6 Hz, 1H), 7.56 (t, J=7.6 Hz, 1H), 7.46-7.49 (m, 4H), 7.24 (d, J=15.6 Hz, 1H). MS (ESI): M$^+$+1=315.8.

Step S$_{2D}$: Synthesis of 2-phenyl-9-chloro-2,3-dihydro-benzo[4,5]thieno[3,2-b]pyridin-4(1H)-one (2D)

The procedure was similar to step S$_{1C}$, while the starting material was 2C in stead of 1B.

MS (ESI): M$^+$+1=314.8.

Step S$_{2E}$: Synthesis of 2-phenyl-9-chloro-4-hydroxyl-benzo[4,5]thieno[3,2-b]pyridine (2E)

The procedure was similar to step S$_{1D}$, while the starting material was 2D in stead of 1C.

$^1$H-NMR (DMSO): δ (ppm): 11.95 (s, 1H), 8.24 (d, J=8.0 Hz, 2H), 8.12 (dd, J1=7.6 Hz, J2=0.8 Hz, 1H), 7.65 (dd, J=6.4, 1.2 Hz, 1H), 7.61 (d, J=8.0 Hz, 1H), 7.57 (t, J=8.0 Hz, 1H), 7.52 (s, 1H), 7.49 (t, J=7.2 Hz, 1H). MS (ESI): M$^+$+1=312.8.

Step S$_{2F}$: Synthesis of 4,9-dichloro-2-phenyl-benzo[4,5]thieno[3,2-b]pyridine (M2)

The procedure was similar to step S$_{1E}$, while the starting material was 2E in stead of 1D.

$^1$H-NMR (DMSO): δ (ppm): 8.43 (s, 1H), 8.40 (dd, J=1.2, 7.6 Hz, 2H), 8.20 (dd, J1=7.6 Hz, J2=1.2 Hz, 1H), 7.73 (dd, J=1.2, 8.0 Hz, 1H), 7.68 (t, J=7.6 Hz, 1H), 7.59 (t, J=7.6 Hz, 2H), 7.53 (dt, J=2.0, 7.6 Hz, 1H). MS (ESI): M$^+$+1=331.2.

EXAMPLE 3

Intermediate 3 (M3)

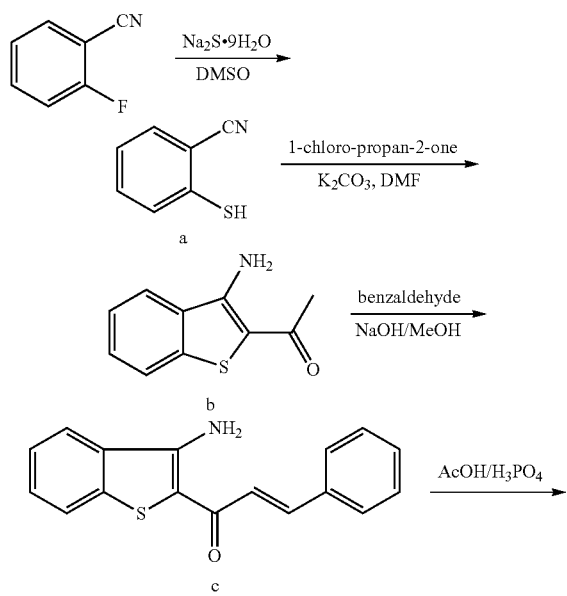

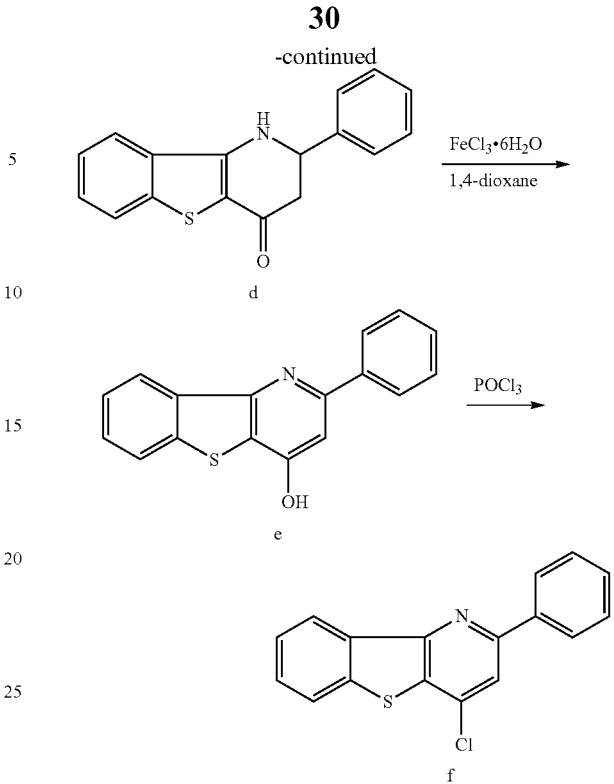

Step S$_{3A}$: Synthesis of 2-mercapto-benzonitrile (3A)

The procedure was similar to step S$_{2A}$, while the starting material was 2-fluoro-benzonitrile in stead of 2,6-dichloro-benzonitrile.

MS (ESI): M$^+$+1=136.2.

Step S$_{3B}$: Synthesis of 1-(3-amino-benzo[b]thiophen-2-yl)-ethanone (3B)

The procedure was similar to step S$_{1A}$, while the starting material was 2-mercapto-benzonitrile (3A) in stead of 2-hydroxy-benzonitrile.

$^1$H-NMR (DMSO-d$_6$): δ (ppm): 8.19 (d, J=8.4 Hz, 2H), 7.86 (t, J=7.0 Hz, 3H), 7.55 (t, J=7.2 Hz, 1H), 7.43 (t, J=7.2 Hz, 1H), 2.35 (s, 3H). MS (ESI): M$^+$+1=193.2.

Step S$_{3C}$: Synthesis of (E)-2-cinnamoyl 3-amino-benzo[b]thiophene (3C)

The procedure was similar to step S$_{1B}$, while the starting material was 3B in stead of 1A.

$^1$H-NMR (DMSO-d$_6$): δ (ppm): 8.25 (m, 3H), 7.91 (d, J=8.4 Hz, 1H), 7.79 (d, J=15.6 Hz, 2H), 7.69 (d, J=7.2 Hz, 1H), 7.61 (t, J=7.6 Hz, 1H), 7.46 (t, J=6.4 Hz, 4H), 7.23 (d, J=15.6 Hz, 1H). MS (ESI): M$^+$+1=280.3.

Step S$_{3D}$: Synthesis of 2-phenyl-2,3-dihydro-benzo[4,5]thieno[3,2-b]pyridin-4(1H)-one (3D)

The procedure was similar to step S$_{1C}$, while the starting material was 2C in stead of 1B.

MS (ESI): M$^+$+1=280.3.

Step S_{3E}: Synthesis of 2-phenyl-4-hydroxyl-benzothieno[3,2-b]pyridine (3E)

The procedure was similar to step S_{1D}, while the starting material was 3D in stead of 1C.

MS (ESI): M⁺+1=278.3.

Step S_{3F}: Synthesis of 4-chloro-2-phenyl-benzothieno[3,2-b]pyridine (M3)

The procedure was similar to step S_{1E}, while the starting material was 3E in stead of 1D.

$^1$H-NMR (DMSO-d$_6$): δ (ppm): 8.54 (d, J=7.6 Hz, 1H), 8.35 (s, 1H), 8.34 (dd, J=1.6, 7.6 Hz, 1H), 8.20 (d, J=7.6 Hz, 1H), 7.74 (dt, J=7.2, 1.2 Hz, 1H), 7.68 (dt, J=7.6, 1.6 Hz, 1H), 7.51-7.60 (m, 3H). MS (ESI): M⁺+1=296.8.

EXAMPLE 4

Intermediate 4 (M4)

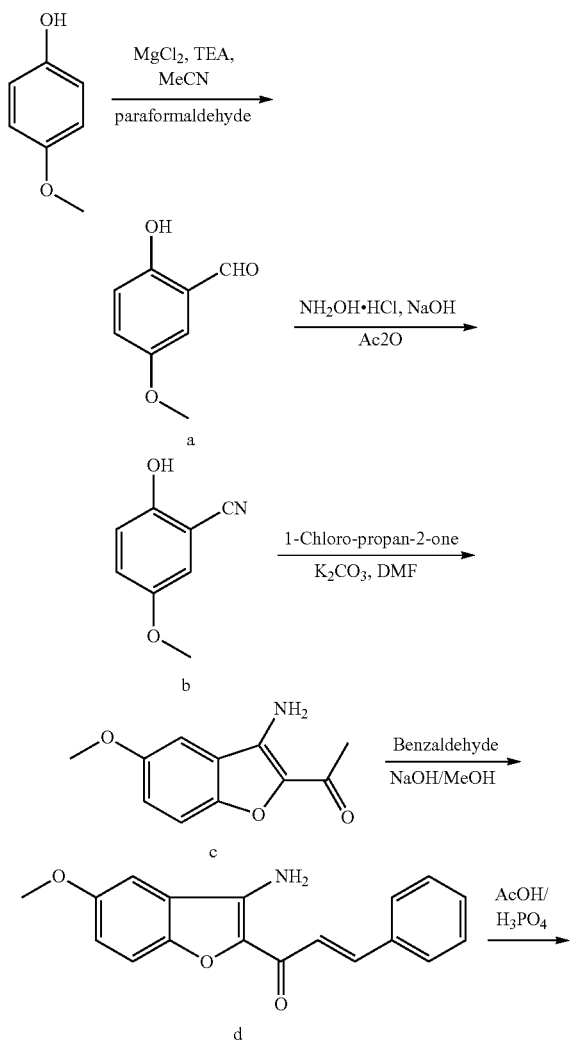

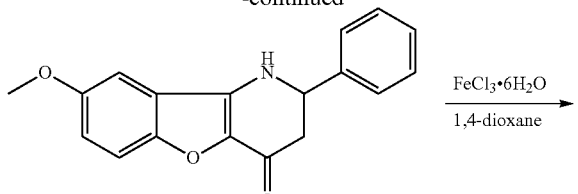

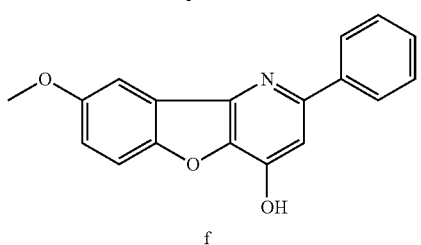

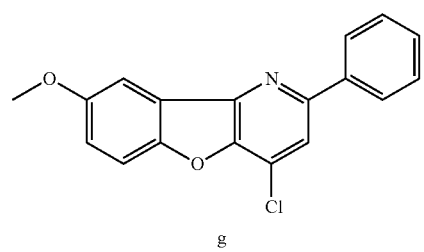

Step S_{4A}: Synthesis of 2-hydroxy-5-methoxy-benzaldehyde (4A)

To a mixture of MgCl$_2$ (3.48 g, 37.0 mmol), TEA (12.8 mL, 92.1 mmol) and paraformaldehyde (5 g, 167 mmol) in MeCN (100 mL) was added 4-methoxy-phenol (3 g, 24.2 mmol). The mixture was refluxed for 8 hours, cooled to room temperature, then poured into 5% HCl (300 mL), extracted with ethyl acetate (200 mL×3). The combined organic layer was dried, concentrated and purified by column chromatography on silica gel (ethyl acetate/n-hexane=1/5) to give 2.3 g of 2-hydroxy-5-methoxy-benzaldehyde (4A).

$^1$H-NMR (DMSO-d$_6$): δ (ppm): 10.67 (s, 1H), 9.87 (s, 1H), 7.18 (dd, J1=8.8 Hz, J2=3.6 Hz, 1H), 7.02 (d, J=2.8 Hz, 1H), 6.95 (d, J=8.8 Hz, 1H), 3.83 (s, 3H). MS (ESI): M⁺+1=153.15.

Step S_{4B}: Synthesis of 2-hydroxy-5-methoxy-benzonitrile (4B)

To a solution of 2-hydroxy-5-methoxy-benzaldehyde (10 g, 65.7 mmol) in 95% EtOH (30 mL) was added a solution of hydroxylamine hydrochloride (2.8 g, 78.8 mmol) in water (6 mL), followed a solution of NaOH (4 g, 98.8 mmol) in water. The mixture was stirred at room temperature for 2.5 hours, then extracted with ethyl acetate, dried over anhydrous Na$_2$SO$_4$ and concentrated to give 12 g of solid. To the solid was added Ac$_2$O (15 g, 146.9 mmol) and the mixture was refluxed for 20 min. TLC monitored the reaction. After the reaction completed, the mixture was poured into crash ice. Solids were precipitated out while stirring, which was collected by filtration and dried to give 9 g of 2-hydroxy-5-methoxy-benzonitrile (4B).

MS (ESI): M⁺+1=150.15.

Step S₄C: Synthesis of 1-(3-amino-5-methoxy-benzofuran-2-yl)-ethanone (4C)

The procedure was similar to step S₁ₐ, while the starting material was 2-hydroxy-5-methoxy-benzonitrile (4B) instead of 2-hydroxy-benzonitrile.
¹H-NMR (DMSO-d₆): δ (ppm): 7.52 (d, J=2.4 Hz, 1H), 7.41 (d, J=9.2 Hz, 1H), 7.13 (dd, J=2.8, 9.2 Hz, 1H), 6.82 (s, 2H), 3.79 (s, 3H), 2.34 (s, 3H). MS (ESI): M⁺+1=208.23.

Step S₄D: Synthesis of (E)-2-cinnamoyl-3-amino-5-methoxy-benzofuran (4D)

The procedure was similar to step S₁B, while the starting material was 4C instead of 1A.
MS (ESI): M⁺+1=294.32.

Step S₄E: Synthesis of 2-phenyl-8-methoxy-2,3-dihydro-benzofuro[3,2-b]pyridin-4(1H)-one (4E)

The procedure was similar to step S₁C, while the starting material was 4D instead of 1B.
MS (ESI): M⁺+1=294.32.

Step S₄F: Synthesis of 2-phenyl-4-hydroxyl-8-methoxy-benzofuro[3,2-b]pyridine (4F)

The procedure was similar to step S₁D, while the starting material was 4E instead of 1C.
MS (ESI): M⁺+1=292.3.

Step S₄G: Synthesis of 4-chloro-8-methoxy-2-phenyl-benzofuro[3,2-b]pyridine (M4)

The procedure was similar to step S₁E, while the starting material was 4F instead of 1D.
¹H-NMR (DMSO-d₆): δ (ppm): 8.29 (s, 1H), 8.26 (dd, J1=6.8 Hz, J2=1.6 Hz, 2H), 7.83 (d, J=8.8 Hz, 1H), 7.70 (d, J=2.8 Hz, 1H), 7.55 (t, J=6.4 Hz, 2H), 7.51 (t, J=7.2 Hz, 1H), 7.31 (dd, J1=8.8 Hz, J2=2.8 Hz, 1H), 3.93 (s, 1H). MS (ESI): M⁺+1=310.75.

EXAMPLE 5

Intermediate 5 (M5)

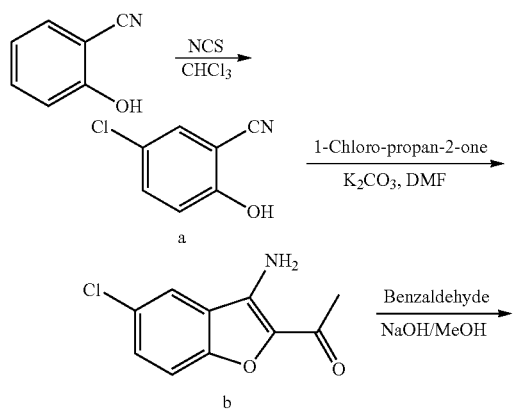

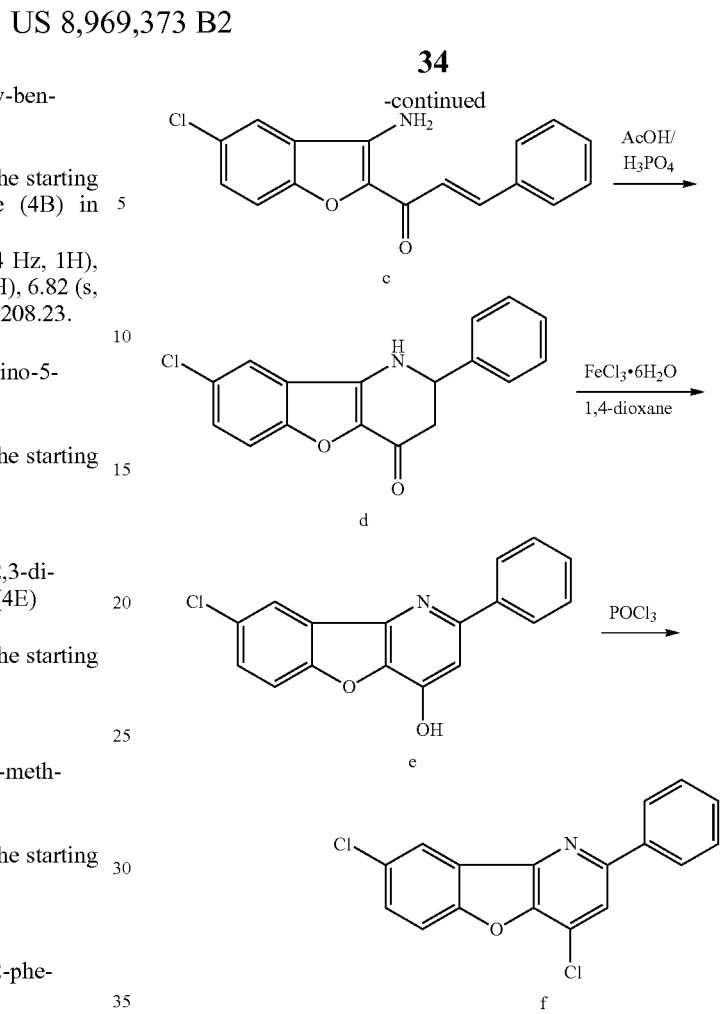

Step S₅ₐ: Synthesis of 5-chloro-2-hydroxy-benzonitrile (5A)

To a solution of 2-hydroxy-benzonitrile (5 g, 42 mmol) in chloroform (50 mL) was added 15 mL of a solution of NCS (N-chlorosuccinimide, 5.558 g, 44.1 mmol) in chloroform. The reaction mixture was refluxed overnight. TLC monitored the reaction. After the reaction completed, the mixture was poured into ice-water. The organic layer was washed with water, then stayed overnight.

The precipitated solids were collected by filtration. The filtrate was concentrated, recrystallized from chloroform and filtered to give a solid. The two batches of product were combined to give 4 g of 5-chloro-2-hydroxy-benzonitrile (5A).
¹H-NMR (DMSO-d₆): δ (ppm): 11.44 (s, 1H), 7.77 (d, J=2.4 Hz, 1H), 7.55 (dd, J1=8.8 Hz, J2=2.4 Hz, 1H), 7.02 (d, J=9.2 Hz, 1H). MS (ESI): M⁺+1=154.6.

Step S₅B: Synthesis of 1-(3-amino-5-chloro-benzofuran-2-yl)-ethanone (5B)

The procedure was similar to step S₁ₐ, while the starting material was 5-chloro-2-hydroxy-benzonitrile (5A) instead of 2-hydroxy-benzonitrile.
¹H-NMR (DMSO-d₆): δ (ppm): 8.09 (q, 1H), 7.55 (t, J=1.2 Hz, 2H), 6.92 (b, 2H), 2.37 (s, 3H). MS (ESI): M⁺+1=212.6.

Step S5C: Synthesis of (E)-2-cinnamoyl-3-amino-5-chloro-benzofuran (5C)

The procedure was similar to step S1B, while the starting material was 5B in stead of 1A.

$^1$H-NMR (DMSO-d$_6$): δ (ppm): 8.14 (m, 1H), 7.78-7.81 (m, 2H), 7.70 (d, J=15.6 Hz, 1H), 7.60 (m, 2H), 7.50 (d, J=15.6 Hz, 1H), 7.45-7.49 (m, 3H), 7.24 (b, 2H). MS (ESI): M$^+$+1=298.7.

Step S5D: Synthesis of 2-phenyl-8-chloro-2,3-dihydro-benzofuro[3,2-b]pyridin-4(1H)-one (5D)

The procedure was similar to step S1C, while the starting material was 5C in stead of 1B.

MS (ESI): M$^+$+1=298.7.

Step S5E: Synthesis of 2-phenyl-8-chloro-4-hydroxyl-benzofuro[3,2-b]pyridine (5E)

The procedure was similar to step S1D, while the starting material was 5D in stead of 1C.

MS (ESI): M$^+$+1=296.7.

Step S5F: Synthesis of 4,8-dichloro-2-phenyl-benzo[4,5]furo[3,2-b]pyridine (M5)

The procedure was similar to step S1E, while the starting material was 5E in stead of 1D.

$^1$H-NMR (DMSO-d$_6$): δ (ppm): 8.37 (s, 1H), 8.30 (d, J=2.4 Hz, 1H), 8.25 (dd, J1=8.4 Hz, J2=1.6 Hz, 2H), 7.96 (d, J=8.8 Hz, 1H), 7.78 (dd, J1=8.8 Hz, J2=2.4 Hz, 1H), 7.55 (dt, J=7.6, 1.6 Hz, 2H), 7.52 (t, J=7.6 Hz, 1H). MS (ESI): M$^+$+1=315.2.

EXAMPLE 6

Intermediate 6 (M6)

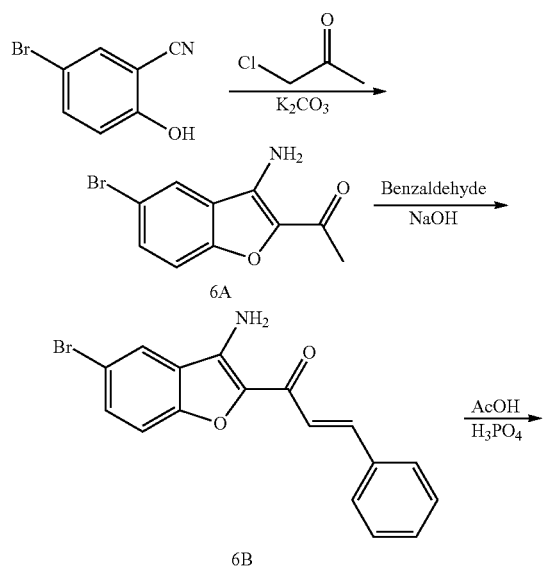

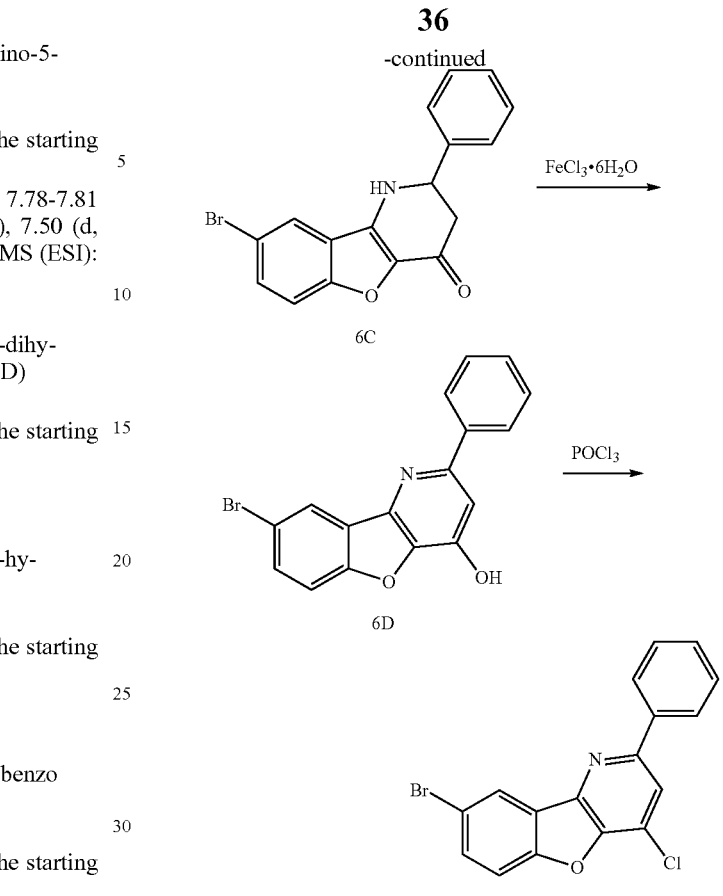

Step S6A: Synthesis of 1-(3-amino-5-bromo-benzofuran-2-yl)-ethanone (6A)

A mixture of 5-bromo-2-hydroxy-benzonitrile (15.06 g, 76.06 mmol), 1-chloro-propan-2-one (10.56 g, 114.09 mmol, 1.5 eq) and K$_2$CO$_3$ (15.77 g, 114.09 mmol, 1.5 eq) was added to DMF (100 mL) The mixture was stirred at 90° C. for 2 hours. TLC monitored the reaction. After the reaction completed, the mixture was cooled to room temperature and poured into water (500 mL).

The yellow solids precipitated out were collected by filtration to give 1-(3-amino-5-bromo-benzofuran-2-yl)-ethanone (6A) (19.2 g, 99.36% yield).

$^1$H-NMR (400 MHz, DMSO-d$_6$): δ (ppm): 8.24 (d, J=2.0 Hz, 1H), 7.64-7.67 (dd, J1=8.8 Hz, J2=2.0 Hz, 1H), 7.51 (d, J=8.8 Hz, 1H), 6.91 (s, 2H), 2.37 (s, 3H).

Step S6B: Synthesis of (Z)-2-cinnamoyl-3-amino-5-bromo-benzofuran (6B)

A mixture of 1-(3-amino-5-bromo-benzofuran-2-yl)-ethanone (19.2 g, 75.57 mmol), NaOH (12.09 g, 302.27 mmol, 4 eq) and benzaldehyde (10.42 g, 98.24 mmol, 1.3 eq) was added to MeOH (400 mL) The mixture was stirred at 45° C. for 48 hours. TLC monitored the reaction. After the reaction completed, the mixture was cooled to room temperature and poured into water (400 mL).

The yellow solids precipitated out were collected by filtration to give (Z)-2-cinnamoyl-3-amino-5-bromo-benzofuran (6B) (28 g, 100% yield).

$^1$H-NMR (400 MHz, DMSO-d$_6$) δ 8.29 (d, J=1.6 Hz, 1H), 7.78-7.80 (m, 2H), 7.68-7.72 (m, 2H), 7.57 (s, 1H), 7.54 (d, J=8.4 Hz, 1H), 7.45-7.48 (m, 3H), 7.24 (s, 2H).

Step S$_{6C}$: Synthesis of 8-bromo-2-phenyl-2,3-dihydro-benzofuro[3,2-b]pyridin-4(1H)-one (6C)

A solution of (Z)-2-cinnamoyl-3-amino-5-bromo-benzofuran (28 g, 81.83 mmol) in AcOH (70 mL) and H$_3$PO$_4$ (70 mL) was refluxed for 2 hours. TLC showed the reaction completed. The mixture was cooled to room temperature and poured into water (250 mL) The yellow solids precipitated out were collected by filtration to give 8-bromo-2-phenyl-2,3-dihydro-benzofuro[3,2-b]pyridin-4(1H)-one (6C) (23.8 g, 85% yield).

$^1$H-NMR (400 MHz, DMSO-d$_6$) δ 8.2 (d, J=1.6 Hz, 1H), 7.94 (s, 1H), 7.70-7.73 (dd, J1=9.2 Hz, J2=2.8 Hz, 1H), 7.56-7.59 (m, 3H), 7.44 (t, J=7.2 Hz, 3H), 7.37-7.40 (m, 1H), 4.97 (dd, J1=14.6 Hz, J2=4.8 Hz, 1H), 2.87 (dd, J1=16.4 Hz, J2=14.0 Hz, 1H), 2.54-2.60 (dd, J1=16.0 Hz, J2=4.4 Hz, 1H).

Step S$_{6D}$: Synthesis of 4-hydroxyl-8-bromo-2-phenyl-benzofuro[3,2-b]pyridine (6D)

A mixture of 8-bromo-2-phenyl-2,3-dihydro-benzofuro[3,2-b]pyridin-4(1H)-one (23.8 g, 69.55 mmol) and FeCl$_3$.6H$_2$O (112.78 g, 417.3 mmol) was added to 1,4-dioxane (300 mL) The mixture was refluxed for 16 hours. TLC showed the reaction completed. The mixture was cooled to room temperature and poured into ice-water (500 mL) The yellow solids precipitated out were collected by filtration to give 4-hydroxyl-8-bromo-2-phenyl-benzofuro[3,2-b]pyridine (6D) (15.7 g, 66.36% yield).

Step S$_{6E}$: Synthesis of 8-bromo-4-chloro-2-phenyl-benzofuro[3,2-b]pyridine (M6)

4-hydroxyl-8-bromo-2-phenyl-benzofuro[3,2-b]pyridine (8.7 g, 25.72 mmol) was added to POCl$_3$ (100 mL) The mixture was refluxed for 4 hours. TLC showed the reaction completed. POCl$_3$ was evaporated under reduced pressure. The residue was poured into ice-water under stirring. The yellow solids precipitated out were collected by filtration to give 8-bromo-4-chloro-2-phenyl-benzofuro[3,2-b]pyridine (M6) (6.52 g, 71.01% yield).

$^1$H-NMR (400 MHz, CDCl$_3$) δ 8.43 (s, 1H), 8.09 (d, J=7.2 Hz, 2H), 7.87 (s, 1H), 7.70-7.74 (dd, J1=8.8 Hz, J2=2.0 Hz, 1H), 7.53-7.59 (m, 3H), 7.47-7.51 (m, 1H).

EXAMPLE 7

Synthesis of 7G

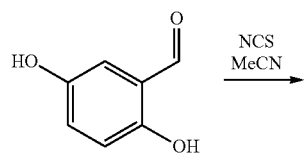

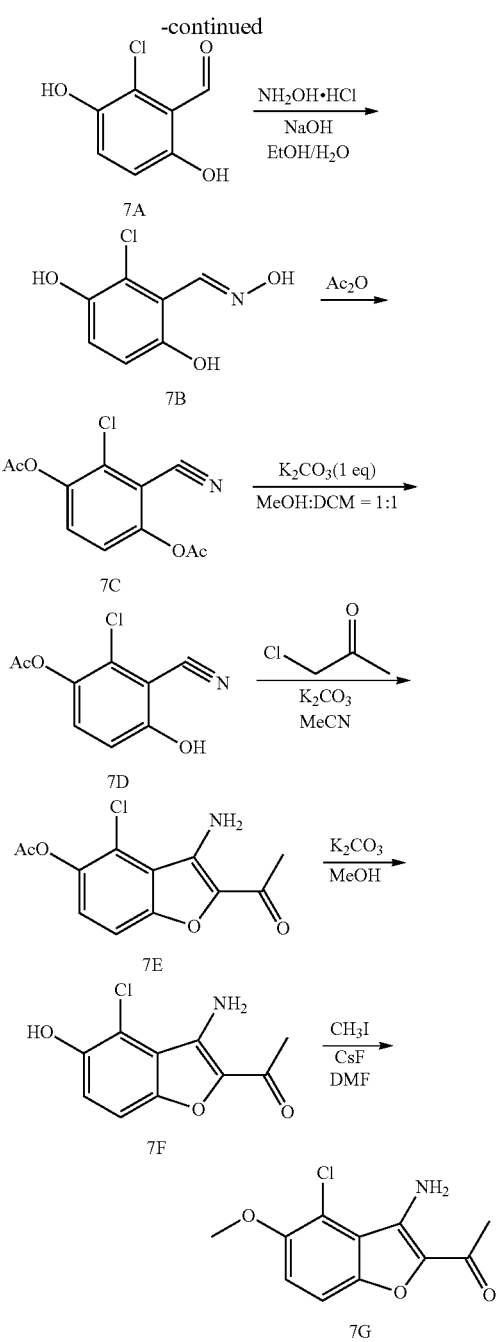

Step S$_{7A}$: Synthesis of 2-chloro-3,6-dihydroxy-benzaldehyde (7A)

2,5-dihydroxy-benzaldehyde (100 g, 0.725 mol) was dissolved in MeCN (1L). To the solution was added NCS(N-chlorosuccinimide, 106 g, 1.1 eq) in batches under N$_2$ protection. After addition completed, the mixture was stirred at room temperature overnight. TLC monitored the reaction. After the reaction completed, NaHSO$_3$(38%, 500 mL) was added to the mixture, then extracted with ethyl acetate (3×600 mL) The organic layer was washed with water (2×600 mL) and brine (600 mL), dried over anhydrous MgSO$_4$, concentrated to give a crude product, which was recrystallized to give the desired product 7A (25.6 g, 20.5% yield), as a yellow solid.

$^1$H-NMR (400 MHz, DMSO-d$_6$): δ 11.09 (s, 1H), 10.34 (s, 1H), 9.94 (s, 1H), 7.23 (d, J=9.2 Hz, 1H), 6.84 (d, J=8.8 Hz, 1H).

Step S$_{7B}$: Synthesis of
(E)-2-chloro-3,6-dihydroxy-benzaldehyde oxime
(7B)

A mixture of 7A (25.0 g, 144.87 mmol), hydroxylamine hydrochloride (12.08 g, 173.84 mmol, 1.2 eq) and NaOH (8.69 g, 217.3 mmol, 1.5 eq) in EtOH (200 mL) and H$_2$O (100 mL) was stirred at room temperature overnight. TLC monitored the reaction. After the reaction completed, the mixture was extracted with ethyl acetate and concentrated to give a yellow solid 7B (34.2 g, 100% yield).

Step S$_{7C}$: Synthesis of
2-chloro-3-cyano-1,4-diacetoxy-benzene (7C)

7B (34.2 g, 182.32 mmol) was dissolved in Ac$_2$O (200 mL) The reaction mixture was refluxed for 24 hours under stirring. TLC monitored the reaction. After the reaction completed, the mixture was cooled to room temperature and poured into water (250 mL), extracted with ethyl acetate, concentrated and purified by column chromatography on silica gel to give product 7C (17.3 g, 37.2% yield).

Step S$_{7D}$: Synthesis of acetic acid
2-chloro-3-cyano-4-hydroxy-phenyl ester (7D)

7C (13.8 g, 54.4 mmol) was dissolved in MeOH (80 ml) and dichloromethane (80 mL). To the solution was added K$_2$CO$_3$ (7.52 g, 54.4 mmol, 1 eq). The reaction mixture was stirred at room temperature for 40 min. TLC monitored the reaction. After the reaction completed, the mixture was acidified by 1N hydrochloric acid to pH~6, extracted with dichloromethane and concentrated to give white solid 7D (7.8 g, 67.76% yield).
$^1$H-NMR (400 MHz, CDCl$_3$) δ 11.76 (s, 1H), 7.46 (d, J=9.2 Hz, 1H), 7.03 (d, J=9.2 Hz, 1H), 2.32 (s, 3H).

Step S$_{7E}$: Synthesis of
2-acetyl-3-amino-4-chloro-5-acetoxyl-benzofuran
(7E)

To a solution of 7D (2.2 g, 10.4 mmol) in MeCN (20 mL) was added 1-chloro-propan-2-one (1.25 g, 13.52 mmol, 1.3 eq), followed by K$_2$CO$_3$ (1.868 g, 13.52 mmol, 1.3 eq). The mixture was stirred at 90° C. for 40 min. TLC monitored the reaction. After the reaction completed, the mixture was quenched with water (100 mL) The white solids were precipitated out and collected by filtration and dried to give product 7E (3 g, 100% yield).

Step S$_{7F}$: Synthesis of
2-acetyl-3-amino-4-chloro-5-hydroxy-benzofuran
(7F)

To a solution of 7E (12.8 g, 47.82 mmol) in MeOH (100 mL) was added a solution of saturated aqueous of K$_2$CO$_3$ (6.61 g, 47.82 mmol, 1 eq.) dropwise. The mixture was stirred at room temperature overnight. TLC monitored the reaction. After the reaction completed, the mixture was acidified by 1N hydrochloric acid to pH~6, extracted with ethyl acetate and concentrated to give white solid 7F (10.2 g, 94.54% yield).

$^1$H-NMR (400 MHz, DMSO-d$_6$) δ 10.14 (s, 1H), 7.36 (d, J=8.8 Hz, 1H), 7.19 (d, J=8.8 Hz, 1H), 6.46 (s, 2H), 2.37 (s, 3H).

Step S$_{7G}$: Synthesis of
2-acetyl-3-amino-4-chloro-5-methoxyl-benzofuran
(7G)

To a solution of 7F (0.5 g, 2.22 mmol) in DMF (5 mL) was added anhydrous CsF (1.01 g, 6.65 mmol, 3 eq), followed by MeI (0.377 g, 2.66 mmol, 1.2 eq) dropwise. The mixture was stirred at room temperature for 40 min. TLC monitored the reaction. After the reaction completed, the mixture was poured into water (25 mL) The white solids were precipitated out, collected by filtration and purified to give product 7G (0.33 g, 62.14% yield).
$^1$H-NMR (400 MHz, CDCl$_3$) δ 7.50 (d, J=9.2 Hz, 1H), 7.42 (d, J=9.2 Hz, 1H), 6.51 (s, 2H), 3.89 (s, 3H), 2.38 (s, 3H).

EXAMPLE 8

Intermediate 8 (M8)

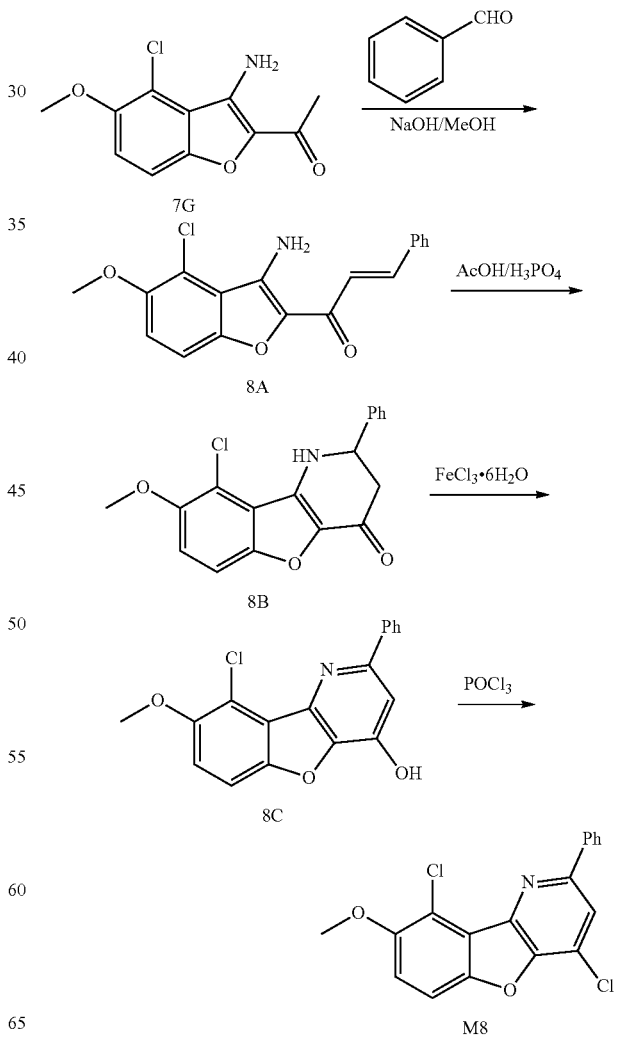

Step S<sub>8A</sub>: Synthesis of 2-cinnamoyl-3-amino-4-chloro-5-methoxy-benzofuran (8A)

A mixture of 7G (1.5 g, 6.26 mmol), benzaldehyde (0.863 g, 8.14 mmol, 1.3 eq) and NaOH (1.0 g, 25.04 mmol, 4 eq) in MeOH (20 mL) was stirred at 45° C. for 24 hours. TLC monitored the reaction. After the reaction completed, the reaction mixture was cooled to room temperature and poured into water (20 mL) The yellow solids precipitated out were collected by filtration and dried to give product 8A (1.9 g, 92.6% yield).

Step S<sub>8B</sub>: Synthesis of 9-chloro-8-methoxy-2-phenyl-2,3-dihydrobenzofuro[3,2-b]pyridin-4(1H)-one (8B)

A mixture of 8A (1.9 g, 5.8 mmol) in AcOH (10 mL) and $H_3PO_4$ (10 mL) was refluxed for 2 hours. TLC monitored the reaction. After the reaction completed, the reaction mixture was cooled to room temperature and poured into water (20 mL) The yellow solids were precipitated out, collected by filtration and dried to give product 8B (1.78 g, 93.68% yield).

Step S<sub>8C</sub>: Synthesis of 4-hydroxyl-9-chloro-8-methoxy-2-phenyl-benzofuro[3,2-b]pyridine (8C)

A mixture of 8B (1.78 g, 5.43 mmol) and $FeCl_3 \cdot 6H_2O$ (6.57 g, 32.58 mmol, 6 eq) was added to 1,4-dioxane (40 mL) The mixture was refluxed for 16 hours. TLC monitored the reaction. After the reaction completed, the reaction mixture was cooled to room temperature and poured into water (50 mL) The brown solids were precipitated out, collected by filtration and dried to give product 8C (1.5 g, 84.8% yield).

Step S<sub>8D</sub>: Synthesis of 4,9-dichloro-8-methoxy-2-phenyl-benzofuro[3,2-b]pyridine (M8)

A mixture of 8C (1.4 g, 4.3 mmol) in $POCl_3$ (20 mL) was refluxed for 2 hours. TLC monitored the reaction. After the reaction completed, $POCl_3$ was evaporated under reduced pressure. The residue was poured into ice-water. The yellow solids were precipitated out, collected by filtration and purified by column chromatography to give product M8 (1.22 g, 82.5% yield).

$^1$H-NMR (400 MHz, $CDCl_3$) δ 8.16 (d, J=7.2 Hz, 2H), 7.88 (s, 1H), 7.44-7.55 (m, 4H), 7.19-7.22 (d, J=8.8 Hz, 1H), 4.02 (s, 3H).

EXAMPLE 9

Intermediate 9 (M9)

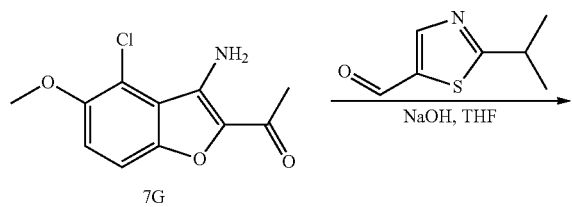

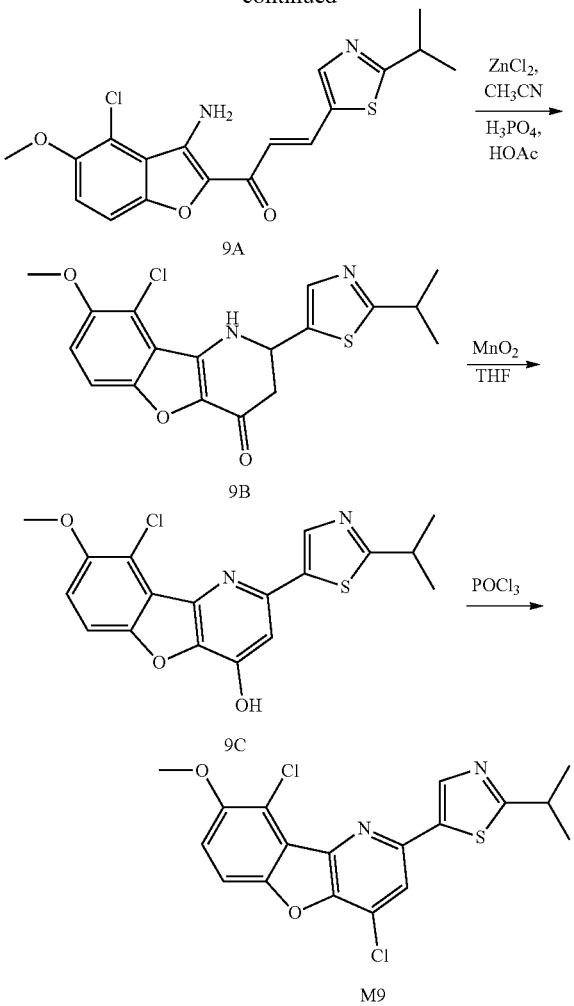

Step S<sub>9A</sub>: Synthesis of (E)-1-(3-amino-4-chloro-5-methoxy-benzofuran-2-yl)-3-(2-isopropyl-thiazol-5-yl)-2-propen-1-one (9A)

7G (3 g, 12.5 mmol) was dissolved in THF (tetrahydrofuran, 30 mL). To the solution was added 2-isopropyl-thiazole-5-carbaldehyde (2.33 g, 15 mmol, 1.2 eq), followed by crushed NaOH powder (1 g, 25 mmol, 2 eq). The reaction mixture was stirred at room temperature for 10 min. The solution became dark and some solids formed. The mixture was poured into ice-water under stirring.

The solids were collected by filtration, dried and purified by column chromatography on silica gel to give 3.5 g of pure product (9A).

$^1$H-NMR (400 MHz, $CDCl_3$) δ 7.88 (d, J=16.0 Hz, 1H), 7.86 (s, 1H), 7.32 (d, J=8.8 Hz, 1H), 7.21 (d, J=16.0 Hz, 1H), 7.19 (d, J=8.8 Hz, 1H), 6.38 (s, 2H), 3.97 (s, 3H), 3.35 (m, 1H), 1.44 (d, J=7.2 Hz, 6H); ES-LCMS m/z N/A.

Step S<sub>9B</sub>: Synthesis of 9-chloro-2-(2-isopropylthiazol-5-yl)-8-methoxy-1,2-dihydro-benzofuro[3,2-b]pyridin-4-one (9B)

9A (3.5 g, 9.28 mmol) was added to MeCN (50 mL) and stirred at room temperature. To the mixture was added $ZnCl_2$ (1.91 g, 13.93 mmol, 1.5 eq), followed by AcOH (50 mL) and H₃PO₄ (50 mL) The reaction mixture was heated to 80° C. and stirred overnight. After reaction completed, the mixture was cooled and poured into crushed ice under stirring, neutralized to pH=7~8, extracted with ethyl acetate, dried and concentrated to give 2.4 g of product (9B).

¹H-NMR (400 MHz, DMSO-d₆) δ 7.70 (s, 1H), 7.39 (d, J=8.8 Hz, 1H), 7.21 (d, J=8.8 Hz, 1H), 5.56 (brs, 1H), 5.25 (dd, J=12.0, 4.8 Hz, 1H), 3.97 (s, 3H), 3.25-3.35 (m, 1H), 2.29-3.02 (m, 2H), 1.45 (d, J=7.0 Hz, 6H).

Step S₉C: Synthesis of 4-hydroxyl-9-chloro-2-(2-isopropyl-thiazol-5-yl)-8-methoxy-benzofuro[3,2-b]pyridine (9C)

The crude 9B (2.4 g, 6.9 mmol) was dissolved in THF (50 mL). To the solution was added activated MnO₂ (3.6 g, 40.4 mmol, 6 eq). The mixture was refluxed overnight. After reaction completed, the reaction mixture was cooled and filtered. The cake was washed well with THF and MeOH. The filtrate was concentrated and purified by column chromatography on silica gel to give 300 mg of pure product (9C).

¹H-NMR (400 MHz, DMSO-d₆) δ 8.23 (s, 1H), 7.75 (d, J=8.8 Hz, 1H), 7.48 (s, 1H), 7.46 (d, J=8.8 Hz, 1H), 3.96 (s, 3H), 3.30 (m, 1H), 1.385 (d, J=7.3 Hz, 6H).

Step S₉D: Synthesis of 4,9-dichloro-2-(2-isopropyl-thiazol-5-yl)-8-methoxy-benzofuro[3,2-b]pyridine (M9)

A mixture of 9C (300 mg, 0.80 mmol) in POCl₃ (5 mL) was refluxed for 30 min. After reaction completed, POCl₃ was evaporated under reduced pressure. The residue was poured into crushed ice under stirring for 10 min. The solids were collected by filtration and dried to give 320 mg of crude product, which was dissolved in dichloromethane, purified by flash chromatography and concentrated to give 175 mg of pure product (M9).

¹H-NMR (400 MHz, CDCl₃) δ 8.15 (s, 1H), 7.79 (s, 1H), 7.567 (d, J=8.8 Hz, 1H), 7.268 (d, J=8.8 Hz, 1H), 4.04 (s, 3H), 3.39 (m, 1H), 1.50 (d, J=7.2 Hz, 6H); ES-LCMS m/z N/A.

EXAMPLE 10

Intermediate 10 (M10)

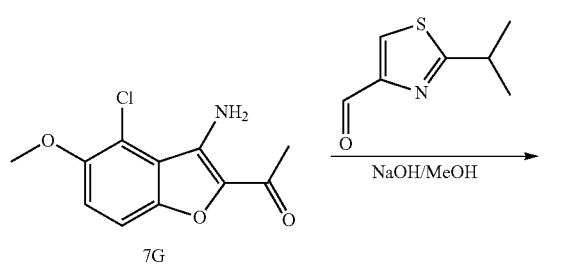

7G

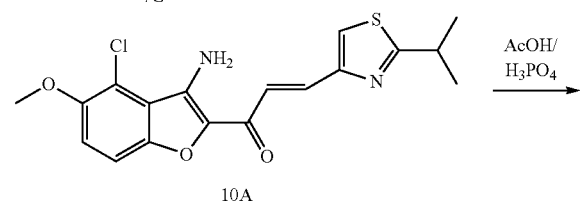

10A

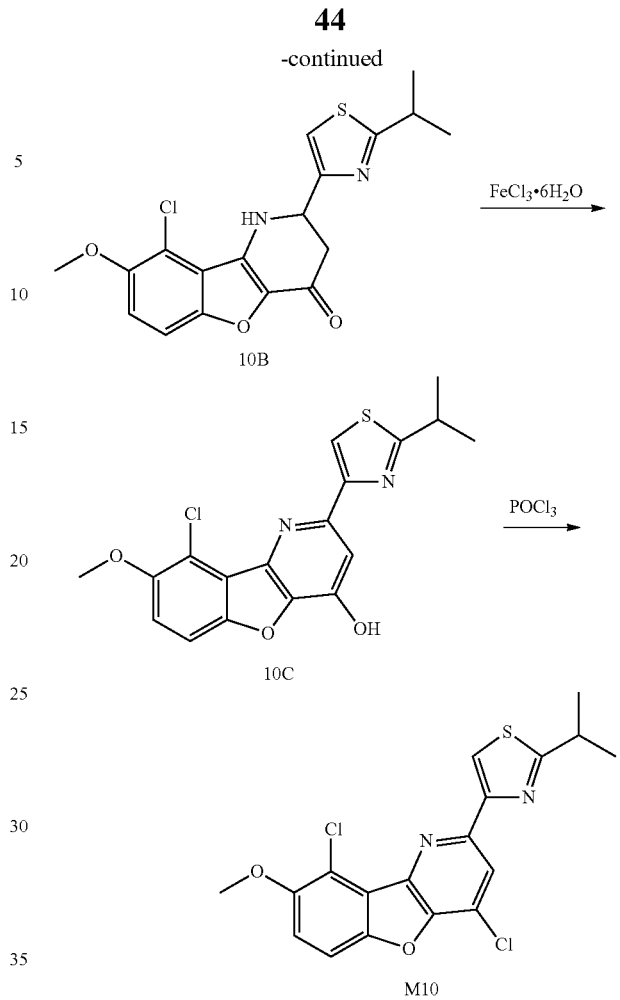

Step S₁₀A: Synthesis of 1-(3-amino-4-chloro-5-methoxy-benzofuran-2-yl)-3-(2-isopropyl-thiazol-4-yl)-2-propen-1-one (10A)

A mixture of 7G (6.4 g, 26.7 mmol), 2-isopropyl-thiazole-4-carbaldehyde (4.8 g, 30.92 mmol, 1.16 eq) and NaOH (4.27 g, 106.8 mmol, 4 eq) in MeOH (200 mL) was stirred at 45° C. for 24 hours. TLC monitored the reaction. After the reaction completed, the reaction mixture was cooled to room temperature and poured into water (200 mL) The yellow precipitates were collected by filtration and dried to give product 10A (9.96 g, 98.9% yield).

¹H-NMR (400 MHz, DMSO-d₆) δ 8.03 (s, 1H), 7.63 (s, 1H), 7.60 (d, J=9.2 Hz, 1H), 7.45-7.48 (d, J=9.2 Hz, 1H), 6.86 (s, 2H), 3.91 (s, 3H), 3.39 (m, 1H), 1.38 (d, J=6.4 Hz, 6H).

Step S₁₀B: Synthesis of 9-chloro-2-(2-isopropyl-thiazol-4-yl)-8-methoxy-2,3-dihydro-benzofuro[3,2-b]pyridin-4(1H)-one (10B)

10A (9.96 g, 26.43 mmol) was dissolved in AcOH (50 mL) and H₃PO₄ (50 mL). The solution was refluxed for 2 hours. TLC monitored the reaction. After the reaction completed, the reaction mixture was cooled to room temperature and poured into water (200 mL) The brown precipitates were collected by filtration and dried to give product 10B (10.8 g), which was used for the next step directly.

Step S10C: Synthesis of 4-hydroxyl-9-chloro-2-(2-isopropyl-thiazol-4-yl)-8-methoxy-benzofuro[3,2-b]pyridine (10C)

A mixture of 10B (10.3 g, 27.33 mmol, crude) and FeCl$_3$·6H$_2$O (33.04 g, 164.0 mmol, 6 eq) was added to 1,4-dioxane (300 mL) The mixture was refluxed for 16 hours. TLC monitored the reaction. After the reaction completed, the reaction mixture was cooled to room temperature and poured into water (300 mL), extracted with ethyl acetate and concentrated to give a crude product 10C (8.75 g), which was used for the next step directly.

Step S10D: Synthesis of 4,9-dichloro-2-(2-isopropyl-thiazol-4-yl)-8-methoxy-benzofuro[3,2-b]pyridine (M10)

The crude 10C (8.75 g, 23.34 mmol) was added to POCl$_3$ (200 mL) The mixture was refluxed for 2 hours. TLC monitored the reaction. After the reaction completed, POCl$_3$ was evaporated under reduced pressure. The residue was poured into crushed ice under stirring. The yellow solids were collected by filtration and purified by flash chromatography to give product M10 (0.66 g).

$^1$H-NMR (400 MHz, CDCl$_3$) δ 8.36 (s, 1H), 8.17 (s, 1H), 7.53 (d, J=8.8 Hz, 1H), 7.22 (d, J=8.4 Hz, 1H), 4.03 (s, 3H), 3.42 (m, 1H), 1.50 (d, J=6.0 Hz, 6H).

EXAMPLE 11

Intermediate 11 (M11)

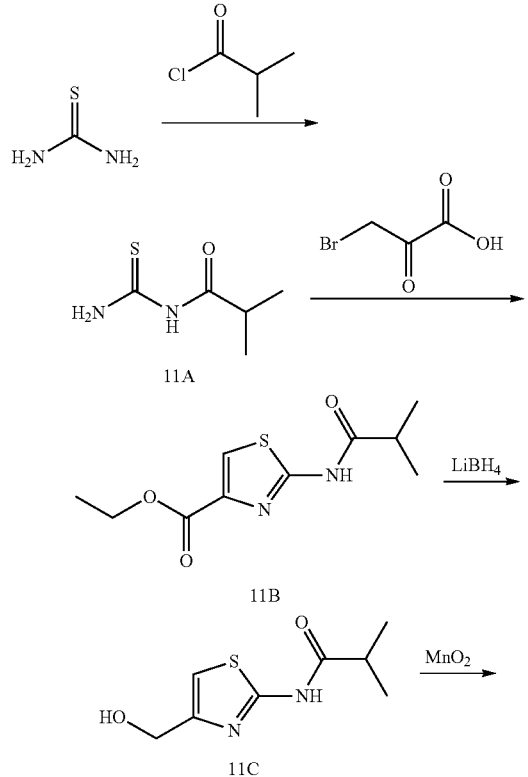

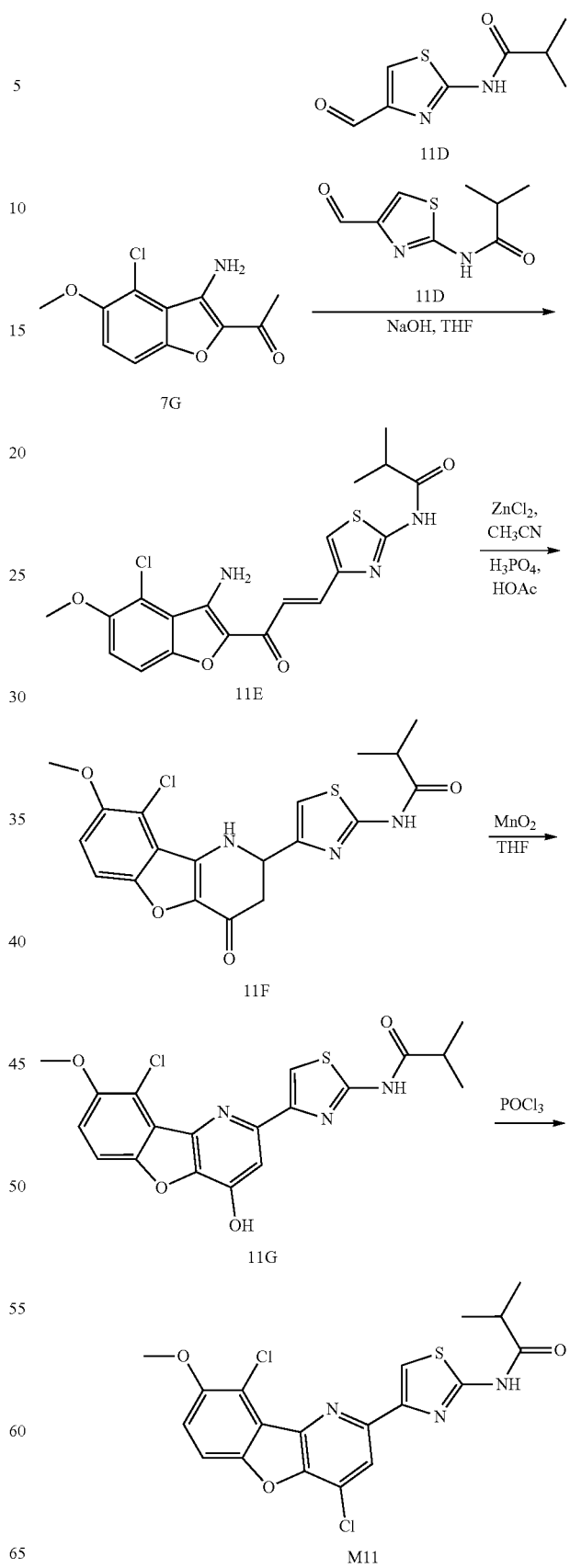

Step S₁₁ₐ: Synthesis of isobutyryl-thiourea (11A)

Thiourea (152 g, 2 mol) was dissolved in toluene (1520 mL). To the solution was added isobutyryl chloride (213 g, 2 mol) under mechanical stirring. The reaction mixture was refluxed for 3 hours. TLC monitored the reaction. After the reaction completed, the reaction mixture was cooled to room temperature and filtered to remove insoluble solids. The filtrate was concentrated to dryness. The yellow solids were collected by filtration, washed with petroleum ether (100 mL×3) to appear white, dried in vacumm to give the desired product 11A (90 g, 30% yield) as a white solid (mp: 114~116° C.).

$^1$H-NMR (CDCl$_3$): δ 1.24 (d, J=6.0 Hz, 2×3H), δ 2.68 (m, J=6.93 Hz, 1H).

Step S₁₁ᵦ: Synthesis of 2-isobutyrylamino-thiazole-4-carboxylic acid ethyl ester (11B)

11A (29.6 g, 0.2 mol) was dissolved in anhydrous EtOH (300 mL). To the solution was added 3-bromo-2-oxo-propionic acid (34 g, 0.17 mol). The mixture was refluxed for 2 hours, then cooled to room temperature, concentrated to dryness, dissolved with ethyl acetate, washed with saturated aqueous of NaHCO$_3$. The organic layer was dried and concentrated to give a crude product 11B (48 g, 100% yield).

$^1$H-NMR (CDCl$_3$): δ 1.356-1.373 (d, J=6.8 Hz, 2×3H), δ 2.828-2.845 (m, J=6.93 Hz, 1H), δ 8.094 (s, 1H), δ 10.026 (s, 1H), δ 11.605 (b, 1H).

Step S₁₁C: Synthesis of 2-isobutyrylamino-thiazole-4-methanol (11C)

11B (0.73 g, 3 mmol) was dissolved in THF (14 mL). To the solution was added LiBH$_4$ (0.23 g, 10 mmol) in batches at room temperature. The reaction mixture was refluxed overnight, then quenched with 14 mL of anhydrous MeOH and concentrated to dryness. The residue was dissolved in dichloromethane and filtered. The filtrate was concentrated and dried to give a crude product 11C (0.48 g, 100% yield).

$^1$H-NMR (CDCl$_3$): δ 1.32 (d, J=5.0 Hz, 2×3H), δ 2.58-2.73 (m, 1H), δ 4.68 (s, 2H), δ 6.82 (s, 1H).

Step S₁₁D: Synthesis of N-(4-formyl-thiazol-2-yl)-isobutyramide (11D)

11C (0.5 g, 2.5 mmol) was dissolved in THF (10 mL). To the solution at room temperature was added activated MnO$_2$ (1.74 g, 20 mmol). The reaction mixture was refluxed overnight, then filtered. The filtrate was concentrated and dried to give a crude product 11D (0.25 g, 50% yield).

$^1$H-NMR (CDCl$_3$): δ 1.32 (d, J=6.8 Hz, 6H), δ 2.58-2.73 (m, 1H), δ 7.88 (s, 1H), δ 9.88 (s, 1H), δ 10.24 (brs, 1H).

Step S₁₁E: Synthesis of N-{4-[3-(3-amino-4-chloro-5-methoxy-benzofuran-2-yl)-3-oxo-propenyl]-thiazol-2-yl}-isobutyramide (11E)

7G (2.5 g, 10.4 mmol) was dissolved in THF (25 mL). To the solution was added 11D (2.4 g, 1.2 eq, 12.5 mmol), followed by crushed NaOH powder (0.8 g, 2 eq, 20.8 mmol). The reaction mixture was stirred at room temperature for about 1 hour and the solution was getting darker. After reaction completed, the mixture was poured into ice-water under stirring. The solids were collected by filtration, dried and purified by column chromatography on silica gel to give 2.6 g of pure product 11E.

$^1$H-NMR (400 MHz, d-CDCl$_3$) δ 11.48 (brs, 1H), 7.64 (m, 2H), 7.26 (d, J=8.8 Hz, 1H), 7.23 (s, 1H), 7.18 (d, J=8.8 Hz, 1H), 6.41 (s, 2H), 3.96 (s, 3H), 2.78 (m, 1H), 1.31 (d, J=7.2 Hz, 6H).

Step S₁₁F: Synthesis of 9-chloro-2-(2-isobutyrylamino-thiazole-4-yl)-8-methoxy-2,3-dihydro-benzofuro[3,2-b]pyridin-4(1H)-one (11F)

To a mixture of 11E (2.6 g, 6.19 mmol) in MeCN (30 mL) was added ZnCl$_2$ (1.27 g, 1.5 eq, 9.3 mmol) at room temperature, followed by AcOH (30 mL) and H$_3$PO$_4$ (30 mL) The reaction mixture was stirred 80° C. overnight. After reaction completed, the mixture was cooled and poured into crushed ice under stirring, neutralized to pH=7~8, extracted with ethyl acetate, dried and concentrated to give 1.6 g of crude product, which was purified by column chromatography on silica gel to give 500 mg of pure product (11F).

$^1$H-NMR (400 MHz, DMSO-d$_6$) δ 12.15 (s, 1H), 7.55 (d, J=8.8 Hz, 1H), 7.45 (d, J=8.8 Hz, 1H), 7.134 (brs, 1H), 6.99 (s, 1H), 4.97 (m, 1H), 3.91 (s, 3H), 2.91 (m, 2H), 2.73 (m, 1H), 1.10 (d, J=7.2 Hz, 6H).

Step S₁₁G: Synthesis of 4-hydroxyl-9-chloro-2-(2-isobutyrylamino-thiazole-4-yl)-8-methoxy-benzofuro[3,2-b]pyridine (11G)

11F (500 mg, 1.19 mmol) was dissolved in THF (tetrahydrofuran, 30 mL). To the solution was added activated MnO$_2$ (600 mg, 6 eq, 6.9 mmol). The mixture was refluxed for 48 hours. After reaction completed, the mixture was cooled and filtered. The cake was washed well with THF and MeOH. The filtrate was concentrated and purified by column chromatography on silica gel to give 300 mg of pure product (11G).

$^1$H-NMR (400 MHz, DMSO-d$_6$) δ 12.26 (s, 1H), 7.82 (s, 1H), 7.74 (d, J=9.6 Hz, 1H), 7.66 (s, 1H), 7.46 (d, J=9.6 Hz, 1H), 3.97 (s, 3H), 2.81 (m, 1H), 1.16 (d, J=7.2 Hz, 6H).

Step S₁₁H: Synthesis of 4,9-dichloro-2-(2-isobutyrylamino-thiazole-4-yl)-8-methoxy-2,3-dihydro-benzofuro[3,2-b]pyridine (M11)

A mixture of 11G (300 mg, 0.72 mmol) in POCl$_3$ (5 mL) was refluxed for 30 min. After reaction completed, POCl$_3$ was evaporated under reduced pressure. The residue was poured into crushed ice and stirred for 10 min. The solids were collected by filtration and dried to give 161 mg of product (M11).

$^1$H-NMR (400 MHz, CDCl$_3$) δ 8.32 (s, 1H), 7.97 (s, 1H), 7.601 (d, J=8.8 Hz, 1H), 7.31 (d, J=8.8 Hz, 1H), 4.06 (s, 3H), 2.99 (m, 1H), 1.3 (d, J=7.2 Hz, 6H).

EXAMPLE 12

Synthesis of 12G

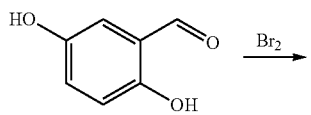

-continued

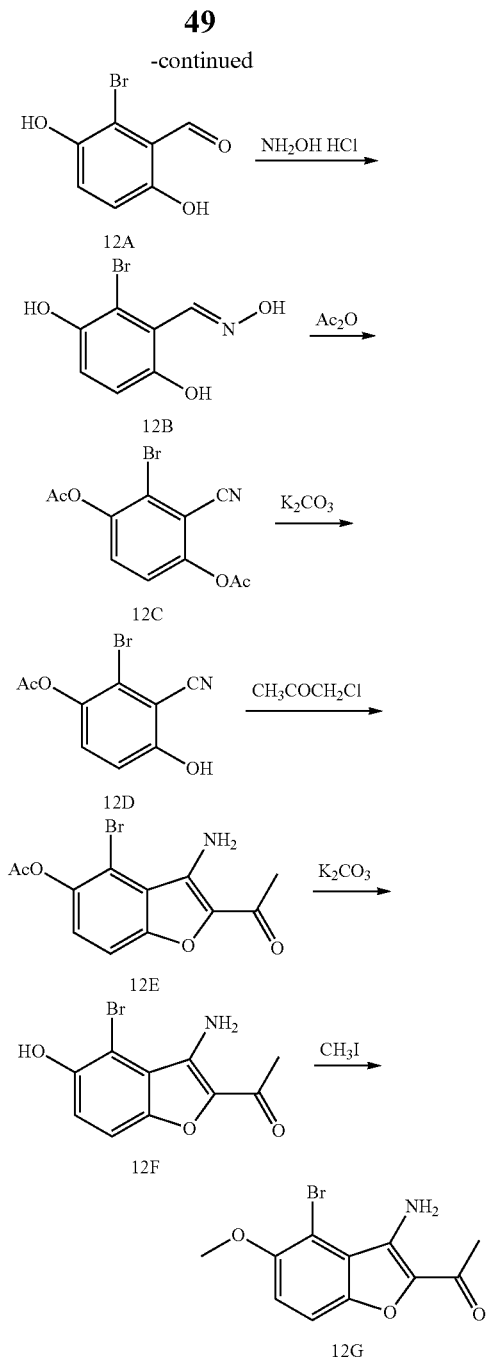

Step S$_{12A}$: Synthesis of 2-bromo-3,6-dihydroxy-benzaldehyde (12A)

2,5-dihydroxy-benzaldehyde (100 g, 0.72 mol) was dissolved in chlorform (1L).

To the solution was added Na$_3$PO$_4$ (77 g), followed by Br$_2$ (150 g, 0.94 mol) dropwise at room temperature. The mixture was stirred for 2.5 hours. To the reaction mixture was added aq.NH$_4$Cl. The precipitated solid was collected by filtration, then dissolved in ethyl acetate, washed with water. The organic layer was dried over anhydrous Na$_2$SO$_4$, concentrated and purified by column chromatography on silica gel to give product 12A (90 g, 57.2% yield).

Step S$_{12B}$: Synthesis of 2-bromo-3,6-dihydroxy-benzaldehyde oxime (12B)

To a mixture of 2-bromo-3,6-dihydroxy-benzaldehyde (12A) (50 g, 0.23 mol) and hydroxylamine hydrochloride (19.2 g, 0.28 mol) was added 95% EtOH (500 mL), followed by NaOH (13.8 g, 0.345 mol). The reaction mixture was stirred at room temperature for 2 hours, then extracted with ethyl acetate and concentrated to give 2-bromo-3,6-dihydroxy-benzaldehyde oxime (12B) (45 g, 84.1% yield) as a solid.

Step S$_{12C}$: Synthesis of 2-bromo-3-cyano-1,4-diacetoxylbenzene (12C)

A mixture of 12B (45 g, 0.193 mol) and sodium acetate (3 g) in Ac$_2$O (200 mL) was heated to reflux overnight. The reaction mixture was evaporated under reduced pressure to remove Ac$_2$O. The residue was poured into water and stirred for 1 hour. The precipitated solids were collected by filtration and dried to give 12C (40 g, 69.1% yield).

$^1$H-NMR (400 MHz, DMSO-d$_6$) δ 7.79 (d, J=9.2 Hz, 1H), 7.61 (d, J=9.2 Hz, 1H), 2.40 (s, 3H), 2.38 (s, 3H).

Step S$_{12D}$: Synthesis of 2-bromo-3-cyano-4-hydroxy-phenyl acetate (12D)

12C (15 g, 0.05 mol) was added to MeOH (52 ml) and dichloromethane (52 mL). To the mixture was added K$_2$CO$_3$ (7 g, 0.05 mol) in batches at room temperature. The reaction mixture was stirred overnight at room temperture, then neutralized with diluted hydrochloric acid to pH=6~7, extracted with dichloromethane, dried over anhydrous Na$_2$SO$_4$ and concentrated to give 12D (8 g, 62.1% yield).

$^1$H-NMR (400 MHz, DMSO-d$_6$) δ 11.75 (s, 1H), 7.44 (d, J=9.2 Hz, 1H), 7.06 (d, J=9.2 Hz, 1H), 2.31 (s, 3H).

Step S$_{12E}$: Synthesis of 2-acetyl-3-amino-4-bromo-5-acetoxyl-benzofuran (12E)

To a mixture of 12D (7 g, 0.027 mol) and 1-chloro-propan-2-one (3 mL) in DMF (30 mL) was added K$_2$CO$_3$ (4.1 g, 0.029 mol). The reaction mixture was stirred at 90° C. for 1 hour. TLC monitored the reaction. After the reaction completed, the reaction mixture was cooled to room temperature and added dropwise to ice-water. The precipitated solids were collected by filtration to give a crude product 12E (6.8 g, 79.6% yield).

$^1$H-NMR (400 MHz, DMSO-d$_6$) δ 7.65 (d, J=9.2 Hz, 1H), 7.48 (d, J=9.2 Hz, 1H), 6.49 (s, 2H), 2.41 (s, 3H), 2.36 (s, 3H).

Step S$_{12F}$: Synthesis of 2-acetyl-3-amino-4-bromo-5-hydroxy-benzofuran (12F)

To a mixture of 12E (6.8 g, 0.021 mol) in MeOH (40 mL) and water (20 mL) was added K$_2$CO$_3$ (4.5 g, 0.032 mol) in batches at room temperature. The reaction mixture was stirred at room temperature overnight, then neutralized with diluted hydrochloric acid to pH=6~7, extracted with ethyl acetate, dried and concentrated to give 12F (5.6 g, 95.1% yield).

Step S$_{12G}$: Synthesis of 2-acetyl-3-amino-4-bromo-5-methoxy-benzofuran (12G)

To a mixture of 12F (5.6 g, 0.020 mol) and CsF (9.5 g, 0.0625 mol) in THF (20 mL) was added MeI (2.9 g) dropwise at room temperature. The reaction mixture was stirred at room temperature for 1 hour, then added dropwise into water. The solids were precipitated out dissolved in ethyl acetate and purified by column chromatography on silica gel to give 12G (2.4 g, 40.7% yield).

$^1$H-NMR (400 MHz, CDCl$_3$) δ 7.58 (d, J=9.2 Hz, 1H), 7.41 (t, J=9.2 Hz, 1H), 6.41 (s, 2H), 3.89 (s, 3H), 2.38 (s, 3H).

EXAMPLE 13

Intermediate 13 (M13)

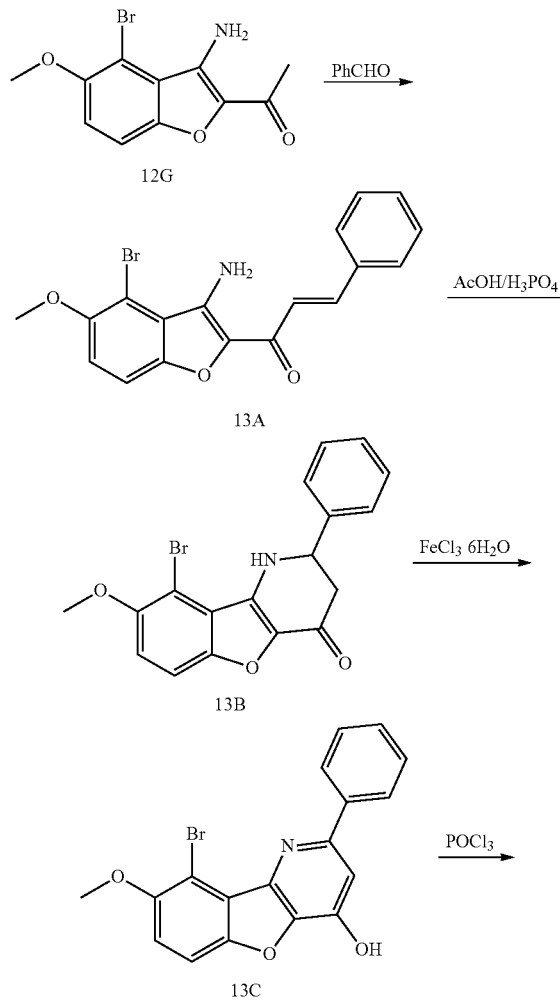

Step S$_{13A}$: Synthesis of 2-cinnamoyl-3-amino-4-bromo-5-methoxy-benzofuran (13A)

A mixture of 12G (2 g, 0.007 mol), benzaldehyde (1.6 g, 0.015 mol), NaOH (1.2 g) and formaldehyde (20 mL) was heated to 50° C. and reacted overnight, then added into water dropwise. The precipitated solids were collected by filtration to give 13A (2.6 g, 95% yield)

$^1$H-NMR (400 MHz, DMSO-d$_6$) δ 7.81 (m, 2H), 7.37 (d, J=15.6 Hz, 1H), 7.63 (d, J=8.8 Hz, 1H), 7.56 (d, J=16.0 Hz, 1H), 7.44-7.50 (m, 4H), 6.82 (s, 2H), 3.91 (s,3H).

Step S$_{13B}$: Synthesis of 9-bromo-8-methoxy-2-phenyl-2,3-dihydro-benzofuro[3,2-b]pyridin-4(1H)-one (13B)

A mixture of 13A (2.6 g, 0.0069 mol) in AcOH (10 mL) and H$_3$PO$_4$ (10 mL) was heated to 90° C. and reacted for 2 hours. TLC monitored the reaction. After the reaction completed, the reaction mixture was added dropwise into water. The precipitated solids were collected by filtration to give 13B (2 g, 76.9% yield).

$^1$H-NMR (400 MHz, DMSO-d$_6$) δ 7.61 (d, J=9.2 Hz, 1H), 7.50 (d, J=7.6 Hz, 1H), 7.43 (d, J=9.2 Hz, 1H), 7.33 (t, J=7.2 Hz, 2H), 6.83 (s, 1H), 4.99 (m, 1H), 3.91 (s, 3H), 2.75-2.87 (m, 2H).

Step S$_{13C}$: Synthesis of 4-hydroxyl-9-bromo-8-methoxy-2-phenyl-benzofuro[3,2-b]pyridine (13C)

A mixture of 13B (2.0 g, 0.0053 mol), FeCl$_3$.6H$_2$O (6 g) and 1,4-dioxane (20 mL) was heated to 110° C. and reacted overnight. After reaction completed, the reaction mixture was added dropwise into water. The precipitated solids were collected by filtration to give 13C (1.8 g, 90.4% yield).

$^1$H-NMR (400 MHz, DMSO-d$_6$) δ 11.79 (s, 1H), 8.17 (d, J=7.6 Hz, 2H), 7.08 (d, J=9.2 Hz, 1H), 7.51-7.54 (m, 3H), 7.42-7.46 (m, 2H), 3.95 (s, 3H).

Step S$_{13D}$: Synthesis of 9-bromo-4-chloro-8-methoxy-2-phenyl-benzofuro[3,2-b]pyridine (M13)

A mixture of 13C (1.8 g, 0.0048 mol) and POCl$_3$ (10 mL) was heated to 110° C. and reacted for 30 min. TLC monitored the reaction. After the reaction completed, POCl$_3$ in the mixture was evaporated. The residue was added dropwise into ice-water. The solids were collected by filtration and purified by a short column chromatography to give M13 (1.5 g, 79.3% yield).

$^1$H-NMR (400 MHz, CDCl$_3$) δ 8.23 (dd, J1=8.0 Hz, J2=1.6 Hz, 2H), 7.94 (s, 1H), 7.63 (d, J=8.4 Hz, 1H), 7.55 (dt, J1=7.6 Hz, J2=0.8 Hz, 2H), 7.49 (t, J=7.2 Hz, 1H), 7.23 (d, J=8.4 Hz, 1H), 4.04 (s, 3H).

EXAMPLE 14

Intermediate 14 (M14)

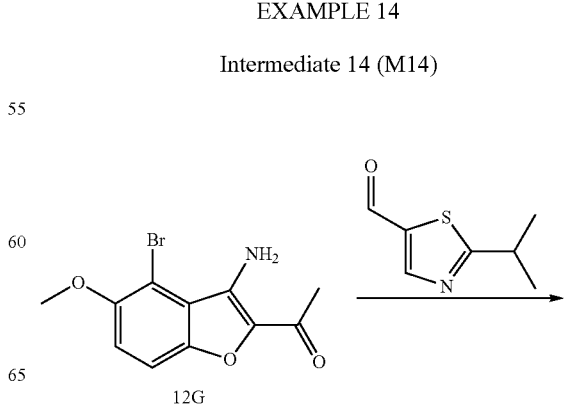

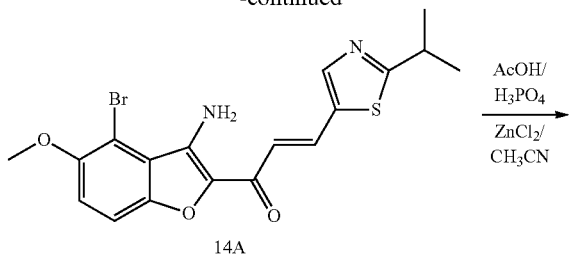

14A

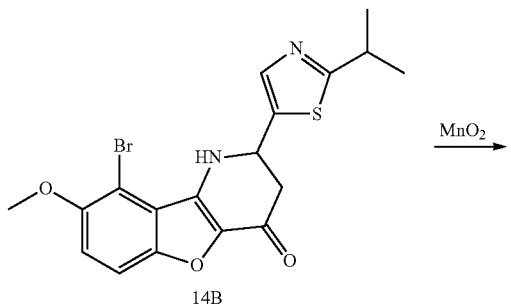

14B

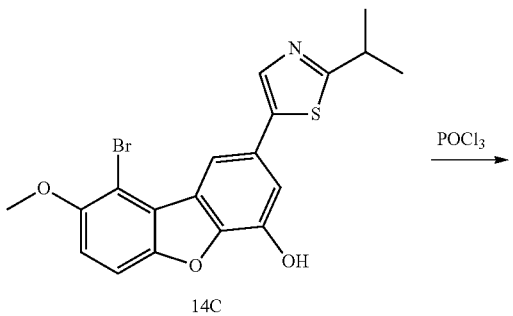

14C

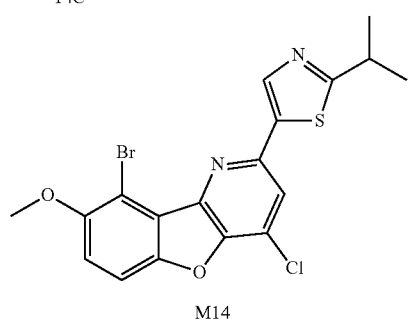

M14

Step S$_{14A}$: Synthesis of (E)-1-(3-amino-4-bromo-5-methoxy-benzofuran-2-yl)-3-(2-isopropyl-thiazol-5-yl)-2-propen-1-one (14A)

A mixture of 12G (1.5 g, 5.2 mmol), 2-isopropyl-thiazole-5-carbaldehyde (1.2 g, 7.7 mmol) in THF (20 mL) was cooled to 0° C. To the mixture was added NaOH (1.5 g), then stirred at room temperature overnight. TLC monitored the reaction. After the reaction completed, the reaction mixture was added dropwise into water. The precipitated solids were collected by filtration to give 14A (1.4 g, 62.9% yield).

Step S$_{14B}$: Synthesis of 9-bromo-2-(2-isopropyl-thiazol-5-yl)-8-methoxy-1,2-dihydro-benzofuro[3,2-b]pyridin-4-one (14B)

A mixture of 14A (1.4 g, 3.3 mmol), ZnCl$_2$ (6 g), MeCN (10 mL), AcOH (2 mL) and H$_3$PO$_4$ (2 mL) was heated to 90° C. and reacted overnight. TLC monitored the reaction. After the reaction completed, the reaction mixture was added dropwise into water, extracted with ethyl acetate and concentrated to give 14B (1.1 g, 78% yield).

Step S$_{14C}$: Synthesis of 4-hydroxyl-9-bromo-2-(2-isopropyl-thiazol-5-yl)-8-methoxy-dibenzofuran (14C)

A mixture of 14B (1.1 g, 2.6 mmol), MnO$_2$ (6 g) in THF (20 mL) was heated to 110° C. and reacted overnight, then filtered. The filtrate was concentrated to give 14C (0.8 g, 73% yield).

Step S$_{14D}$: Synthesis of 9-bromo-4-chloro-2-(2-isopropyl-thiazol-5-yl)-8-methoxy-benzofuro[3,2-b]pyridine (M14)

A mixture of 14C (0.8 g, 1.9 mmol) in POCl$_3$ (10 mL) was heated to 110° C. and reacted for 30 min. TLC monitored the reaction. After the reaction completed, POCl$_3$ in reaction mixture was evaporated. The residue was added dropwise into ice-water. The precipitated solids were collected by filtration and purified by short column chromatography to give M14 (0.16 g, 19% yield).

$^1$H-NMR (400 MHz, CDCl$_3$) δ 8.19 (s, 1H), 7.81 (s, 1H), 7.63 (d, J=8.4 Hz, 1H), 7.25 (d, J=8.4 Hz, 1H), 4.04 (s, 3H), 3.40 (m, 1H), 1.52 (d, J=7.2 Hz, 6H).

EXAMPLE 15

Intermediate 15 (M15)

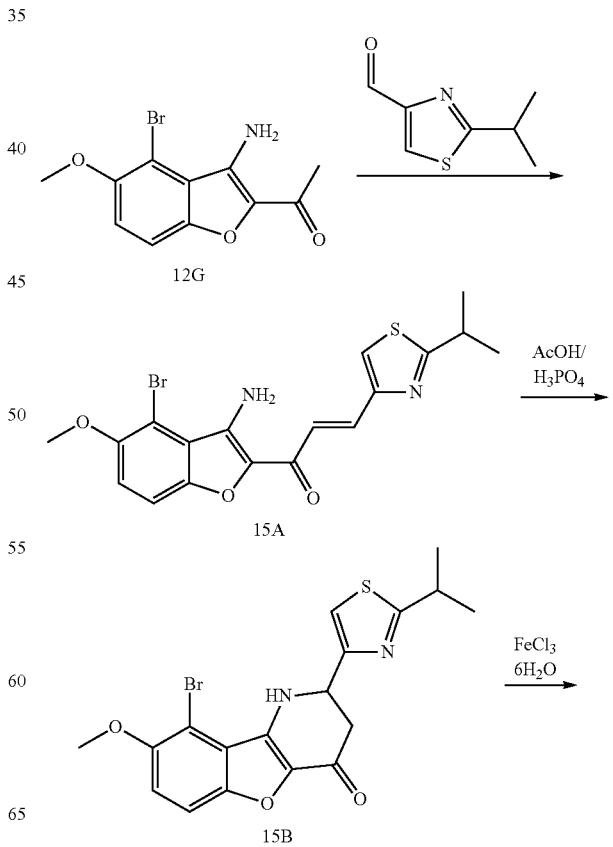

-continued

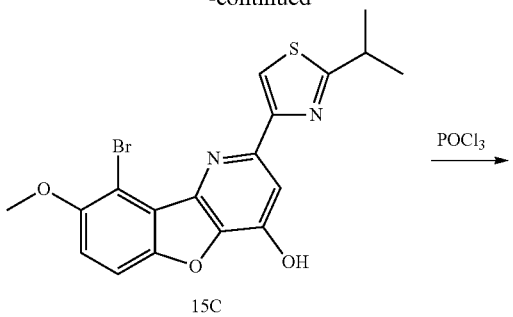

15C

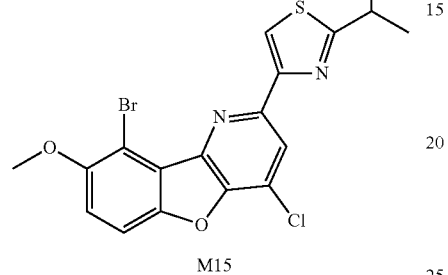

M15

Step $S_{15A}$: Synthesis of 1-(3-amino-4-bromo-5-methoxy-benzofuran-2-yl)-3-(2-isopropyl-thiazol-4-yl)-2-propen-1-one (15A)

A mixture of 12G (2 g, 7 mmol), 2-isopropyl-thiazole-4-carbaldehyde (2.2 g, 14.6 mmol), NaOH (1.5 g) and MeOH (20 mL) was heated to 50° C. and reacted overnight. TLC monitored the reaction. After the reaction completed, the reaction mixture was added dropwise into water. The precipitated solids were collected by filtration to give 15A (2.8 g, 94.4% yield).

$^1$H-NMR (400 MHz, DMSO-$d_6$) δ 8.04 (s, 1H), 7.67 (d, J=9.2 Hz, 1H), 7.63 (s, 2H), 7.45 (d, J=9.2 Hz, 1H), 6.81 (s, 2H), 3.90 (s, 3H), 3.38 (m, 1H), 1.38 (d, J=6.4 Hz, 6H).

Step $S_{15B}$: Synthesis of 9-bromo-2-(2-isopropyl-thiazol-4-yl)-8-methoxy-2,3-dihydro-benzofuro[3,2-b]pyridin-4(1H)-one (15B)

A mixture of 15A (2.8 g, 6.6 mmol), AcOH (10 mL) and $H_3PO_4$ (10 mL) was heated to 90° C. and reacted for 2 hours. TLC monitored the reaction. After the reaction completed, the reaction mixture was added dropwise into water. The precipitated solids were collected by filtration to give 15B (2 g, 71.4% yield).

Step $S_{15C}$: Synthesis of 4-hydroxyl-9-bromo-2-(2-isopropyl-thiazol-4-yl)-8-methoxy-benzofuro[3,2-b]pyridine (15C)

A mixture of 15B (2.0 g, 4.7 mmol), $FeCl_3 \cdot 6H_2O$ (6 g) in 1,4-dioxane (20 mL) was heated to 110° C. and reacted overnight. TLC monitored the reaction. After the reaction completed, the reaction mixture was added dropwise into water. The precipitated solids were collected by filtration to give 15C (1.2 g, 60.2% yield).

$^1$H-NMR (400 MHz, DMSO-$d_6$) δ 8.04 (s, 1H), 7.67 (d, J=9.2 Hz, 1H), 7.63 (s, 2H), 7.45 (d, J=9.2 Hz, 1H), 6.81 (s, 2H), 3.91 (s, 3H), 3.38 (m, 1H), 1.42 (d, J=6.4 Hz, 6H).

Step $S_{15D}$: Synthesis of 9-bromo-4-chloro-2-(2-isopropyl-thiazol-4-yl)-8-methoxy-benzofuro[3,2-b]pyridine (M15)

A mixture of 15C (1.2 g, 2.8 mmol) in $POCl_3$ (10 mL) was heated to 110° C. and reacted for 30 min. TLC monitored the reaction. After the reaction completed, $POCl_3$ in the reaction mixture was evaporated. The residue was added dropwise into ice-water. The precipitated solids were collected by filtration and purified by short column chromatography to give M15 (0.2 g, 16% yield).

$^1$H-NMR (400 MHz, $CDCl_3$) δ 8.39 (s, 1H), 8.20 (s, 1H), 7.62 (d, J=8.8 Hz, 1H), 7.24 (d, J=9.2 Hz, 1H), 4.04 (s, 3H), 3.40 (m, 1H), 1.50 (d, J=7.2 Hz, 6H).

EXAMPLE 16

Intermediate 16 (M16)

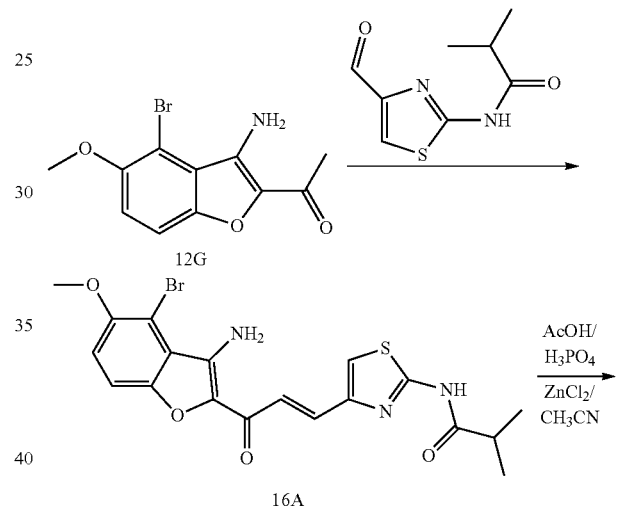

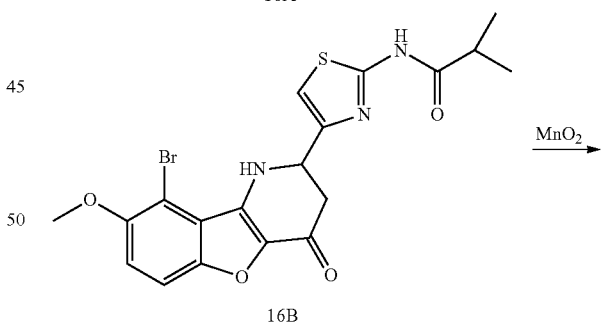

16B

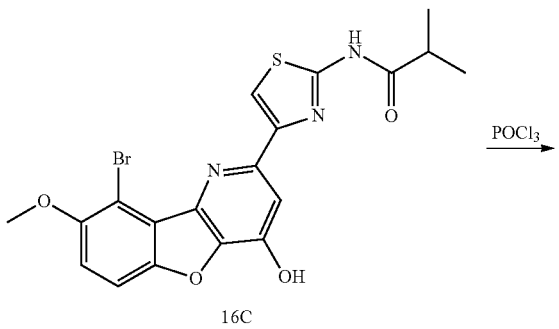

16C

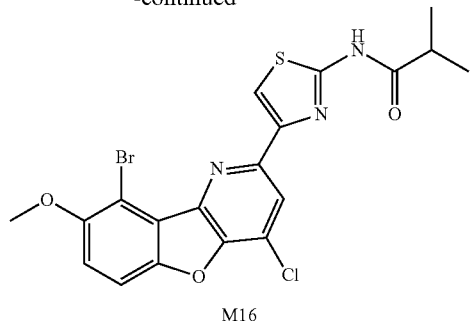

M16

Step S16A: Synthesis of 1-(3-amino-4-bromo-5-methoxy-benzofuran-2-yl)-3-(2-isobutyrylamino-thiazole-4-yl)-2-propen-1-one (16A)

A mixture of 12G (2 g, 7 mmol), 11D (2.8 g, 14.5 mmol) in THF (20 mL) was cooled to 0° C. To the mixture was added NaOH (2 g). The reaction mixture was reacted at room temperature overnight. TLC monitored the reaction. After reaction completed, the reaction mixture was added dropwise into water. The precipitated solids were collected by filtration to give 16A (2 g, 61% yield).

$^1$H-NMR (400 MHz, CDCl$_3$) δ 9.80 (s, 1H), 7.65 (s, 1H), 7.35 (d, J=9.2 Hz, 1H), 7.23 (s, 1H), 7.16 (d, J=9.2 Hz, 1H), 6.52 (s, 2H), 3.96 (s, 3H), 2.73 (m, 1H), 1.38 (d, J=7.2 Hz, 6H).

Step S16B: Synthesis of 9-bromo-2-(2-isobutyrylamino-thiazole-4-yl)-8-methoxy-2,3-dihydro-benzofuro[3,2-b]pyridin-4(1H)-one (16B)

A mixture of 16A (2 g, 4.3 mmol), ZnCl$_2$ (6 g), MeCN (10 mL), AcOH (2 mL) and H$_3$PO$_4$ (2 mL) was heated to 90° C. and reacted overnight. TLC monitored the reaction. After the reaction completed, the reaction mixture was added dropwise into water, extracted with ethyl acetate and concentrated to give 16B (1.1 g, 55% yield).

$^1$H-NMR (400 MHz, DMSO-d$_6$) δ 10.21 (s, 1H), 7.43 (d, J=9.2 Hz, 1H), 7.17 (d, J=9.2 Hz, 1H), 6.92 (s, 1H), 5.99 (m, 1H), 5.03 (m, 1H), 3.96 (s, 3H), 2.93-3.09 (m, 2H), 2.69-2.74 (m, 1H), 1.33 (d, J=7.2 Hz, 6H).

Step S16C: Synthesis of 4-hydroxyl-9-bromo-2-(2-isobutyrylamino-thiazole-4-yl)-8-methoxy-benzofuro[3,2-b]pyridine (16C)

A mixture of 16B (1.1 g, 2.3 mmol) and MnO$_2$ (6 g) in THF (20 mL) was heated to 110° C. and reacted overnight. TLC monitored the reaction. After the reaction completed, the reaction mixture was filtered and the filtrate was concentrated to give 16C (0.7 g, 63.9% yield).

Step S16D: Synthesis of 9-bromo-4-chloro-2-(2-isobutyrylamino-thiazole-4-yl)-8-methoxy-benzofuro[3,2-b]pyridine (M16)

A mixture of 16C (0.7 g, 1.5 mmol) in POCl$_3$ (10 mL) was heated to 110° C. and reacted for 30 min. TLC monitored the reaction. After the reaction completed, POCl$_3$ in the reaction mixture was evaporated. The residue was added dropwise into ice-water. The precipitated solids were collected by filtration and purified by short column chromatography to give M16 (0.2 g, 27% yield).

$^1$H-NMR (400 MHz, CDCl$_3$) δ 9.37 (s, 1H), 8.17 (s, 1H), 8.00 (s, 1H), 7.63 (d, J=9.2 Hz, 1H), 7.24 (d, J=9.2 Hz, 1H), 4.04 (s, 3H), 2.72 (m, 1H), 1.50 (d, J=7.2 Hz, 6H).

EXAMPLE 17

Intermediate 17 (M17)

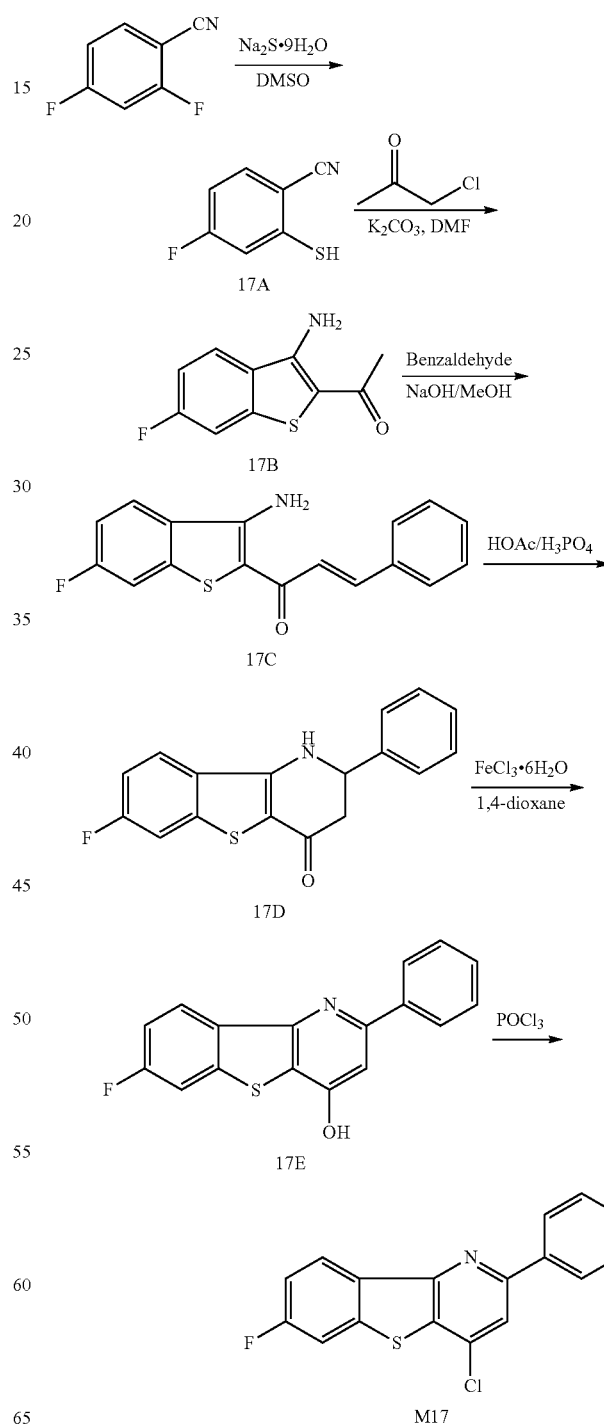

Step S$_{17A}$: Synthesis of 2-mercapto-4-fluoro-benzonitrile (17A)

The procedure was similar to step S$_{3A}$, while the starting material was 2,4-difluoro-benzonitrile in stead of 2-fluoro-benzonitrile.

Step S$_{17B}$: Synthesis of 1-(3-amino-6-fluoro-benzo[b]thiophen-2-yl)-ethanone (17B)

The procedure was similar to step S$_{3B}$, while the starting material was 17A in stead of 3A.

Step S$_{17C}$: Synthesis of (E)-2-cinnamoyl-3-amino-6-fluoro-benzo[b]thiophene (17C)

The procedure was similar to step S$_{3C}$, while the starting material was 17B in stead of 3B.

Step S$_{17D}$: Synthesis of 2-phenyl-7-fluoro-2,3-dihydro-benzothieno[3,2-b]pyridin-4(1H)-one (17D)

The procedure was similar to step S$_{3D}$, while the starting material was 17C in stead of 3C.

Step S$_{17E}$: Synthesis of 2-phenyl-7-fluoro-4-hydroxyl-benzothieno[3,2-b]pyridine (17E)

The procedure was similar to step S$_{3E}$, while the starting material was 17D in stead of 3D.
17E: MS (ESI): M$^+$+1=296.

Step S$_{17F}$: Synthesis of 4-chloro-7-fluoro-2-phenyl-benzothieno[3,2-b]pyridine (M17)

The procedure was similar to step S$_{3F}$, while the starting material was 17E in stead of 3E.
M17: MS (ESI): M$^+$+1=314.

EXAMPLE 18

Synthesis of 4-chloro-2-methoxycarbonyl-phenyl acetic acid methyl ester (18E)

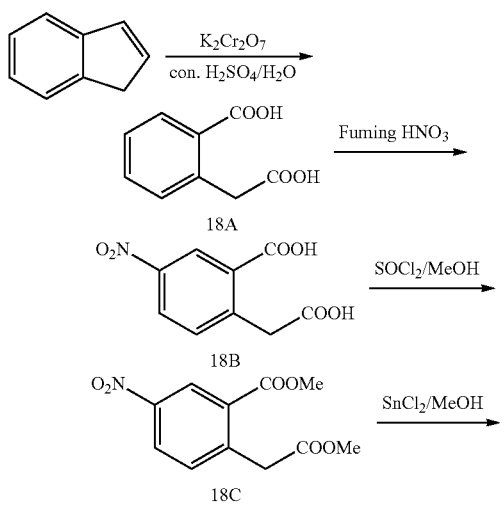

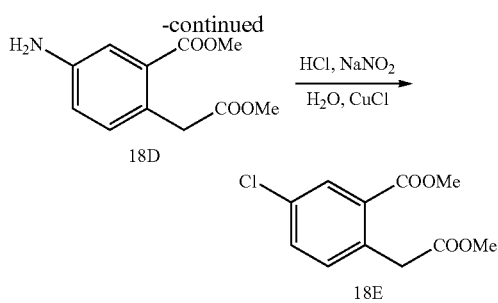

Step S$_{18A}$: Synthesis of 2-carboxyl-phenyl acetic acid (18A)

K$_2$Cr$_2$O$_7$ (24.4 g, 83 mmol) was dissolved in water (360 mL). To the solution was added conc. H$_2$SO$_4$ (133 g, 1.3 mol) dropwise slowly at 65° C., followed by 1H-indene (6.85 g, 56 mmol) dropwise. The reaction mixture was stirred at this temperture for 2 hours. The color of the solution changed from orange to blue, some solids were precipitated out on the bottle wall. The reaction mixture was cooled to below 0° C., and stirred for 2 hours, then filtered. The cake was washed with 1% aq.H$_2$SO$_4$ and ice-water until the green color disappeared, then dried to give 7.6 g of 2-carboxyl-phenyl acetic acid (18A).
MS (ESI): M$^+$+1=181.1.

Step S$_{18B}$: Synthesis of 2-carboxymethyl-5-nitro-benzoic acid (18B)

2-carboxyl-phenyl acetic acid (3 g, 16.7 mmol) was added in batches to fuming HNO$_3$ (16 mL) under ice-salt bath while keeping the temperature under −3° C. The reaction mixture was reacted at that temperature for 2 hours. TLC monitored the reaction. After the reaction completed, the reaction mixture was added into ice (16 g) under stirring. The precipitated white solids were collected by filtration and dried to give 2.1 g of the desired product 2-carboxymethyl-5-nitro-benzoic acid (18B).
$^1$H-NMR (DMSO-d$_6$): δ (ppm): 8.62 (d, J=2.8 Hz, 1H), 8.35-8.37 (dd, J1=8.8 Hz, J2=2.4 Hz, 1H), 7.68 (d, J=8.8 Hz, 1H), 4.11 (s, 2H); MS (ESI): M$^+$+1=226.1.

Step S$_{18C}$: Synthesis of 2-methoxycarbonylmethyl-5-nitro-benzoic acid methyl ester (18C)

2-carboxymethyl-5-nitro-benzoic acid (2 g, 8.8 mmol) was dissolved in MeOH (30 mL). To the solution was added SOCl$_2$ (2.64 g, 22.2 mmol) dropwise slowly at room temperature. The reaction mixture was refluxed for 2 hours. TLC monitored the reaction. After the reaction completed, the solvent in the reaction mixture was evaporated to dryness, which was used for the next step directly.

Step S$_{18D}$: Synthesis of 2-methoxycarbonylmethyl-5-amino-benzoic acid methyl ester (18D)

2-methoxycarbonylmethyl-5-nitro-benzoic acid methyl ester (2.2 g, 8.8 mmol) was dissolved in MeOH (30 mL), then heated to 50° C. To the solution was added SnCl$_2$ (5.89 g, 31 mmol) in batches. The reaction mixture was stirred at this temperature for 1 day. TLC monitored the reaction. After the reaction completed, the solvent was evaporated. To the residue was added ethyl acetate and base, adjusted pH to 8~9, then filtered though celite and washed with ethyl acetate. The organic layer of the filtrate was collected and washed with water, dried over anhydrous $Na_2SO_4$ and concentrated to give 1.3 g of 5-amino-2-methoxycarbonylmethyl-benzoic acid methyl ester (18D).

$^1$H-NMR (DMSO-$d_6$): δ (ppm): 7.15 (d, J=2.8 Hz, 1H), 6.88 (d, J=8.0 Hz, 1H), 6.72 (dd, J1=8 Hz, J2=2.8 Hz, 1H), 5.30 (s, 1H), 3.75 (s, 2H), 3.73 (s, 3H), 3.56 (s, 3H); MS (ESI): $M^+$+1=224.2.

Step $S_{18E}$: Synthesis of 4-chloro-2-methoxycarbonyl-phenyl acetic acid methyl ester (18E)

5-amino-2-methoxycarbonylmethyl-benzoic acid methyl ester (5 g, 22.4 mmol) was dissolved in hydrochloric acid (50 mL). To the solution was added dropwise aq.$NaNO_2$ (1.7 g, 24.6 mmol) at below 5° C. After addition completed, the color became maroon. Then CuCl (2.4 g, 24.6 mmol) solution was added to the reaction mixture. The reaction mixture was reacted at below 5° C. for 1 hour. The reaction mixture was extracted with dichloromethane. The organic layer was washed with water, dried over anhydrous $Na_2SO_4$, concentrated and purified by column chromatography on silica gel (petroleum ether/ethyl acetate=10/1) to give 2.3 g of 5-chloro-2-methoxycarbonylmethyl-benzoic acid methyl ester (18E).

$^1$H-NMR (DMSO-$d_6$): δ (ppm): 7.88 (d, J=2.8 Hz, 1H), 7.64-7.66 (dd, J1=8 Hz, J2=2 Hz, 1H), 7.45 (d, J=8.4 Hz, 1H), 4.00 (d, J=4.0 Hz, 2H), 3.80 (s, 3H), 3.60 (s, 3H); MS (ESI): $M^+$+1=243.7.

EXAMPLE 19

Intermediate 19 (M19)

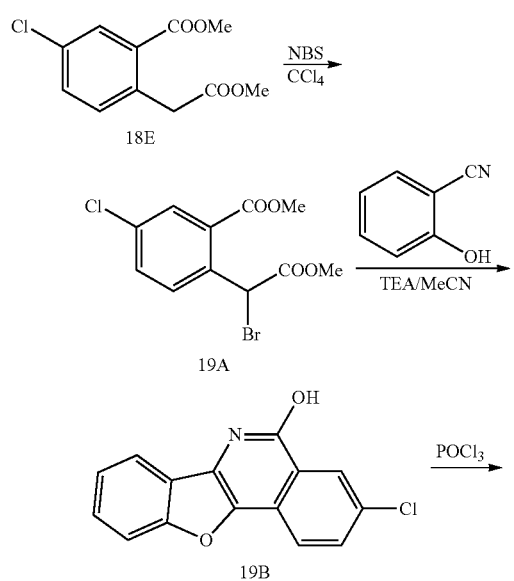

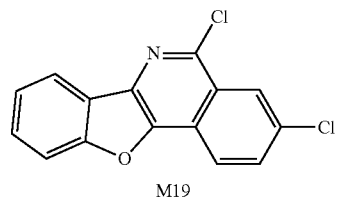

Step $S_{19A}$: Synthesis of 2-(4-chloro-2-methoxycarbonyl-phenyl)-2-bromo-acetic acid methyl ester (19A)

18E (16.48 mmol) was dissolved in $CCl_4$ (50 mL), and was added NBS (N-bromosuccinimide, 3.23 g, 18.13 mmol), followed by catalytic amount of BPO (benzoyl peroxide). The reaction mixture was refluxed for about 20 hours under stirring. When no more product was produced any more, the reaction mixture was cooled and filtered. To the filtrate was added NBS (1.6 g, 8.24 mmol) and catalytic amount of BPO. The reaction mixture was refluxed for additional 10 hours. After the reaction completed, the mixture was cooled and filtered. The filtrate was concentrated to give 6.4 g of a crude product (19A), which was used directly for the next step.

Step $S_{19B}$: Synthesis of 3-chloro-benzofuro[3,2-c]isoquinoline-5-ol (19B)

A mixture of 19A (crude, 20.29 mmol) and 2-hydroxybenzonitrile (20.29 mmol) in MeCN (100 mL) was stirred at room temperature. To the solution was added triethylamine (TEA, 20.44 g, 202.9 mmol) dropwise. After addition completed, the reaction was refluxed for 24 hours, then cooled. The precipitated solids were collected by filtration, washed with a small amount of MeCN, then washed with water several times until there was no TEA salt, dried to give pure product 19B (3.1 g).

$^1$H-NMR (DMSO-$d_6$): δ (ppm): 12.63 (s, 1H), 8.28 (d, J=2.4 Hz, 1H), 8.04-8.07 (m, 2H), 7.95 (dd, J1=8.8 Hz, J2=2.4 Hz, 1H), 7.78 (d, J=8.8 Hz, 1H), 7.52 (t, J=7.8 Hz, 1H), 7.42 (t, J=7.6 Hz, 1H); MS (ESI): $M^+$+1=270.7.

Step $S_{19C}$: Synthesis of 3,5-dichloro-benzofuro[3,2-c]isoquinoline (M19)

A mixture of 19B (11.8 mmol) in $POCl_3$ (20 mL) was refluxed for 2 hours. After reaction completed, $POCl_3$ was evaporated under reduced pressure. The residue was added into crushed ice and stirred for 10 min. The solids were collected by filtration and dried to give 3.2 g of a crude product, which was dissolved in dichloromethane and purified by flash chromatography (petroleum ether 1:1) and concentrated to give a pure product M19 (3.1 g).

$^1$H-NMR (DMSO-$d_6$): δ (ppm): 8.50 (d, J=8.8 Hz, 1H), 8.44 (s, 1H), 8.20 (d, J=7.6 Hz, 1H), 8.13 (dd, J1=9.2 Hz, J2=2.0 Hz, 1H), 7.95 (d, J=8.4 Hz, 1H), 7.69 (t, J=7.4 Hz, 1H), 7.59 (t, J=7.4 Hz, 1H); MS (ESI): $M^+$+1=289.1.

EXAMPLE 20

Intermediate 20 (M20)

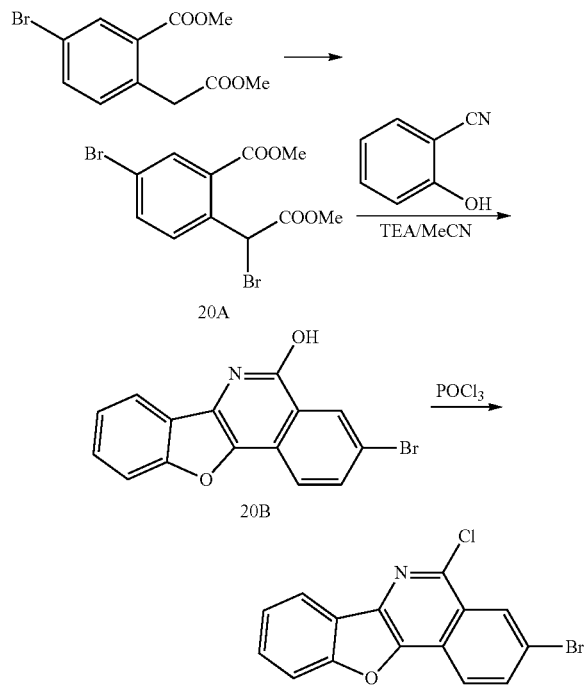

Step $S_{20A}$: Synthesis of 2-(4-bromo-2-methoxycarbonyl-phenyl)-2-bromo-acetic acid methyl ester (20A)

The procedure was similar to step $S_{19A}$, while the starting material was 5-bromo-2-methoxycarbonylmethyl-benzoic acid methyl ester (the procedure of this compound was similar to 5-chloro-2-methoxycarbonylmethyl-benzoic acid methyl ester, while the starting material was CuBr in stead of CuCl) in stead of 5-chloro-2-methoxycarbonyl methyl-benzoic acid methyl ester.
MS (ESI): M$^+$+1=367.

Step $S_{20B}$: Synthesis of 5-hydroxyl-3-bromo-benzofuro[3,2-c]isoquinoline (20B)

The procedure was similar to step $S_{19B}$, while the starting material was 20A in stead of 19A.
$^1$H-NMR (DMSO-d$_6$): δ (ppm): 12.63 (s, 1H), 8.41 (d, J=1.6 Hz, 1H), 8.05 (d, J=8.0 Hz, 2H), 7.98 (d, J=8.0 Hz, 1H), 7.77 (d, J=8.4 Hz, 1H), 7.50-7.54 (t, J=7.6 Hz, 1H), 7.40-7.44 (t, J=7.6 Hz, 1H); MS (ESI): M$^+$+1=315.1.

Step $S_{20C}$: Synthesis of 3-bromo-5-chloro-benzofuro[3,2-c]isoquinoline (M20)

The procedure was similar to step $S_{19C}$, while the starting material was 20B in stead of 19B.
$^1$H-NMR (DMSO-d$_6$): δ (ppm): 8.59 (d, J=1.6 Hz, 1H), 8.42 (d, J=8.8 Hz, 1H), 8.19-8.24 (m, 2H), 7.95 (d, J=8.0 Hz, 1H), 7.60 (dt, J=1.2, 7.6 Hz, 1H), 7.59 (t, J=7.6 Hz, 1H); MS (ESI): M$^+$+1=333.6.

EXAMPLE 21

Intermediate 21 (M21)

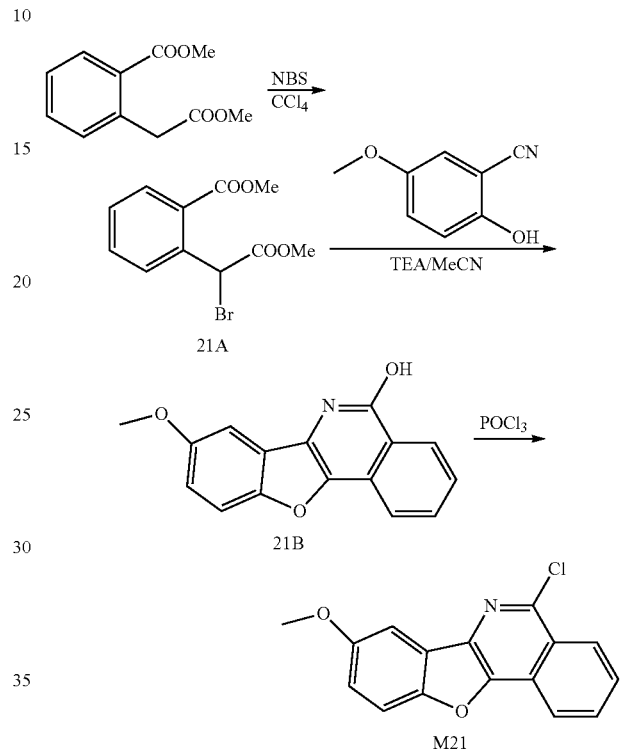

Step $S_{21A}$: Synthesis of 2-(2-methoxycarbonyl-phenyl)-2-bromo-acetic acid methyl ester (21A)

The procedure was similar to step $S_{19A}$, while the starting material was 2-methoxycarbonylmethyl-benzoic acid methyl ester (commercialized) in stead of 5-chloro-2-methoxycarbonyl methyl-benzoic acid methyl ester (18E).
MS (ESI): M$^+$+1=288.1.

Step $S_{21B}$: Synthesis of 5-hydroxyl-8-methoxy-benzofuro[3,2-c]isoquinoline (21B)

The procedure was similar to step $S_{19B}$, while the starting material 19A and 2-hydroxy-benzonitrile were replaced with 21A and 2-hydroxy-5-methoxy-benzonitrile, respectively.
$^1$H-NMR (DMSO-d$_6$): δ (ppm): 12.32 (s, 1H), 8.34 (d, J=8.0 Hz, 1H), 8.01 (d, J=8.4 Hz, 1H), 7.88 (t, J=8.4 Hz, 1H), 7.67 (d, J=9.2 Hz, 1H), 7.59-7.62 (m, 2H), 7.09 (dd, J1=9.2 Hz, J2=2.4 Hz, 1H), 3.83 (s, 3H); MS (ESI): M$^+$+1=266.3.

Step $S_{21C}$: Synthesis of 8-methoxy-5-chloro-benzofuro[3,2-c]isoquinoline (M21)

The procedure was similar to step $S_{19C}$, while the starting material was 21B in stead of 19B.

$^1$H-NMR (DMSO-d$_6$): δ (ppm): 8.50 (t, J=9.0 Hz, 2H), 8.12 (t, J=8.0 Hz, 1H), 7.96 (t, J=8.0 Hz, 1H), 7.86 (d, J=9.2 Hz, 1H), 7.68 (d, J=2.4 Hz, 1H), 7.25 (dd, J1=9.2 Hz, J2=2.8 Hz, 1H), 3.93 (s, 3H); MS (ESI): M$^+$+1=284.7.

EXAMPLE 22

Intermediate 22 (M22)

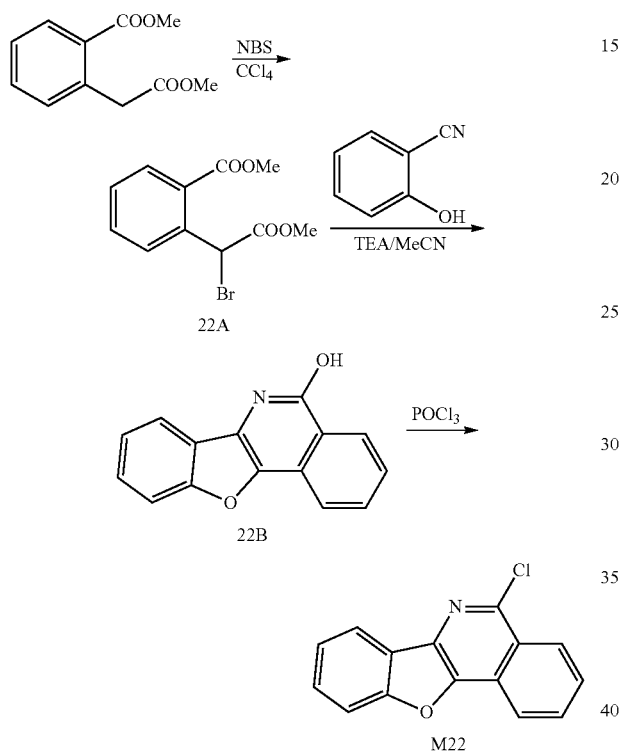

Step S$_{22A}$: Synthesis of 2-(2-methoxycarbonyl-phenyl)-2-bromo-acetic acid methyl ester (22A)

The procedure was similar to step S$_{19A}$, while the starting material was 2-methoxycarbonylmethyl-benzoic acid methyl ester (commercialized) in stead of 5-chloro-2-methoxycarbonyl methyl-benzoic acid methyl ester (18E).

Step S$_{22B}$: Synthesis of 5-hydroxyl-benzofuro[3,2-c]isoquinoline 1 (22B)

The procedure was similar to step S$_{19B}$, while the starting material was 22A in stead of 19A.

Step S$_{22C}$: Synthesis of 5-chloro-benzofuro[3,2-c]isoquinoline (M22)

The procedure was similar to step S$_{19C}$, while the starting material was 22B in stead of 19B.

$^1$H-NMR (DMSO-d$_6$): δ (ppm): 8.48 (d, J=6.4 Hz, 2H), 8.20 (d, J=7.2 Hz, 1H), 8.12 (t, J=7.6 Hz, 1H), 7.90-7.95 (m, 2H), 7.68 (t, J=7.8 Hz, 1H), 7.58 (t, J=7.2 Hz, 1H), MS (ESI): M$^+$+1=254.7.

EXAMPLE 23

Intermediate 23 (M23)

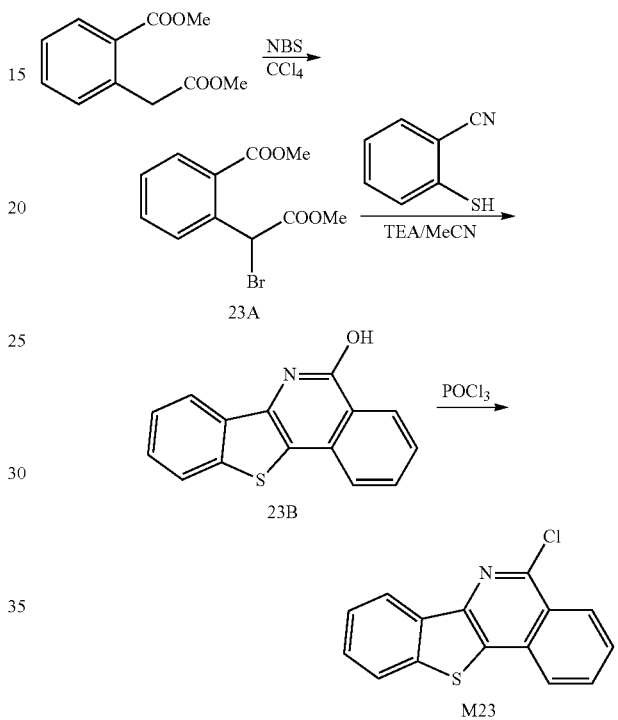

Step S$_{23A}$: Synthesis of 2-(2-methoxycarbonyl-phenyl)-2-bromo-acetic acid methyl ester (23A)

The procedure was similar to step S$_{19A}$, while the starting material was 2-methoxycarbonylmethyl-benzoic acid methyl ester (commercialized) in stead of 5-chloro-2-methoxycarbonyl methyl-benzoic acid methyl ester (18E).

Step S$_{23B}$: Synthesis of 5-hydroxyl-benzothieno[3,2-c]isoquinoline (23B)

The procedure was similar to step S$_{19B}$, while the starting material was 23A in stead of 19A, and used 2-mercapto-benzonitrile in stead of 2-hydroxy-benzonitrile.

Step S$_{23C}$: Synthesis of 5-chloro-benzothieno[3,2-c]isoquinoline (M23)

The procedure was similar to step S$_{19C}$, while the starting material was 23B in stead of 19B.

$^1$H-NMR (DMSO-d$_6$): δ (ppm): 8.51 (d, J=8.4 Hz, 1H), 8.41 (m, 1H), 8.31 (dd, J1=7.2 Hz, J2=0.8 Hz, 1H), 8.24 (m, 1H), 8.09 (t, J=8.0 Hz, 1H), 7.96 (t, J=8.0 Hz, 1H), 7.65-7.68 (m, 2H); MS (ESI): M$^+$+1=270.7.

EXAMPLE 24

Intermediate 24 (M24)

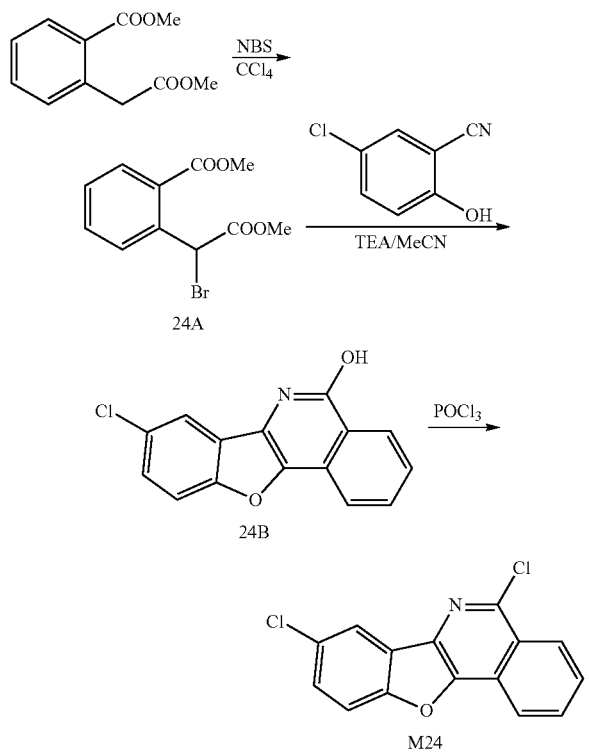

Step $S_{24A}$: Synthesis of 2-(2-methoxycarbonyl-phenyl)-2-bromo-acetic acid methyl ester (24A)

The procedure was similar to step $S_{19A}$, while the starting material was 2-methoxycarbonylmethyl-benzoic acid methyl ester in stead of 5-chloro-2-methoxycarbonyl methyl-benzoic acid methyl ester (18E).

Step $S_{24B}$: Synthesis of 5-hydroxyl-8-chloro-benzofuro[3,2-c]isoquinoline (24B)

The procedure was similar to step $S_{19B}$, while the starting material was 24A in stead of 19A, and used 5-chloro-2-hydroxy-benzonitrile in stead of 2-hydroxy-benzonitrile.

Step $S_{24C}$: Synthesis of 5,8-dichloro-benzofuro[3,2-c]isoquinoline (M24)

The procedure was similar to step $S_{19C}$, while the starting material was 24B in stead of 19B.

$^1$H-NMR (DMSO-d$_6$): δ (ppm): 8.51 (t, J=17.2 Hz, 2H), 8.23 (d, J=2.0 Hz, 1H), 8.15 (t, J=16.0 Hz, 1H), 7.96-7.99 (m, 2H), 7.70 (dd, J1=8.8 Hz, J2=2.4 Hz, 1H); MS (ESI): M$^+$+1=289.1.

EXAMPLE 25

Intermediate 25 (M25)

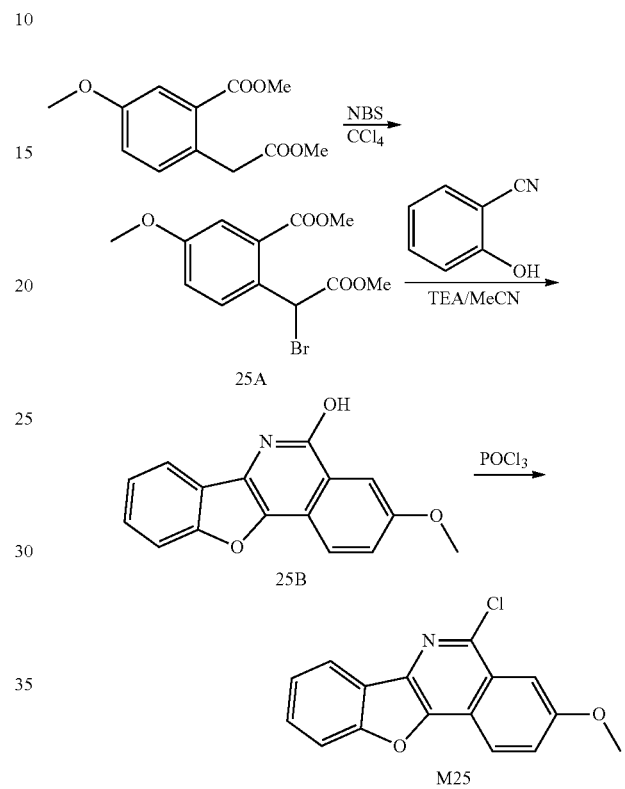

Step $S_{25A}$: Synthesis of 2-(4-methoxyl-2-methoxycarbonyl-phenyl)-2-bromo-acetic acid methyl ester (25A)

The procedure was similar to step $S_{19A}$, while the starting material was 5-methoxyl-2-methoxycarbonylmethyl-benzoic acid methyl ester (commercialized) in stead of 5-chloro-2-methoxycarbonyl methyl-benzoic acid methyl ester (18E). MS (ESI): M$^+$+1=318.1.

Step $S_{25B}$: Synthesis of 5-hydroxyl-3-methoxy-benzofuro[3,2-c]isoquinoline (25B)

The procedure was similar to step $S_{19B}$, while the starting material was 25A in stead of 19A. MS (ESI): M$^+$+1=266.3.

Step $S_{25C}$: Synthesis of 3-methoxy-5-chloro-benzofuro[3,2-c]isoquinoline (M25)

The procedure was similar to step $S_{19C}$, while the starting material was 25B in stead of 19B.

$^1$H-NMR (CDCl$_3$): δ (ppm): 8.336 (d, J=8.8 Hz, 1H), 8.242 (d, J=7.6 Hz, 1H), 7.746 (d, J=2.4 Hz, 1H), 7.711 (d, J=7.6 Hz, 1H), 7.53-7.58 (m, 2H), 7.48 (t, J=7.2 Hz, 1H), 4.06 (s, 3H); MS (ESI): M$^+$+1=284.7.

EXAMPLE 26

Intermediate 26 (M26)

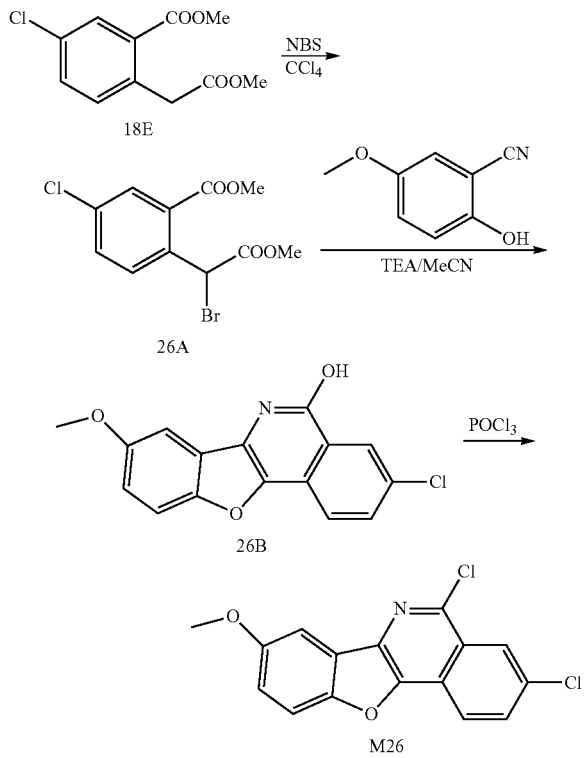

EXAMPLE 27

Intermediate 27 (M27)

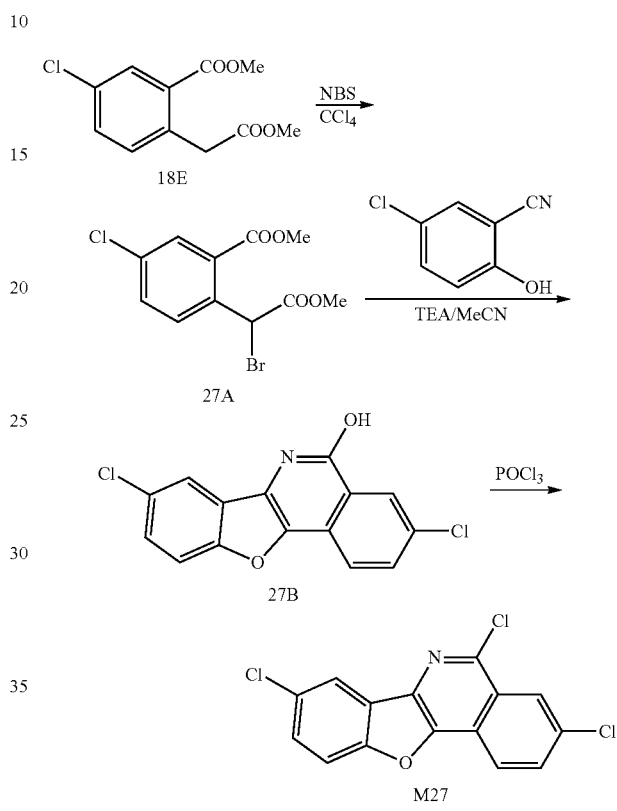

Step S$_{26A}$: Synthesis of 2-(4-chloro-2-methoxycarbonyl-phenyl)-2-bromo-acetic acid methyl ester (26A)

The procedure was similar to step 19A.

Step S$_{26B}$: Synthesis of 5-hydroxyl-3-chloro-8-methoxy-benzofuro[3,2-c]isoquinoline (26B)

The procedure was similar to step S$_{19B}$, while the starting material was 2-hydroxy-5-methoxy-benzonitrile in stead of 2-hydroxy-benzonitrile.

$^1$H-NMR (DMSO-d$_6$): δ (ppm): 12.49 (s,1H), 8.25 (d, J=2.0 Hz, 1H), 8.027 (d, J=8.8 Hz, 1H), 7.918 (dd, J1=8.8 Hz, J2=2 Hz, 1H), 7.669 (d, J=9.2 Hz, 1H), 7.587 (d, J=2.8 Hz, 1H), 7.097 (dd, J1=8.8 Hz, J2=2.8 Hz, 1H), 3.840 (s, 3H); MS (ESI): M$^+$+1=300.7.

Step S$_{26C}$: Synthesis of 3,5-dichloro-8-methoxy-benzofuro[3,2-c]isoquinoline (M26)

The procedure was similar to step S$_{19C}$, while the starting material was 26B in stead of 19B.

$^1$H-NMR (CDCl$_3$): δ (ppm): 8.502 (d, J=1.6 Hz, 1H), 8.360 (d, J=8.8 Hz, 1H), 8.871 (dd, J1=8.8 Hz, J2=1.6 Hz, 1H), 7.706 (s, J=2.4 Hz, 1H), 7.623 (d, J=9.2 Hz, 1H), 7.182 (dd, J1=9.2 Hz, J2=2.8 Hz, 1H), 3.964 (s, 3H); MS (ESI): M$^+$+1=319.2.

Step S$_{27A}$: Synthesis of 2-(4-chloro-2-methoxycarbonyl-phenyl)-2-bromo-acetic acid methyl ester (27A)

The procedure was similar to step 19A.

Step S$_{27B}$: Synthesis of 3,8-dichloro-5-hydroxyl-benzofuro[3,2-c]isoquinoline 1 (27B)

The procedure was similar to step S$_{19B}$, while the starting material was 5-chloro-2-hydroxy-benzonitrile in stead of 2-hydroxy-benzonitrile.

$^1$H-NMR (DMSO-d$_6$): δ (ppm): 12.539 (s, 1H), 8.246 (d, J=2.0 Hz, 1H), 8.039 (s, 1H), 8.028 (d, J=8.8 Hz, 1H), 7.926 (dd, J1=8.4 Hz, J2=2 Hz, 1H), 7.796 (d, J=8.8 Hz, 1H), 7.520 (dd, J1=8.8 Hz, J2=2.4 Hz, 1H); MS (ESI): M$^+$+1=305.1.

Step S$_{27C}$: Synthesis of 3,5,8-trichloro-benzofuro[3,2-c]isoquinoline (M27)

The procedure was similar to step S$_{19C}$, while the starting material was 27B in stead of 19B.

$^1$H-NMR (CDCl$_3$): δ (ppm): 8.510 (d, J=2.0 Hz, 1H), 8.356 (d, J=8.8 Hz, 1H), 8.220 (d, J=1.6 Hz, 1H), 7.890 (dd, J1=8.8

Hz, J2=1.6 Hz, 1H), 7.655 (d, J=8.8 Hz, 1H), 7.540 (dd, J1=8.4 Hz, J2=2 Hz, 1H); MS (ESI): M++1=323.6.

EXAMPLE 28

Intermediate 28 (M28)

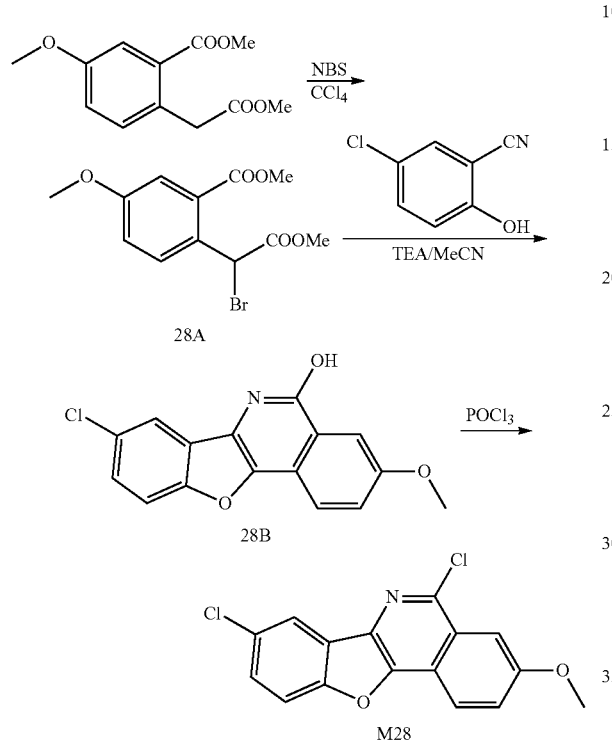

Step S28A: Synthesis of 2-(4-methoxyl-2-methoxy-carbonyl-phenyl)-2-bromo-acetic acid methyl ester (28A)

The procedure was similar to step S19A, while the starting material was 5-methoxy-2-methoxycarbonylmethyl-benzoic acid methyl ester (commercialized) in stead of 5-chloro-2-methoxycarbonyl methyl-benzoic acid methyl ester (18E).
MS (ESI): M++1=318.1.

Step S28B: Synthesis of 5-hydroxyl-3-methoxy-8-chloro-benzofuro[3,2-c]isoquinoline (28B)

The procedure was similar to step S19B, while the starting material was 28A in stead of 19A, and used 5-chloro-2-hydroxy-benzonitrile in stead of 2-hydroxy-benzonitrile.

Step S28C: Synthesis of 3-methoxy-5,8-dichloro-benzofuro[3,2-c]isoquinoline (M28)

The procedure was similar to step S19C, while the starting material was 28B in stead of 19B.
$^1$H-NMR (CDCl$_3$): δ (ppm): 8.325 (d, J=8.8 Hz, 1H), 8.204 (d, J=2.0 Hz, 1H), 7.761 (d, J=2.4 Hz, 1H), 7.634 (d, J=8.8

Hz, 1H), 7.591 (dd, J1=8.8 Hz, J2=2 Hz, 1H), 7.495 (dd, J1=8.8 Hz, J2=2.4 Hz, 1H), 4.070 (s, 3H); MS (ESI): M++1=319.1.

EXAMPLE 29

Intermediate 29 (M29)

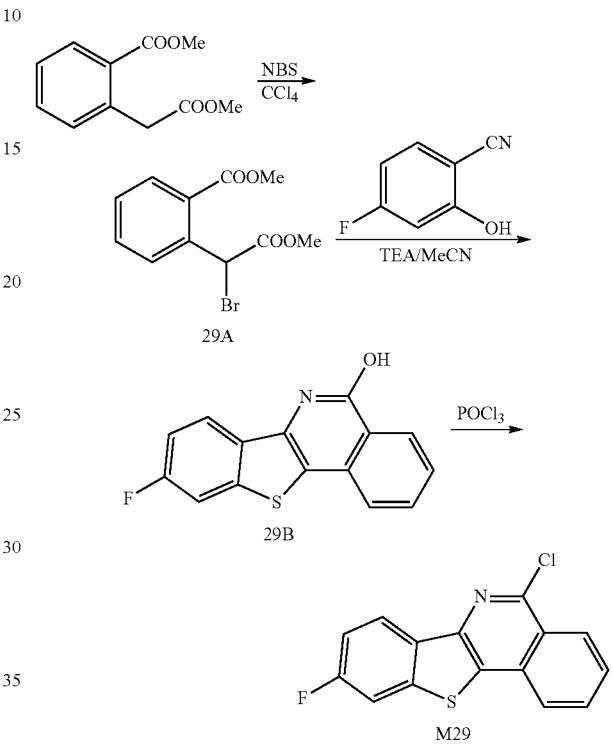

Step S29A: Synthesis of 2-(2-methoxycarbonyl-phenyl)-2-bromo-acetic acid methyl ester (29A)

The procedure was similar to step S19A, while the starting material was 2-methoxycarbonylmethyl-benzoic acid methyl ester in stead of 5-chloro-2-methoxycarbonyl methyl-benzoic acid methyl ester (18E).

Step S29B: Synthesis of 5-hydroxyl-9-fluoro-benzothieno[3,2-c]isoquinoline (29B)

The procedure was similar to step S19B, while the starting material was 29A in stead of 19A, and used 4-fluoro-2-mercapto-benzonitrile in stead of 2-hydroxy-benzonitrile.

Step S29C: Synthesis of 5-chloro-9-fluoro-benzothieno[3,2-c]isoquinoline (M29)

The procedure was similar to step S19C, while the starting material was 29B in stead of 19B.
$^1$H-NMR (CDCl$_3$): δ (ppm): 8.47 (d, J=8.4 Hz, 1H), 8.37 (m, 1H), 8.27 (d, J=8.0 Hz, 1H), 8.171 (d, J=8.4 Hz, 1H), 8.05 (dd, J1=8.0 Hz, J2=7.2 Hz, 1H), 7.49 (dd, J1=8.4 Hz, J2=8.0 Hz, 1H); MS(ESI): M++1=288.

EXAMPLE 30~70

Synthesis of Compound Ik (k=1, 2, 3 . . . 13, 15 . . . 41, 42)

Synthetic Method A

A mixture of intermediate Mi (I=1, 2, 3, . . . 11, 13, . . . 17, 19, . . . or 29) (0.1 mmol), starting material A-j (j=I, II, . . . or VI) (0.1 mmol) and t-BuOK (potassium tert-butoxide, 5 mmol) was cooled to 0° C. To the mixture was added DMSO (dimethyl sulfoxide, 5 mL), then warmed to room temperature within 20 min. TLC monitored the reaction. After the reaction completed, the reaction mixture was poured into ice-water, extracted with ethyl acetate (50 mL×3), dried over anhydrous $Na_2SO_4$, filtered, concentrated to dryness under reduced pressure and purified by preparative-TLC (silica gel, $CH_2Cl_2$: MeOH=100:5) to give desired product Ik.

Synthetic Method B

A mixture of starting material A-j (j=I, II, . . . or VI) (1 mmol) and t-BuOK (5 mmol) was dissolved in THF (tetrahydrofuran) and DMSO (2 ml+2 mL) and cooled to 0° C. To the solution was added a solution of intermediate Mi (I=1, 2, 3, . . . 11, 13, . . . 17, 19, . . . or 29) (1 mmol) in THF/DMSO (2 ml, 1/1) dropwise within 5 min at 0° C. The reaction mixture was stirred at room temperature overnight, then poured into water, extracted with ethyl acetate, dried over anhydrous $MgSO_4$ and purified by preparative-HPLC.

wherein, A-j (j=I, II, . . . or VI) (The references of preparation: 1) PCT Int. Appl., 2009140500, 19 Nov. 2009; 2) PCT Int. Appl., 2008008776, 17 Jan. 2008) was listed as follows:

A-I

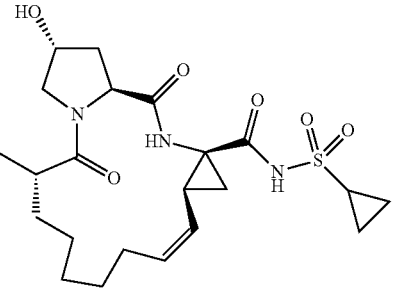

A-II

A-III

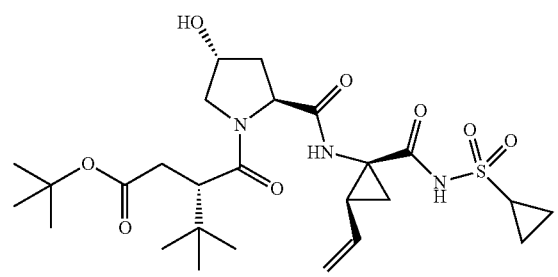

A-IV

A-V

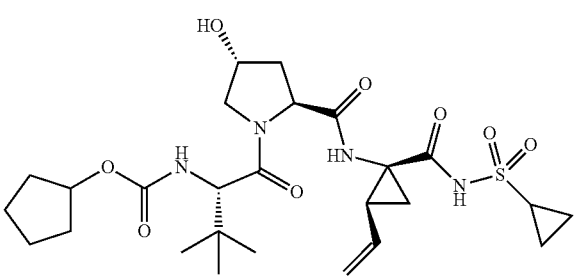

A-VI

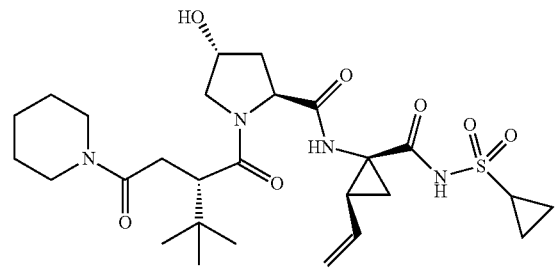

TABLE 1

| Example | Ik | A-j | Mi | Synthetic method | Compoud Structure | M⁺ + 1 |
|---|---|---|---|---|---|---|
| 30 | 1 | A-II | M2 | A | | 850.3 |
| 31 | 2 | A-I | M21 | A | | 816 |
| 32 | 3 | A-II | M4 | A | | 830 |

TABLE 1-continued
| Example | Ik | A-j | Mi | Synthetic method | Compoud Structure | M+ + 1 |
|---|---|---|---|---|---|---|
| 33 | 4 | A-II | M5 | A | 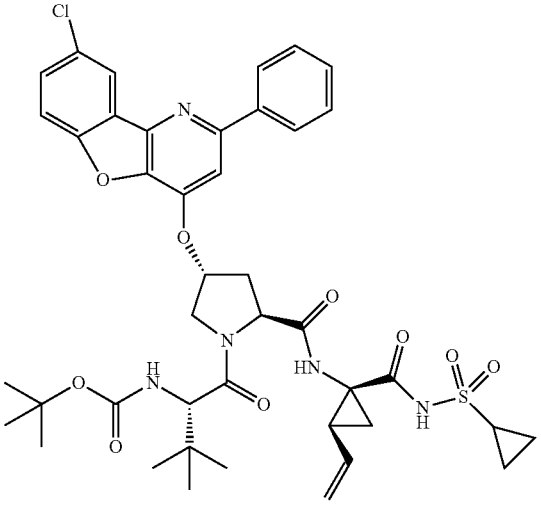 [SMILES: C=C[C@@H]1C[C@]1(NC(=O)[C@@H]1C[C@@H](Oc2cc(-c3ccccc3)nc3c2oc2ccc(Cl)cc23)CN1C(=O)[C@@H](NC(=O)OC(C)(C)C)C(C)(C)C)C(=O)NS(=O)(=O)C1CC1] | 834 |
| 34 | 5 | A-I | M24 | A | 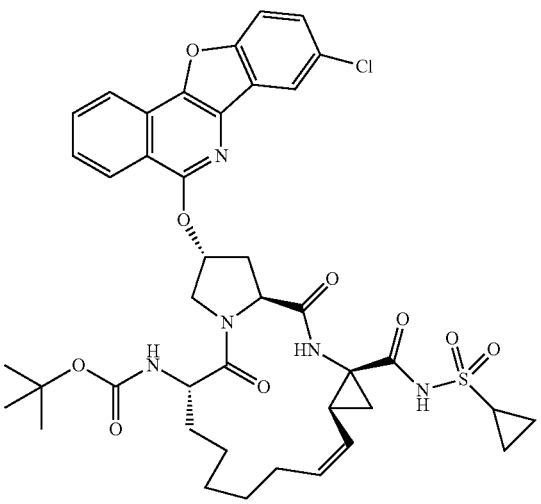 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](Oc3nc4c5cc(Cl)ccc5oc4c4ccccc34)CN2C1=O] | 820.2 |
| 35 | 6 | A-I | M22 | A | 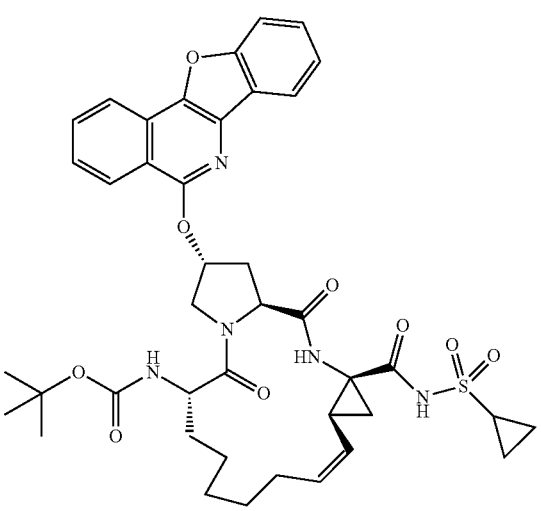 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](Oc3nc4c5ccccc5oc4c4ccccc34)CN2C1=O] | 786.3 |

TABLE 1-continued

| Example | Ik | A-j | Mi | Synthetic method | Compoud Structure | M⁺ + 1 |
|---|---|---|---|---|---|---|
| 36 | 7 | A-II | M17 | A | | 834.2 |
| 37 | 8 | A-II | M6 | A | | 878.2 |
| 38 | 9 | A-II | M3 | A | | 816.3 |

TABLE 1-continued

| Example | Ik | A-j | Mi | Synthetic method | Compoud Structure | M⁺ + 1 |
|---|---|---|---|---|---|---|
| 39 | 10 | A-I | M28 | A | | 820.2 |
| 40 | 11 | A-II | M24 | A | | 808.2 |
| 41 | 12 | A-II | M28 | A | | 808.2 |

TABLE 1-continued
| Example | Ik | A-j | Mi | Synthetic method | Compoud Structure | M+ + 1 |
|---------|----|----|----|-----------------|-------------------|--------|
| 42 | 13 | A-III | M24 | A | 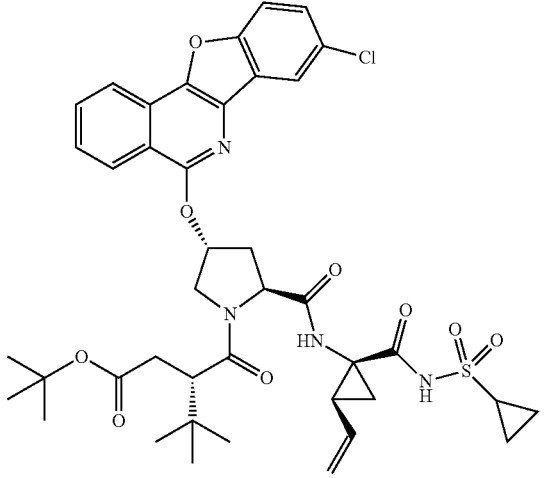 [SMILES: C=C[C@@H]1C[C@]1(NC(=O)[C@@H]1C[C@@H](Oc2nc3c4cc(Cl)ccc4oc3c3ccccc23)CN1C(=O)[C@@H](CC(=O)OC(C)(C)C)C(C)(C)C)C(=O)NS(=O)(=O)C1CC1] | 807.2 |
| 43 | 15 | A-II | M21 | A | 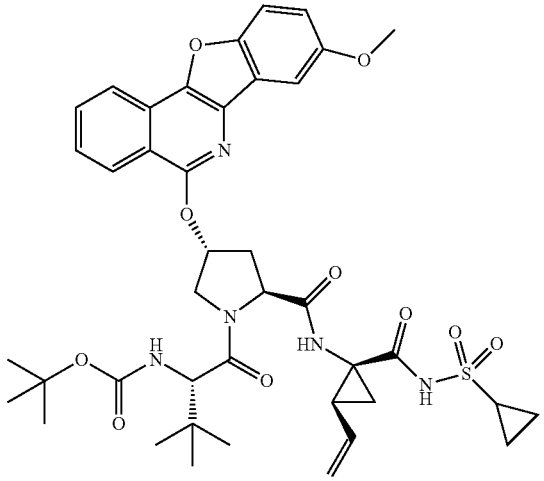 [SMILES: C=C[C@@H]1C[C@]1(NC(=O)[C@@H]1C[C@@H](Oc2nc3c4cc(OC)ccc4oc3c3ccccc23)CN1C(=O)[C@@H](NC(=O)OC(C)(C)C)C(C)(C)C)C(=O)NS(=O)(=O)C1CC1] | 804.3 |
| 44 | 16 | A-I | M20 | B | 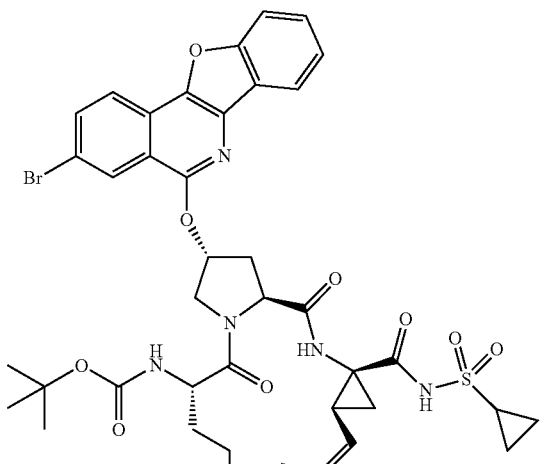 | 865.1 |

TABLE 1-continued

| Example | Ik | A-j | Mi | Synthetic method | Compoud Structure | M⁺ + 1 |
|---|---|---|---|---|---|---|
| 45 | 17 | A-I | M19 | B | | 820.3 |
| 46 | 18 | A-I | M25 | B | | 816.3 |
| 47 | 19 | A-I | M26 | B | | 850.2 |

TABLE 1-continued

| Example | Ik | A-j | Mi | Synthetic method | Compoud Structure | M⁺ + 1 |
|---------|----|----|-----|------------------|-------------------|--------|
| 48 | 20 | A-IV | M19 | B | | 820.2 |
| 49 | 21 | A-IV | M4 | A | | 842.3 |
| 50 | 22 | A-IV | M8 | A | | 876.3 |

TABLE 1-continued

| Example | Ik | A-j | Mi | Synthetic method | Compoud Structure | M⁺ + 1 |
|---|---|---|---|---|---|---|
| 51 | 23 | A-II | M8 | A | | 864.3 |
| 52 | 24 | A-II | M10 | B | | 913.3 |
| 53 | 25 | A-II | M10 | A | | 929.2 |

TABLE 1-continued
| Example | Ik | A-j | Mi | Synthetic method | Compound Structure | M⁺ + 1 |
|---------|----|----|----|------------------|--------------------|--------|
| 54 | 26 | A-II | M15 | A | 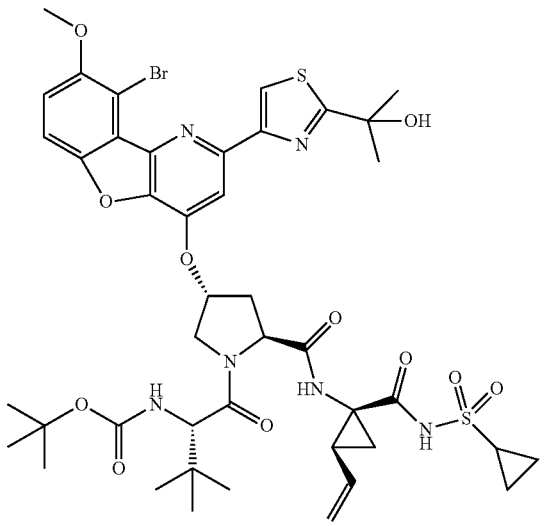 [SMILES: C=C[C@@H]1C[C@]1(NC(=O)[C@@H]1C[C@@H](Oc2cc(-c3csc(C(C)(C)O)n3)nc3c2oc2ccc(OC)c(Br)c23)CN1C(=O)[C@@H](NC(=O)OC(C)(C)C)C(C)(C)C)C(=O)NS(=O)(=O)C1CC1] | 973.2 |
| 55 | 27 | A-II | M13 | A | 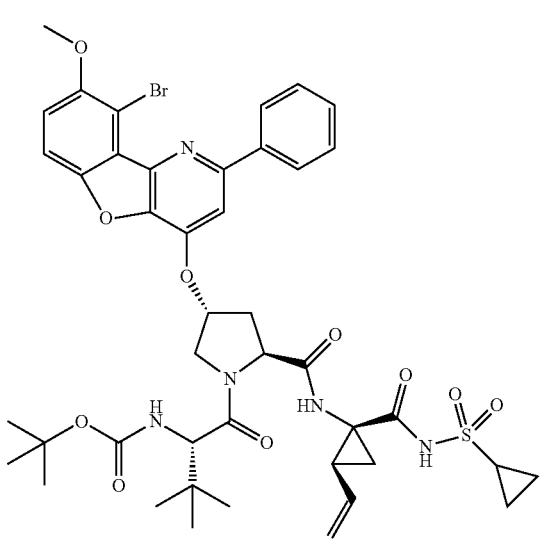 [SMILES: C=C[C@@H]1C[C@]1(NC(=O)[C@@H]1C[C@@H](Oc2cc(-c3ccccc3)nc3c2oc2ccc(OC)c(Br)c23)CN1C(=O)[C@@H](NC(=O)OC(C)(C)C)C(C)(C)C)C(=O)NS(=O)(=O)C1CC1] | 908.2 |
| 56 | 28 | A-IV | M13 | A | 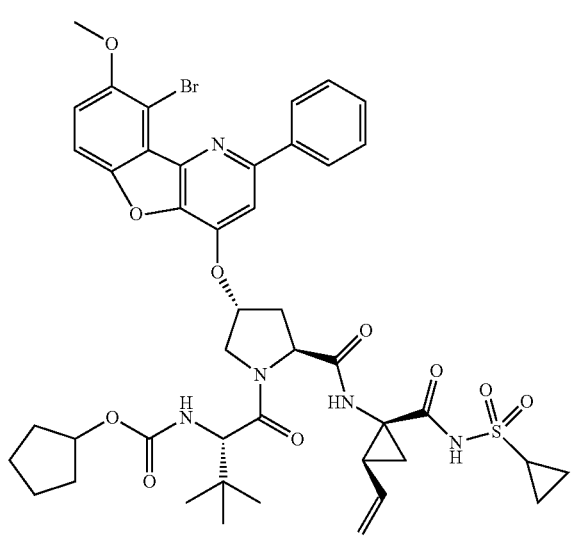 | 920.2 |

TABLE 1-continued

| Example | Ik | A-j | Mi | Synthetic method | Compoud Structure | M⁺ + 1 |
|---|---|---|---|---|---|---|
| 57 | 29 | A-II | M19 | B | | 808.2 |
| 58 | 30 | A-II | M20 | B | | 852.2 |
| 59 | 31 | A-II | M25 | B | | 804.3 |

TABLE 1-continued

| Example | Ik | A-j | Mi | Synthetic method | Compoud Structure | M⁺ + 1 |
|---------|----|----|----|------------------|-------------------|--------|
| 60 | 32 | A-II | M26 | B | | 838.2 |
| 61 | 33 | A-II | M27 | B | | 842.2 |
| 62 | 34 | A-II | M11 | A | | 956.3 |

TABLE 1-continued

| Example | Ik | A-j | Mi | Synthetic method | Compoud Structure | M⁺ + 1 |
|---|---|---|---|---|---|---|
| 63 | 35 | A-II | M16 | A | | 1000.2 |
| 64 | 36 | A-V | M1 | A | | 822.3 |
| 65 | 37 | A-VI | M1 | A | | 810.3 |

TABLE 1-continued

| Example | Ik | A-j | Mi | Synthetic method | Compound Structure | M⁺ + 1 |
|---|---|---|---|---|---|---|
| 66 | 38 | A-II | M1 | A | | 800.3 |
| 67 | 39 | A-II | M9 | A | | 929.2 |
| 68 | 40 | A-II | M14 | A | | 973.2 |

| Example | Ik | A-j | Mi | Synthetic method | Compound Structure | M⁺ + 1 |
|---------|----|----|----|------------------|--------------------|--------|
| 69 | 41 | A-II | M23 | A | 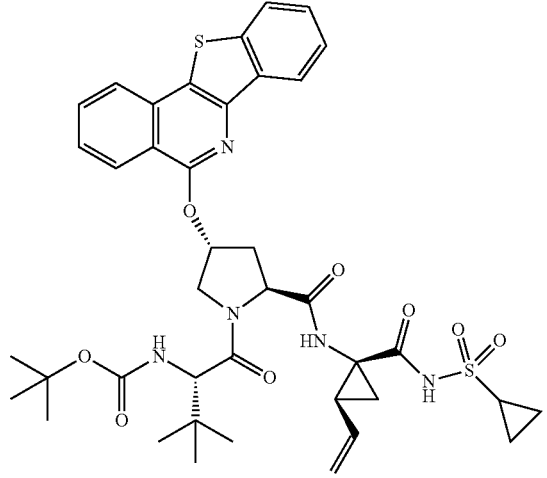 [SMILES: C=C[C@@H]1C[C@]1(NC(=O)[C@@H]1C[C@@H](Oc2nc3c4ccccc4sc3c3ccccc23)CN1C(=O)[C@@H](NC(=O)OC(C)(C)C)C(C)(C)C)C(=O)NS(=O)(=O)C1CC1] | 780.2 |
| 70 | 42 | A-II | M28 | B | 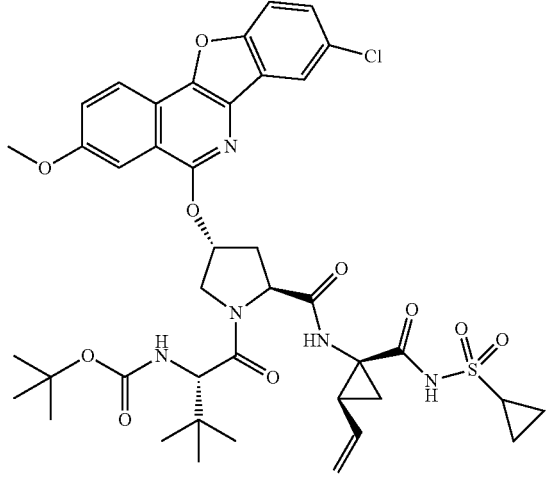 [SMILES: C=C[C@@H]1C[C@]1(NC(=O)[C@@H]1C[C@@H](Oc2nc3c4cc(Cl)ccc4oc3c3ccc(OC)cc23)CN1C(=O)[C@@H](NC(=O)OC(C)(C)C)C(C)(C)C)C(=O)NS(=O)(=O)C1CC1] | 838.2 |

Compound 2 tert-butyl(2R,6S,13aS,14aR,16aS,Z)-14a-(cyclopropylsulfonylcarbamoyl)-2-(8-methoxybenzofuro[3,2-c]isoquinolin-5-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl carbamate $^1$H-NMR (CDCl$_3$): δ (ppm): 10.29 (s, 1H), 8.33 (d, J=8.2 Hz, 1H), 8.22 (d, J=8.0 Hz, 1H), 7.78 (t, J=7.6 Hz, 1H), 7.49-7.55 (m, 3H), 7.08 (d, J=9.0 Hz, 1H), 6.96 (s, 1H), 6.11 (s, 1H), 5.70 (dd, J=8.8, 8.0 Hz, 1H), 5.20 (m, 1H), 4.98 (t, J=9.6 Hz, 1H), 4.67-4.72 (m, 2H), 4.33 (m, 1H), 4.12 (d, J=9.3 Hz, 1H), 3.99 (s, 3H), 2.80-2.92 (m, 2H), 2.73-2.78 (m, 1H), 2.49-2.59 (brs, 1H), 2.28 (q, J=8.8 Hz, 1H), 1.70-1.95 (m,3H), 1.55-1.65 (m, 1H), 1.40-1.52 (m, 7H), 1.28 (s, 10H), 1.08-1.15 (m, 2H), 0.91 (m, 1H); MS (ESI): M⁺+1=816.

Compound 3 tert-butyl(S)-1-((2S,4R)-2-((1R,2S)-1-(cyclopropylsulfonylcarbamoyl)-2-vinylcyclopropylcarbamoyl)-4-(8-methoxy-2-phenylbenzofuro [3,2-b]pyridin-4-yloxy)pyrrolidin-1-yl)-3,3-dimethyl-1-oxobutan-2-yl carbamate $^1$H-NMR (CDCl$_3$): δ (ppm): 9.27 (s, 1H), 8.02 (d, J=6.8 Hz, 2H), 7.82 (d, J=2.5 Hz, 1H), 7.69 (s, 1H), 7.61-7.65 (m, 4H), 7.33 (d, J=9.2 Hz, 1H), 5.84 (brs, 1H), 5.71 (dd, J=18.3, 9.6 Hz, 1H), 5.30 (d, J=18.3 Hz, 1H), 5.13 (d, J=9.6 Hz, 1H), 4.56-4.62 (m, 2H), 3.95-4.18 (m, 2H), 3.94 (s, 3H), 2.91-2.97 (m, 1H), 2.71 (dd, J=6.7, 14.1 Hz, 1H), 2.57 (ddd, J=14.1, 10.8, 4.1 Hz, 1H), 2.23 (dd, J=8.1, 17.5 Hz, 1H), 1.89 (dd, J=5.5, 17.8 Hz, 1H), 1.45 (dd, J=5.3, 9.2 Hz, 1H), 1.21-1.27 (m, 2H), 1.10 (s, 11H), 1.02 (s, 9H); MS (ESI): M⁺+1=830.

Compound 4 tert-butyl(S)-1-((2S,4R)-4-(8-chloro-2-phenylbenzofuro[3,2-b]pyridin-4-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-yl carbamate $^1$H-NMR (CDCl$_3$): δ (ppm): 9.27 (s, 1H), 8.30 (s, 1H), 8.04 (d, J=8.4 Hz, 2H), 7.61-7.70 (m, 3H), 7.51-7.58 (m, 3H), 5.71-5.80 (m, 2H), 5.30 (d, J=16.7 Hz, 1H), 5.13 (d, J=10.4 Hz, 1H), 4.52-4.62 (m, 2H), 3.20 (s, 1H), 4.13 (d, J=10.0 Hz, 1H), 2.91-2.97 (m, 1H), 2.67 (dd, J=6.8, 13.9 Hz, 1H), 2.57 (ddd, J=14.1, 10.8, 4.1, 1H), 2.23 (dd, J=8.1, 17.5 Hz, 1H), 1.88 (dd, J=5.5, 17.8 Hz, 1H), 1.45 (dd, J=5.3, 9.2 Hz, 1H), 1.21-1.27 (m, 2H), 1.12 (s, 11H), 1.02 (s, 9H); MS (ESI): M$^+$+1=834.

EXAMPLE 71

Compound 14

Synthesis of (2S,4R)-1-((S)-2-tert-butyl-4-oxo-4-(piperidin-1-yl)butanoyl)-4-(8-chlorobenzofuro[3,2-c]isoquinolin-5-yloxy)-N-((1R,2S)-1-(cyclopropylsulfonylcarbamoyl)-2-vinylcyclopropyl)pyrrolidine-2-carboxamide

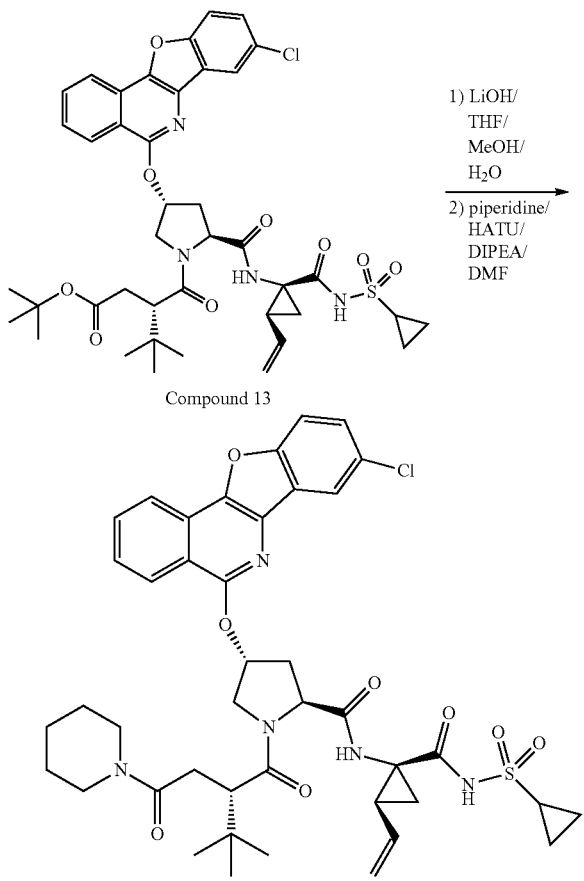

A mixture of compound 13 (40.4 mg, 0.05 mmol) and LiOH (5 eq) was dissolved in THF/MeOH/H$_2$O (3 mL/3 mL/3 mL) and stirred at room temperature for 3 hours. TLC monitored the reaction. After the reaction completed, the reaction mixture was acidified with 1N hydrochloric acid to pH~7, then extracted with ethyl acetate, dried over MgSO$_4$, filtered and concentrated to dryness under reduced pressure. The residue was dissolved in dimethylfomamide, then piperidine (0.1 mmol), o-(7-azabenzotriazol-1-yl)-N,N,N',N'-tetramethyluronium hexafluorophosphate (HATU) (0.065 mmol) and N,N-diisopropyl ethylamine (0.2 mmol) were added. The reaction mixture was stirred at room temperature overnight, then poured into water, extracted with ethyl acetate (50 mL×3), dried over MgSO$_4$ and purified by flash chromatography to give desired product 14.

$^1$H-NMR (CDCl$_3$): δ (ppm): 10.21 (s, 1H), 8.50 (d, J=8.4 Hz, 1H), 8.24 (d, J=8.0 Hz, 1H), 8.01 (brs, 1H), 7.82 (t, J=8.0 Hz, 1H), 7.54-7.60 (m, 2H), 7.43 (dt, J=8.8, 1.2 Hz, 1H), 7.14 (brs, 1H), 6.06 (brs, 1H), 5.75-5.83 (m, 1H), 5.25 (m, d, J=17.2 Hz, 1H), 5.13 (d, J=10.0 Hz, 1H), 4.63 (d, J=11.6 Hz, 1H), 4.51 (t, J=8.0 Hz, 1H), 4.14 (dd, J=8.8, 2.0 Hz, 1H), 3.63 (s, 2H), 3.05-3.20 (m, 2H), 2.86-3.00 (m, 2H), 2.68-2.73 (m, 1H), 2.57-2.63 (m, 1H), 2.35 (d, J=14.4 Hz, 1H), 2.06-2.13 (m, 1H), 1.99 (t, J=8.0 Hz, 1H), 1.43-1.60 (m, 5H), 1.28-1.42 (m, 4H), 0.9-1.10 (m, 11H); MS (ESI): M$^+$+1=818.3.

EFFECT EXAMPLE 1

In Vitro Inhibitory Activity of Compounds in HCV Replication in HCV Infected Human Hepatocellular Carcinoma Cells (Huh7.5.1)

The preparation of Huh7.5.1cells: Huh 7.5.1 cells were seeded at a 96-well plate with 37 and 5% CO$_2$ for 24 hours incubation.

Virus infection: Using the J399EM virus supernatants (moi≈0.1) to infect Huh7.5.1cells. At the same time, the no virus infected cell will be set up as the control. After 8 hours virus infection, the virus will be washed out with PBS.

Drug treatment: The different doses of samples (i.e. the compound Ik, wherein k=1, 2, 3, . . . 42) were added in J399EM infected Huh7.5.1 cells, the each dose for duplicate. At the same time the no sample added in wells will be set up as the control. The test dose of sample is starting from 25 nM or 400 nM, with quarter dilution, 5 doses of sample will be added in the test wells, respectively, then continued for 72 hours incubation.

HCV-EGFP fluorescence detection: After samples treatment for 72 hours, the autofluorescence of HCV-EGFP were measured by the luminometer with excitation of 488 nm, and emission of 516 nm. The related fluorescence unit (RFU) of samples will be read out and used for calculating the inhibitory rates of compounds in HCV replication.

EFFECT EXAMPLE 2

The Inhibitory Activity of Compounds in the HCV Replicon System

HCV replicon cell-line: The Huh7 cells were transfected with pSGR-399LM replicon DNA and cultured in the DMEM containing 10% FBS and 0.5 mg/mL G418. The cells were split at 1:3 to 1:5 every 3-4 days. The transfected cells were seeded in 96-well plates and cultured at 37° C., 5% $CO_2$ for 24 hr.

Treatment with samples: To the HCV replicon Huh7 cells-line were added different concentration of the samples (i.e. compound Ik, wherein k=1, 2, 3 . . . 42), the each concentration for duplicate, and set no sample control wells. The concentration started at 400 nM, with quarter dilution to form five different concentrations of samples, that is 400 nM, 100 nM, 25 nM, 6.25 nM and 1.56 nM. The samples were added separately, and continued to incubated for 72 hr.

Fluorescence detection: After 72 hr treatment with sample, the cells were lysed and added with Renilla luciferase substrate to detect luminescent signal. The relative luminescent unit (RLU) in the luminometer was read out and used to calculate the inhibition rate of HCV.

TABLE 2

| compound | MS(ESI): $M^+ + 1$ | HCV replicon system $EC_{50}$(nM) | HCV infected human hepatocellular carcinoma cells in vitro $EC_{50}$(nM) |
|---|---|---|---|
| 1 | 850 | B | B |
| 2 | 816 | A | A |
| 3 | 830 | A | B |
| 4 | 834 | A | B |
| 5 | 820 | A | A |
| 6 | 786 | A | A |
| 7 | 834 | A | A |
| 8 | 878 | A | B |
| 9 | 816 | A | B |
| 10 | 820 | A | A |
| 11 | 808 | A | B |
| 12 | 808 | A | B |
| 13 | 807 | B | B |
| 14 | 818 | A | B |
| 15 | 804 | B | B |
| 16 | 865 | A | A |
| 17 | 820 | A | A |
| 18 | 816 | A | A |
| 19 | 850 | A | A |
| 20 | 820 | A | A |
| 21 | 842 | A | B |
| 22 | 876 | A | A |
| 23 | 864 | A | A |
| 24 | 913 | A | A |
| 25 | 929 | A | A |
| 26 | 973 | A | A |
| 27 | 908 | A | A |
| 28 | 920 | A | A |
| 29 | 808 | A | A |
| 30 | 852 | B | B |
| 31 | 804 | B | B |
| 32 | 838 | A | B |
| 33 | 842 | B | B |
| 34 | 956 | A | A |
| 35 | 1000 | A | A |
| 36 | 822 | A | B |
| 37 | 810 | B | B |
| 38 | 800 | A | A |
| 39 | 929 | A | A |
| 40 | 973 | A | A |
| 41 | 780 | — | — |
| 42 | 838 | — | — |

A: $EC_{50} \leq 100$ nM,
B: 100 nM < $EC_{50}$ < 1000 nM

EFFECT EXAMPLE 3

Pharmacokinetic Evaluation of the Compounds of this Invention

Experimental

Twenty healthy male Sprague-Dawley (SD) rats with body weight of 200-220 g were divided into 5 groups randomly and each group contains 4 rats. Before the experiment, rats were fasted for 12 h with free access to water. The compound Ik (wherein k=2, 5, 18, 34 or 38) of this invention was administered by oral gavage at a dose level of 10 mg/kg. The compounds were prepared with 0.5% CMC-Na containing 1% Tween 80. The dose volume was 10 mL/kg. The rats were afforded unlimited access to food after 2 h of dosing 0.3 mL of blood samples were collected at 0.25 h, 0.5 h, 1.0 h, 2.0 h, 3.0 h, 5.0 h, 7.0 h, 9.0 h, and 24.0 h, respectively, from postocular venous plexes of the rat. The blood samples were placed in heparin-containing tubes and immediately centrifuged at 11000 rpm for 5 min. Plasma was separated and refrigerated at −20° C. until analysis. LC-MS/MS methods were used to quantify plasma concentrations of the compound Ik. The pharmacokinetic parameters obtained are shown in Table 3.

TABLE 3

Pharmacokinetic parameters of SD rats after oral administration

| Compound | $T_{max}$ (h) | $C_{max}$ (ng/mL) | $AUC_{0-t}$ (ng · h/mL) | $AUC_{0-\infty}$ (ng · h/mL) | $t_{1/2}$ (h) | F (%) |
|---|---|---|---|---|---|---|
| I38 | 0.63 ± 0.25 | 150 ± 42 | 239 ± 81 | 243 ± 81 | 0.72 ± 0.30 | 8.7 |
| I5 | 1.25 ± 0.50 | 560 ± 139 | 2882 ± 1720 | 3028 ± 1705 | 3.48 ± 1.09 | 17.1 |
| I18 | 1.7 ± 0.6 | 623.3 ± 60.7 | 3218.5 ± 336.4 | 3266.8 ± 303.2 | 3.8 ± 1.0 | 36.1 |
| I34 | 0.4 ± 0.2 | 11.4 ± 4.3 | 9.6 ± 0.9 | 11.0 ± 1.1 | 0.5 ± 0.3 | 1.6 |
| I2 | 0.4 ± 0.1 | 49.7 ± 11.0 | 157.9 ± 49.8 | 1777.6 ± 53.7 | 3.1 ± 1.3 | 1.8 |

Experimental Conclusions

The compounds of this invention showed satisfied pharmacokinetic behaviour. For instance, Compound I18 was orally administered to SD rats at 10 mg/kg. The peak plasma concentration was at 1.7±0.6 h, with $C_{max}$ of 623±60.7 ng/mL, and the area under plasma concentration-time curves $AUC_{0-t}$ was 3218.5±336.4 ng·h/mL, $AUC_{0-\infty}$ was 3266.8±303.2 ng·h/mL. The elimination half-life $t_{1/2}$ was 3.8±1.0 h. The absolute bioavailability F approached to 36.1%.

INDUSTRIAL APPLICABILITY OF THE INVENTION

The compounds of the present invention have the excellent activity of anti-hepatitis C virus. The value $EC_{50}$ of the desired compounds for HCV replicon system (pSGR-399LM+Huh7.5) all are lesser than 1000 nM. A majority of compounds are lesser than 100 nM. The value $EC_{50}$ of the compounds for HCV infected human hepatocellular carcinoma cells (Huh7.5.1) in vitro all are lesser than 1000 nM also. And the compounds of this invention showed satisfied pharmacokinetic behaviour also.

What is claimed is:

1. A compound having the formula (I):

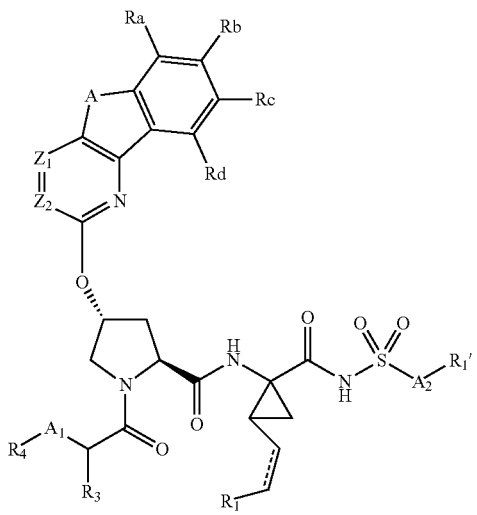

(I)

or a pharmaceutically acceptable salt thereof, wherein,

A is O, S, CH, NH or NR', wherein, R' is $C_1$-$C_6$ alkyl which can be substituted by halogen;

$Z_1$ is N or $CR_{Z1}$, $Z_2$ is $CR_{Z2}$, wherein, $R_{Z1}$ is hydrogen, halogen, $C_1$-$C_6$ alkyl, $C_1$-$C_6$ alkoxy, $NH_2$, ($C_1$-$C_6$ alkyl)NH or ($C_1$-$C_6$ alkyl)$_2$N, $R_{Z2}$ is hydrogen, $C_1$-$C_6$ alkyl, $C_1$-$C_6$ alkoxy, 6-10 membered aryl or 5-10 membered heteroaryl having 1-4 heteroatoms selected from O, N and S; or $R_{Z1}$, $R_{Z2}$ with carbon atoms linking with them together form a 5-8 membered simple carbon ring or double carbon ring which can be inserted by 1-3 heteroatoms selected from N, O and S, and which can be substituted by Re, Rf, Rg, or Rh, wherein the definition of Re, Rf, Rg, and Rh is the same as that of Ra, Rb, Rc and Rd;

Ra, Rb, Rc and Rd independently is H, OH, halogen or —$Y^1$—$R^m$, $Y^1$ is linking bond, O, S, SO, $SO_2$ or $NR''$; $R^m$ is hydrogen, or a substituent which can be substituted by 1-5 $R'''$ selected from the following group: ($C_1$-$C_8$) alkyl, N≡C—($C_1$-$C_6$) alkyl, ($C_2$-$C_8$) alkenyl, ($C_2$-$C_8$) alkynyl, ($C_3$-$C_7$) cycloalkyl, ($C_3$-$C_7$ cycloalkyl) ($C_1$-$C_6$) alkyl, and 5~6 membered aryl or heteroaryl having 1-2 heteroatom(s) independently selected from N, O, S; $R''$ is H, ($C_1$-$C_6$) alkyl or ($C_3$-$C_6$) cycloalkyl; $R'''$ is a substituent selected from the following group: halogen, ($C_1$-$C_6$) alkyl substituted optionally by ($C_1$-$C_6$)alkyl-O— or ($C_3$-$C_6$) cycloalkyl-O—, ($C_1$-$C_6$) haloalkyl, ($C_3$-$C_7$) cycloalkyl, ($C_1$-$C_6$) alkyl-O—, —$NH_2$, ($C_1$-$C_4$ alkyl) NH_ and ($C_1$-$C_4$ alkyl)$_2$N—;

$A_1$ is NH or $CH_2$;

$A_2$ is N, O or linking bond;

$R_1'$ is a substituent which can be substituted by 1 or more $R_1''$ selected from the following group: $C_1$-$C_6$ alkyl, $C_2$-$C_6$ alkenyl, $C_2$-$C_6$ alkynyl, 6-10 membered aryl, (6-10 membered aryl) $C_1$-$C_2$ alkyl, $C_3$-$C_7$ cycloalkyl, ($C_3$-$C_7$ cycloalkyl) $C_1$-$C_2$ alkyl, $C_3$-$C_7$ cycloalkenyl, ($C_3$-$C_7$ cycloalkenyl) $C_1$-$C_2$ alkyl, 4-7 membered heterocycl having 1-4 heteroatoms selected from O, S and N, (4-7 membered heterocycl having 1-4 heteroatoms selected from O, S, and N) $C_1$-$C_2$ alkyl, $C_5$-$C_{10}$ heteroaryl and ($C_5$-$C_{10}$ heteroaryl) $C_1$-$C_2$ alkyl; $R_1''$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)—NH—and —N($C_1$-$C_6$ alkyl)$_2$;

$R_1$ is hydrogen; or; $R_1$ linking covalently with $R_3$ together forms a $C_5$-$C_9$ saturated or unsaturated hydrocarbon chain which can be inserted by 0~2 heteroatom(s) independently selected from N, S and O, or which can be substituted by none or more halogen, O, S or —$NR_pR_q$, wherein, $R_p$ and $R_q$ independently is hydrogen or $C_1$-$C_6$ alkyl;

$R_3$ is $C_1$-$C_6$ alkyl, $C_2$-$C_6$ alkenyl, $C_3$-$C_7$ cycloalkyl, $C_3$-$C_7$ cycloalkenyl, 4-7 membered heterocycl having 1-4 heteroatoms selected from O, S, and N, ($C_3$-$C_7$ cycloalkyl) $C_1$-$C_4$ alkyl, ($C_3$-$C_7$ cycloalkenyl) $C_1$-$C_4$ alkyl, (4-7 membered heterocycl having 1-4 heteroatoms selected from O, S and N) $C_1$-$C_4$ alkyl, $C_2$-$C_6$ alkylacyl, ($C_1$-$C_4$ alkyl)$_{1-2}$ ($C_3$-$C_7$) cycloalkyl or ($C_1$-$C_6$ alkyl)$_{1-2}$ amino; and $R_4$ is $C_1$-$C_{10}$ alkoxycarbonyl, ($C_1$-$C_{10}$ alkyl)NHCO, ($C_1$-$C_{10}$ alkyl)$_2$NCO, 6-10 membered aryl, 5-10 membered heteroaryl having 1-4 heteroatoms selected from O, N and S or formyl substituted by 3~7 membered cycloalkyl, 4-7 membered heterocycl having 1-4 heteroatoms selected from O, S, and N or cycloalkoxy, which can be substituted by 1 or more $R_4'$; $R_4'$ is a substituent selected from the following group: halogen, OH, ON CN, $C_1$-$C_6$ alkyl, $C_2$-$C_6$ alkynyl, $C_1$-$C_6$ alkoxyl, —$NH_2$, ($C_1$-$C_6$ alkyl)—NH— and —N($C_1$-$C_6$ alkyl)$_2$, ($C_1$-$C_6$ alkyl)—$SO_2$—.

2. The compound as claimed in claim 1, characterized in that when $Z_3$ links with O, $R_{Z1}$, $R_{Z2}$ with carbon atoms linking with them together form a 6 membered aromatic ring substituted by Re, Rf, Rg and Rh, therefore, the structure of the compound having the general formula (I) is shown in formula (Ia), (Ia)

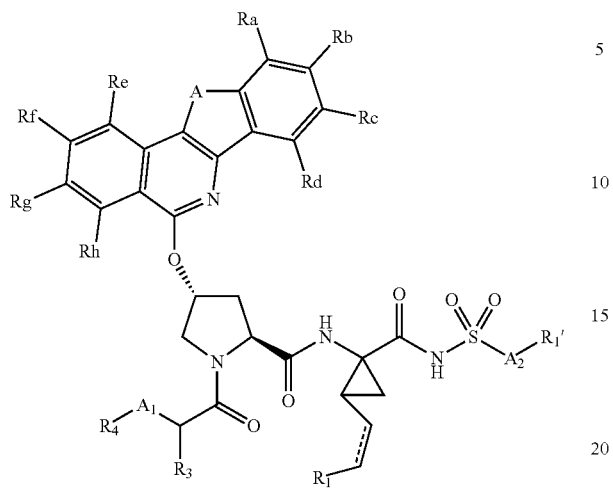

(Ib2)

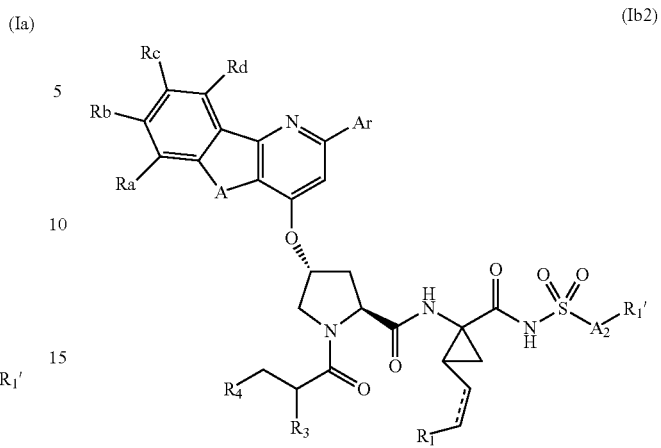

wherein, the definition of Re, Rf, Rg and Rh is the same as that of Ra, Rb, Rc and Rd.

3. The compound as claimed in claim 1, characterized in that when $Z_1$ links with O, the structure of the compound having the general formula (I) is shown in formula (Ib1), (Ib1)

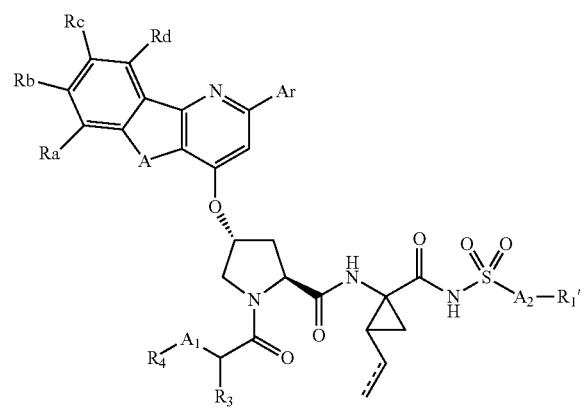

wherein, $R_3$ is $C_1$-$C_6$ alkyl, $C_2$-$C_6$ alkenyl, $C_3$-$C_7$ cycloalkyl, $C_3$-$C_7$ cycloalkenyl, heterocycloalkyl, ($C_3$-$C_7$ cycloalkyl) $C_1$-$C_4$ alkyl, ($C_3$-$C_7$ cycloalkenyl) $C_1$-$C_4$ alkyl, (heterocycloalkyl) $C_1$-$C_4$ alkyl, $C_2$-$C_6$ alkylacyl, ($C_1$-$C_4$ alkyl)$_{1-2}$($C_3$-$C_7$) cycloalkyl or ($C_1$-$C_6$ alkyl)$_{1-2}$ amino.

4. The compound as claimed in claim 1, characterized in that when $Z_1$ links with O, the structure of the compound having the general formula (I) is shown in formula (Ib2), wherein, $R_1$ linking covalently with $R_3$ together forms a $C_5$-$C_9$ saturated or unsaturated hydrocarbon chain which can be inserted by 0~2 heteroatom(s) independently selected from N, S and O, or which can be substituted by none or more halogen, O, S or —$NR_pR_q$, wherein, $R_p$ and $R_q$ independently is hydrogen or $C_1$-$C_6$ alkyl.

5. The compound as claimed in claim 3, characterized in that Ar is a 6 membered aryl or a 5~6 membered heteroaryl which is substituted optionally by 1 or more $R_{Ar}$; wherein, $R_{Ar}$ is selected from the following substituent group: halogen, amino, $C_1$-$C_6$ alkyl, $C_1$-$C_6$ alkoxyl, $C_1$-$C_6$ hydroxyalkyl and ($C_1$-$C_6$) alkylamido.

6. The compound as claimed in claim 2, characterized in that $R'''$ is a substituent which can be substituted by 1~3 $R''''$ selected from the following group: $C_1$-$C_8$ alkyl, N≡C—($C_1$-$C_6$) alkyl, ($C_2$-$C_8$) alkenyl, ($C_2$-$C_8$) alkynyl, ($C_3$-$C_7$) cycloalkyl, ($C_3$-$C_7$ cycloalkyl) ($C_1$-$C_6$) alkyl, and 5~6 membered aryl or heteroaryl having 1-2 heteroatom(s) independently selected from N, O, S; $R''''$ is a substituent selected from the following group: halogen, ($C_1$-$C_6$) alkyl substituted optionally by ($C_1$-$C_6$)alkyl—O— or ($C_3$-$C_6$)cycloalkyl—O—, ($C_1$-$C_6$) haloalkyl, ($C_3$-$C_7$)cycloalkyl, ($C_1$-$C_6$)alkyl—O—, —$NH_2$, ($C_1$-$C_4$ alkyl)NH— and ($C_1$-$C_4$ alkyl)$_2$N—.

7. The compound as claimed in claim 2, characterized in that $R_1'$ is a substituent which can be substituted by 1 or more $R_1''$ selected from the following group: $C_1$-$C_6$ alkyl, $C_2$-$C_6$ alkenyl, $C_2$-$C_6$ alkynyl, 6-8 membered aryl, (6-8 membered aryl) $C_1$-$C_2$ alkyl, $C_3$-$C_7$ cycloalkyl, ($C_3$-$C_7$ cycloalkyl) $C_1$-$C_2$ alkyl, $C_3$-$C_7$ cycloalkenyl, ($C_3$-$C_7$ cycloalkenyl) $C_1$-$C_2$ alkyl, 4-6 membered heterocycl having 1-3 heteroatoms selected from O,S, and N, (4-6 membered heterocycle having 1-3 heteroatoms selected from O, S and N) $C_1$-$C_2$ alkyl, $C_5$-$C_{10}$ heteroaryl and ($C_5$-$C_{10}$ heteroaryl) $C_1$-$C_2$ alkyl;

$R_1''$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —$NH_2$, ($C_1$-$C_6$ alkyl)—NH— and —N($C_1$-$C_6$ alkyl)$_2$.

8. The compound as claimed in claim 2, characterized in that R₁' is

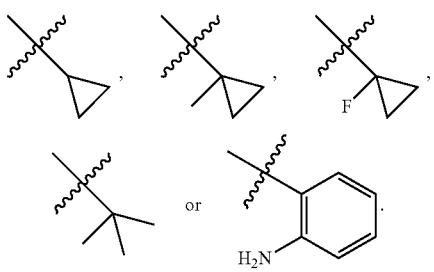

or

9. The compound as claimed in claim 2, characterized in that R₁ linking covalently with R₃ together forms a C₅ alkane chain.

10. The compound as claimed in claim 2, characterized in that R₄ is C₁-C₁₀ alkoxycarbonyl, (C₁-C₁₀ alkyl)—NHCO, (C₁-C₁₀ alkyl)₂NCO, 6-8 membered aryl, 5-8 membered heteroaryl having 1-3 heteroatoms selected from O, N and S or formyl substituted by 3~7 membered cycloalkyl, 4-6 membered heterocycl having 1-3 heteroatoms selected from O,S and N or cycloalkoxy, which can be substituted by 1 or more R₄';

R₄' is a substituent selected from the following group: halogen, OH, CN, C₁-C₆ alkyl, C₂-C₆ alkenyl, C₂-C₆ alkynyl, C₁-C₆ alkoxyl, —NH₂, (C₁-C₆alkyl)—NH— and —N(C₁-C₆ alkyl)₂, (C₁-C₆ alkyl)—SO₂—.

11. The compound as claimed in claim 2, characterized in that R₄ is

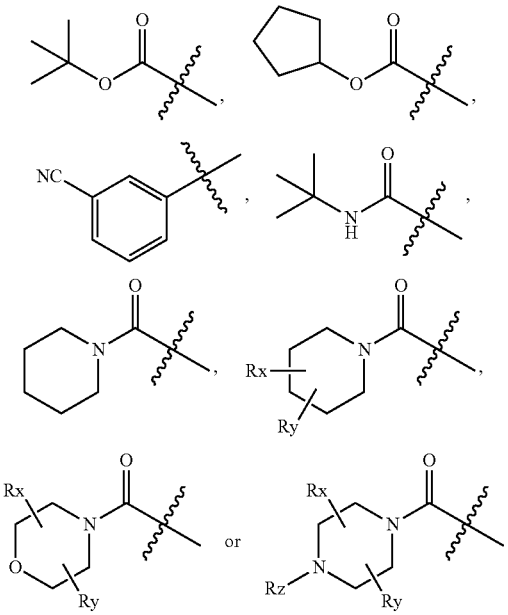

wherein, Rx and Ry independently is F, Cl, C₁-C₆ alkyl or C₁-C₆ alkoxyl, Rz is C₁-C₆ alkyl, C₁-C₆ alkoxyl, C₁-C₆ alkylformyl or (C₁-C₆alkyl)—SO₂—.

12. The compound as claimed in claim 1, characterized in that the compound is

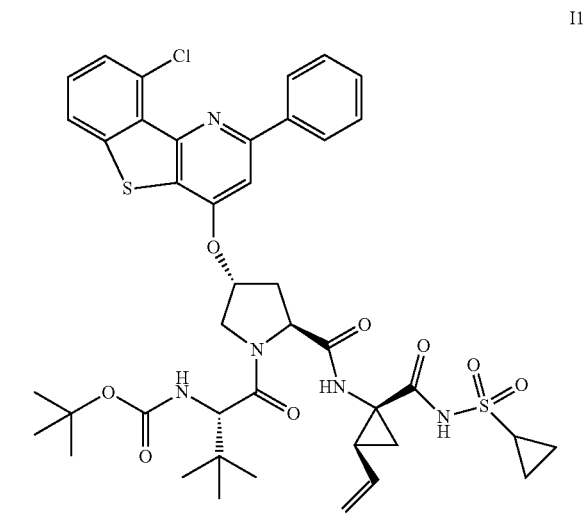

I1

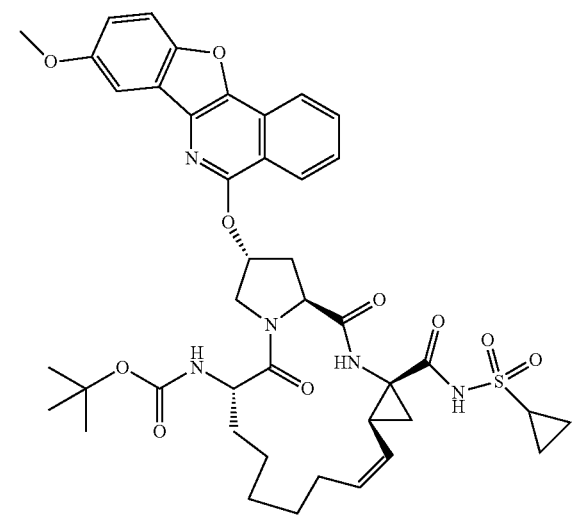

I2

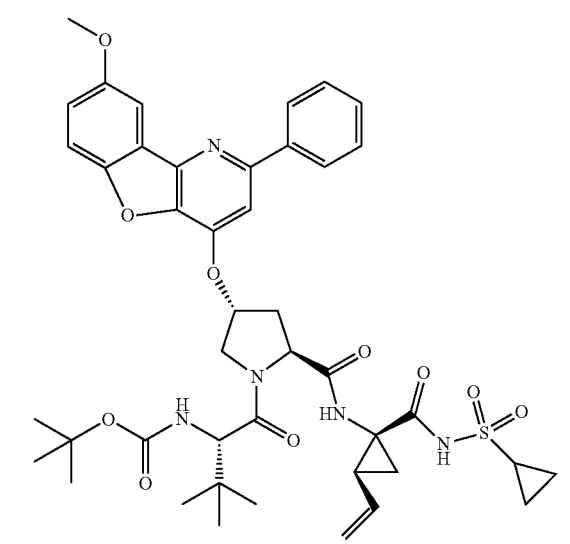

I3

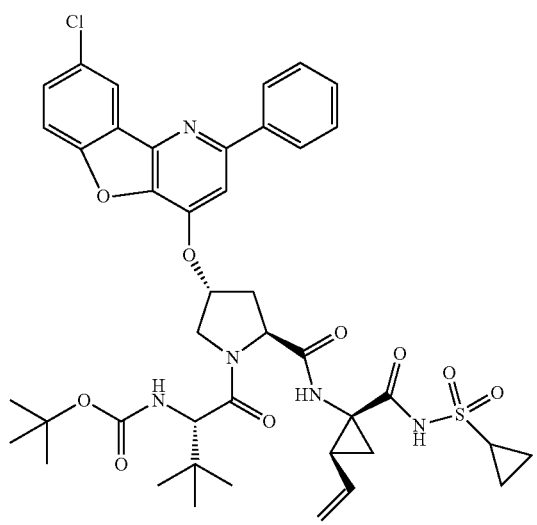
I4
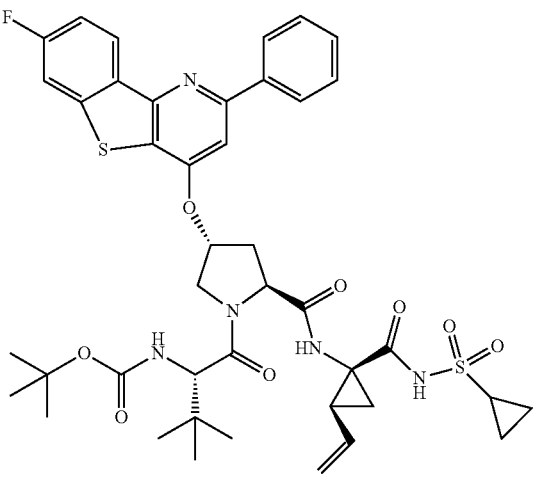
I7
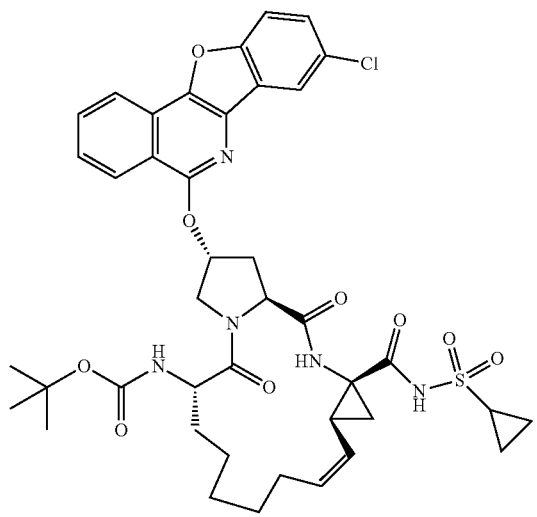
I5
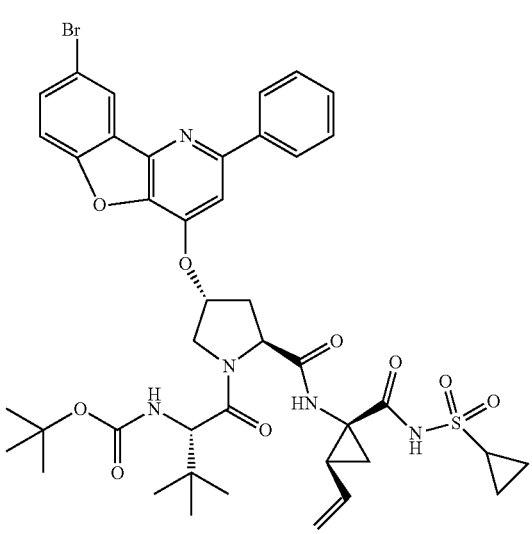
I8
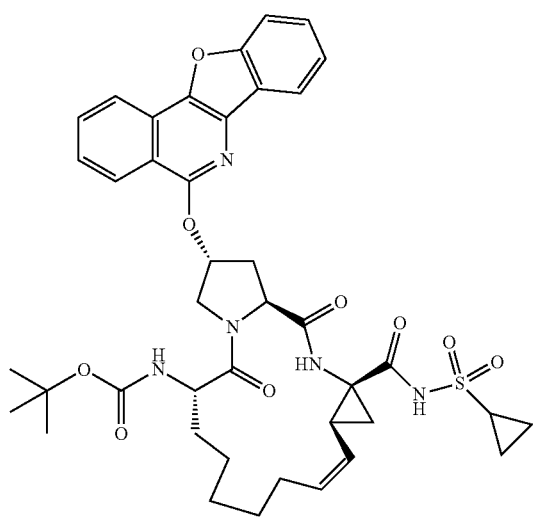
I6
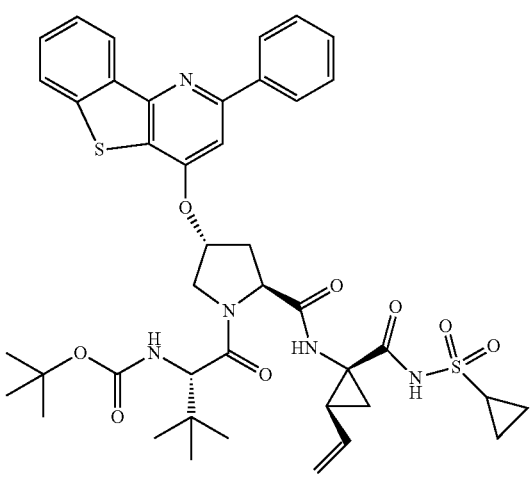
I9

I10
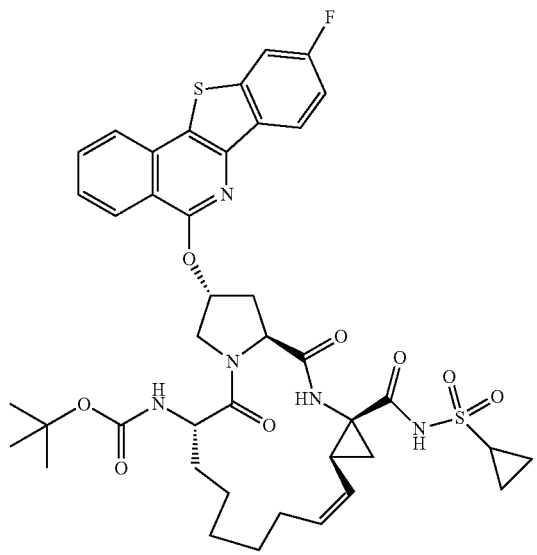
I11
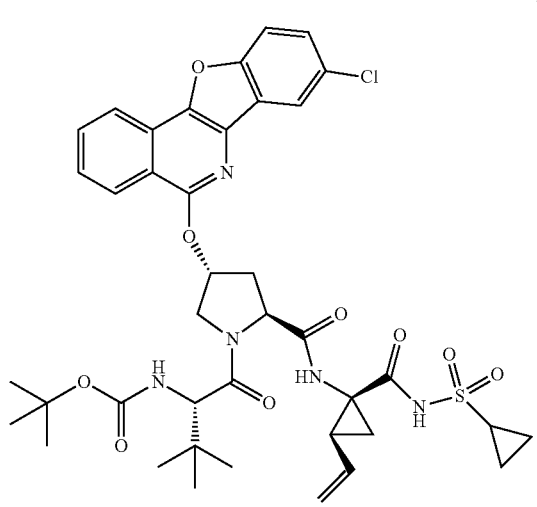
I12
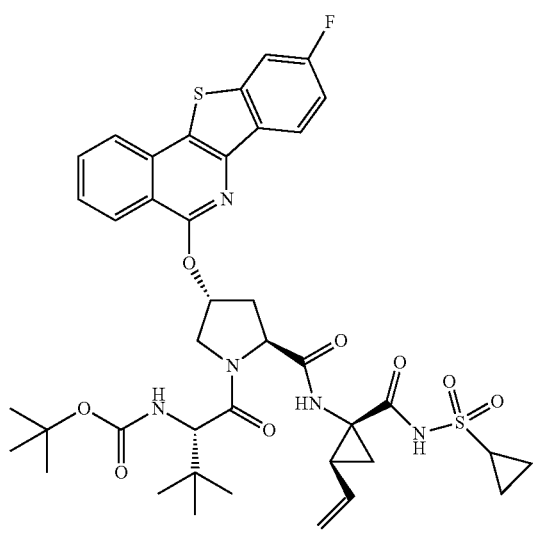
I13
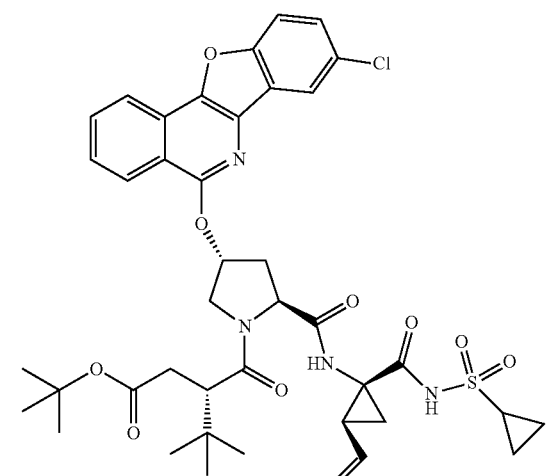
I14
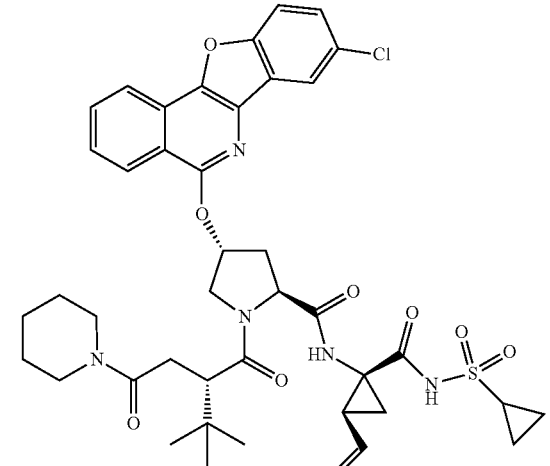
I15
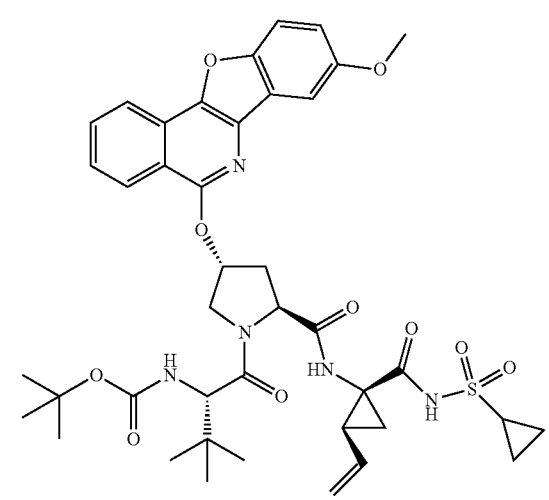

I16
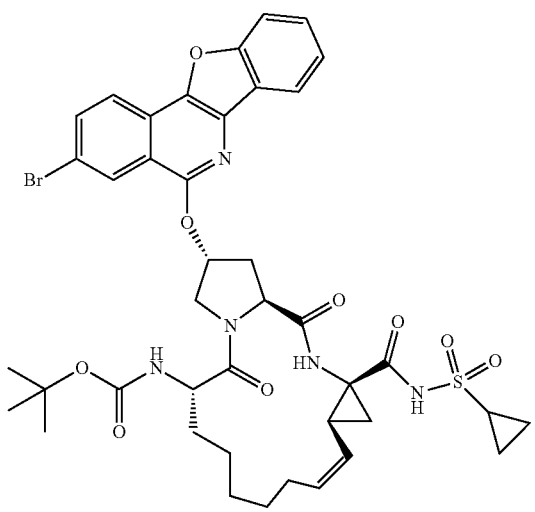
I17
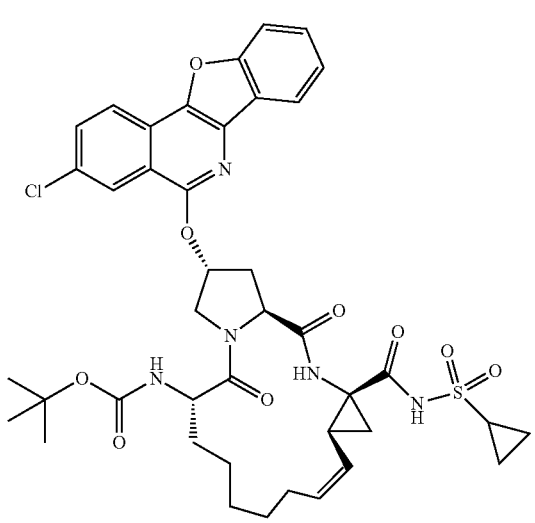
I18
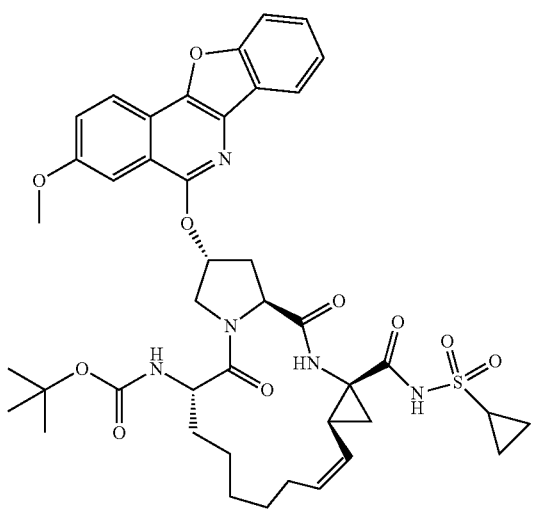
I19
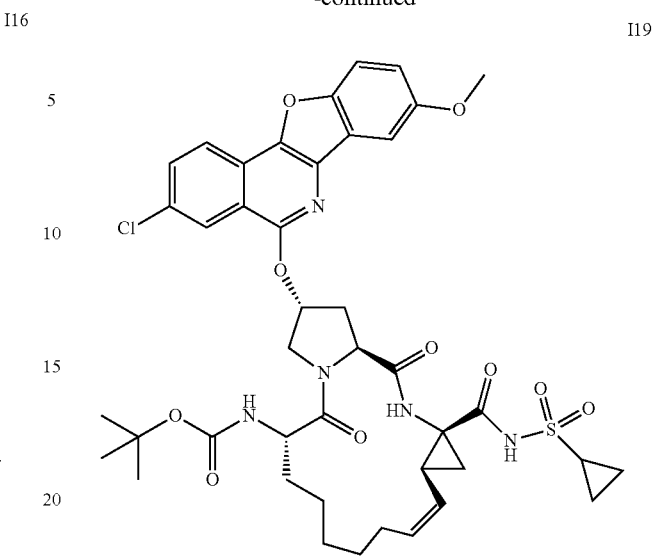
I20
I21

-continued
I22
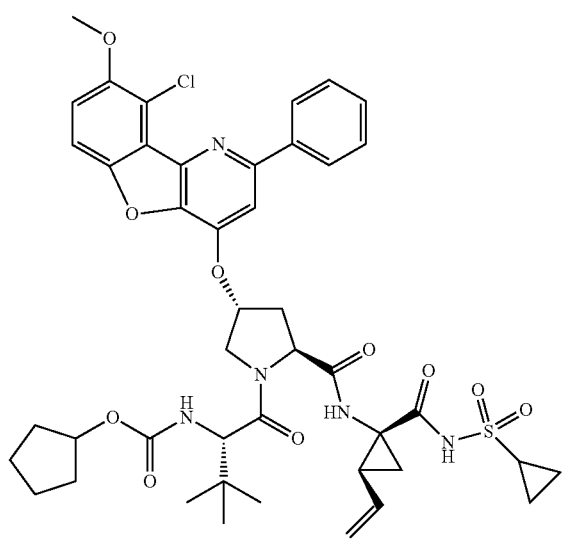
I23
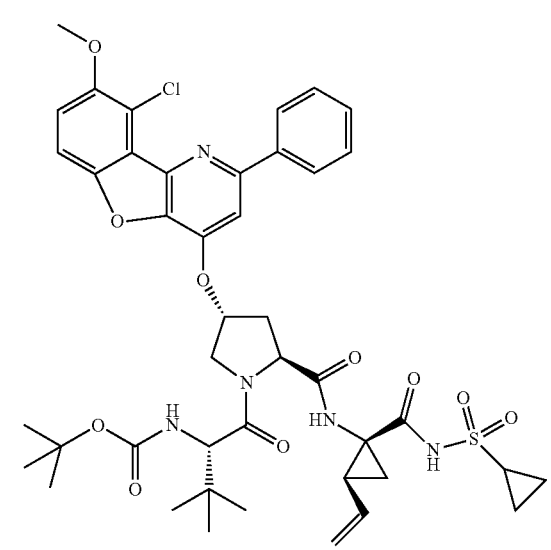
I24
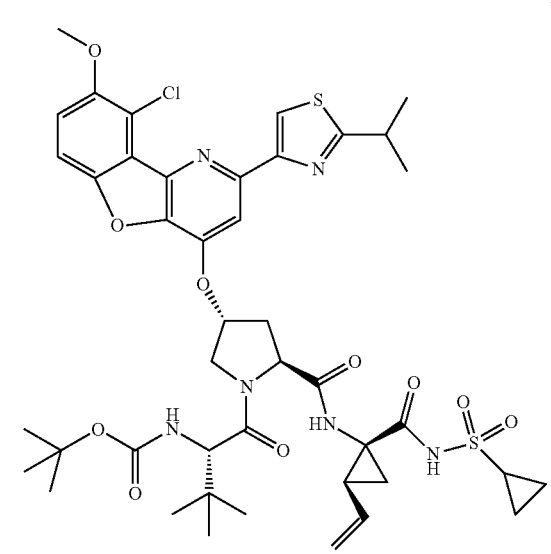
-continued
I25
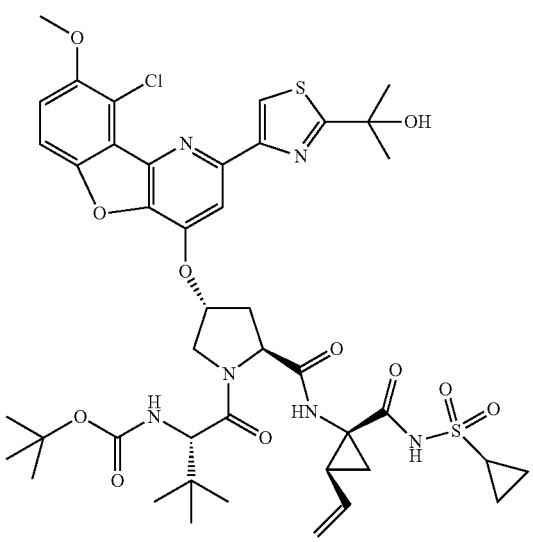
I26
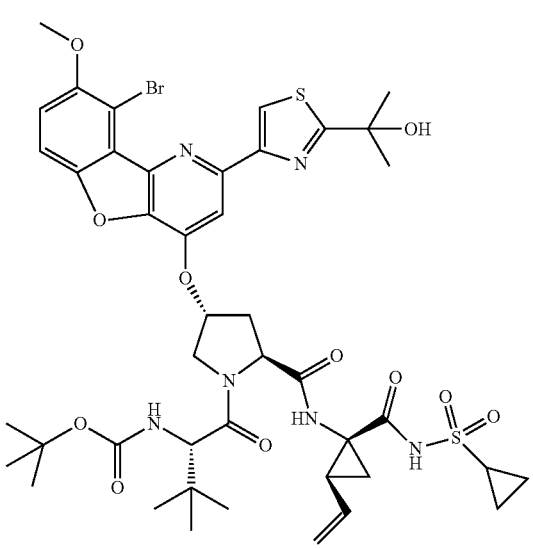
I27
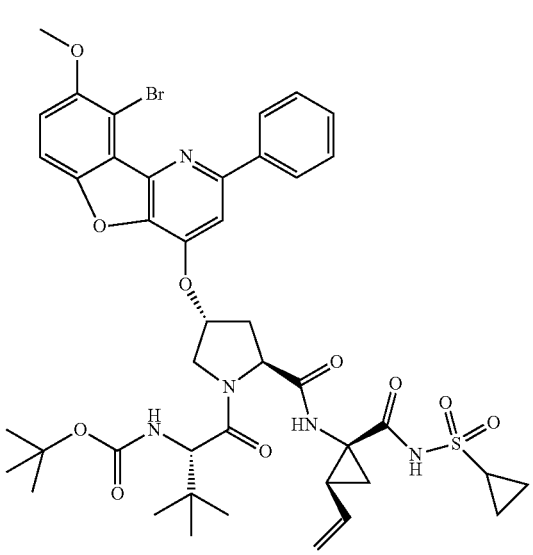

I28
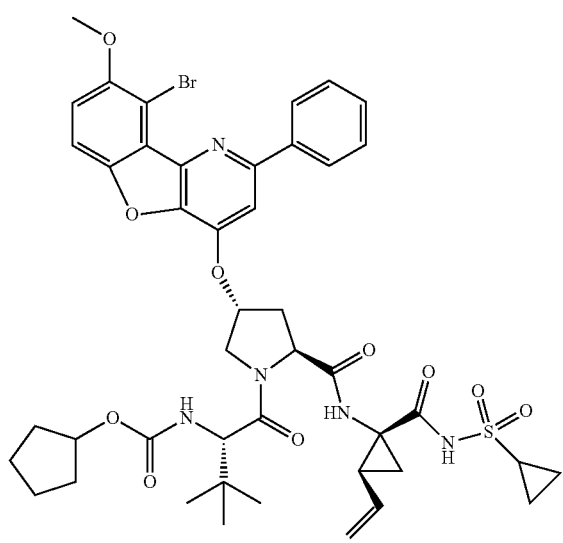
I31
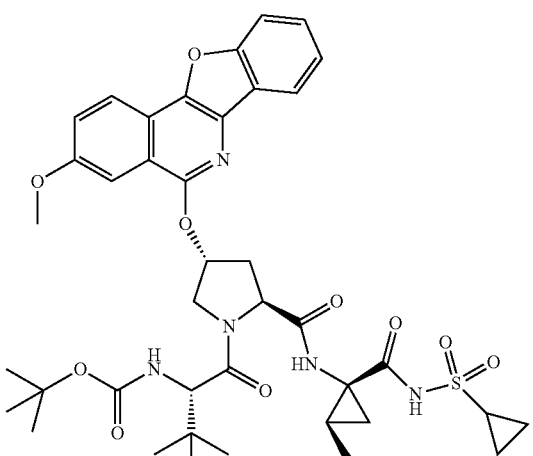
I29
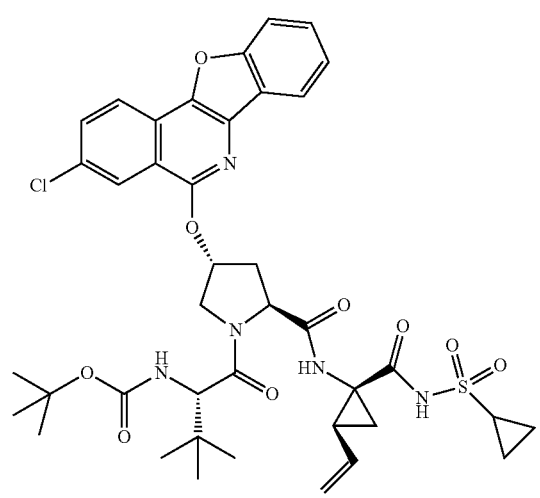
I32
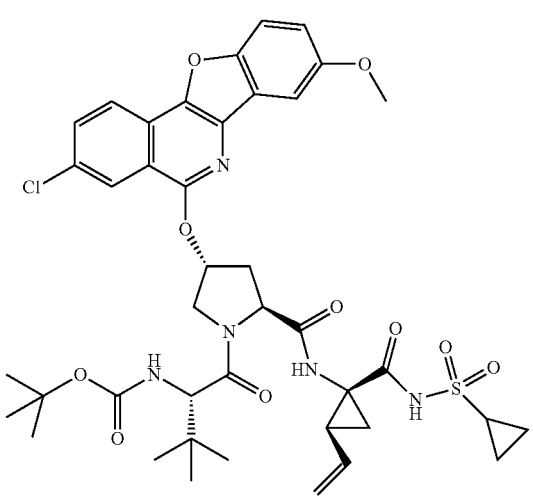
I30
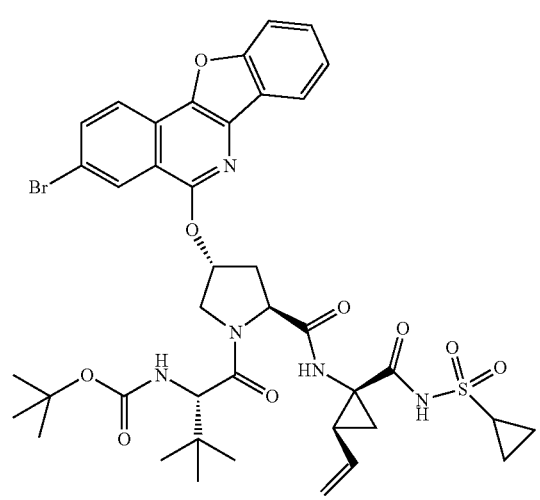
I33
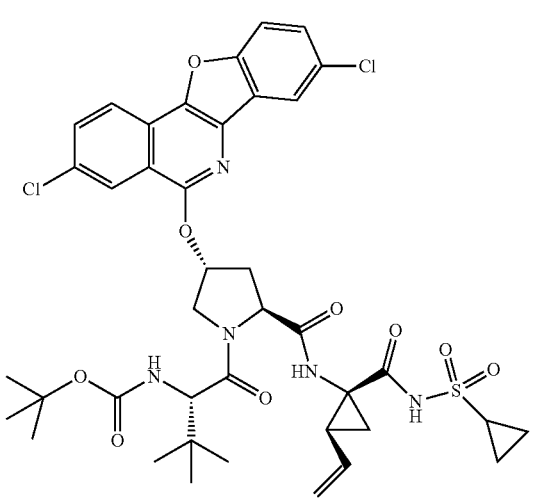

123
-continued
I34
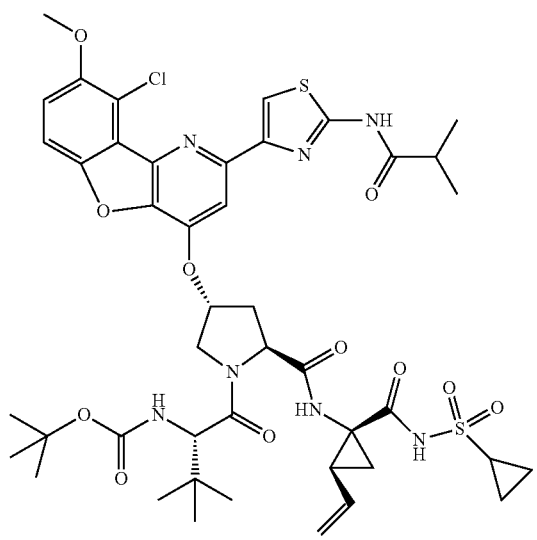
I35
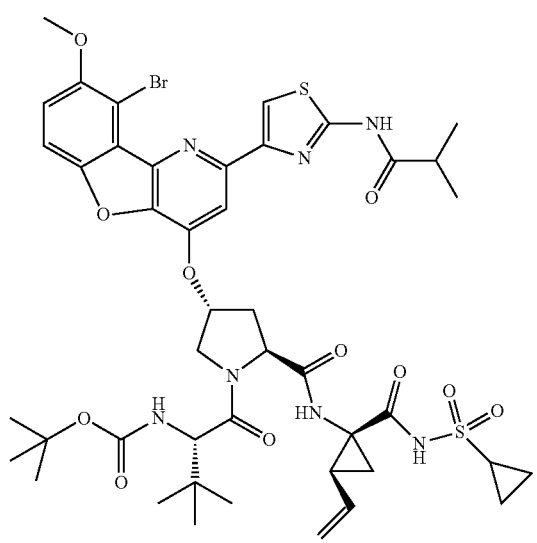
I36
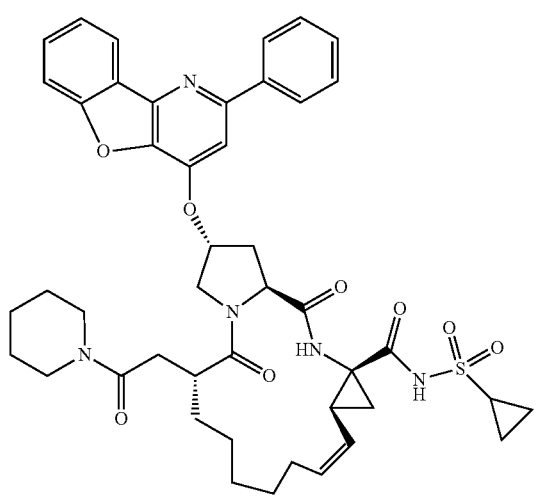
124
-continued
I37
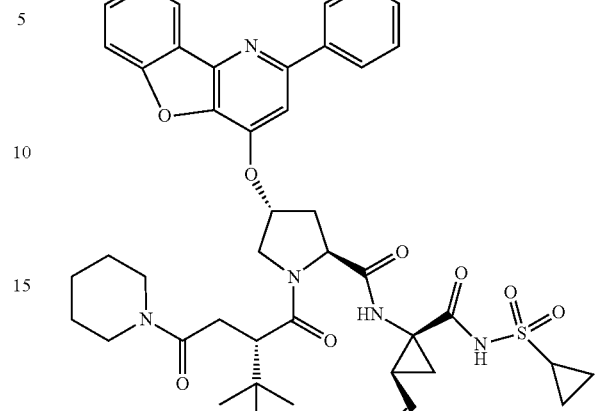
I38
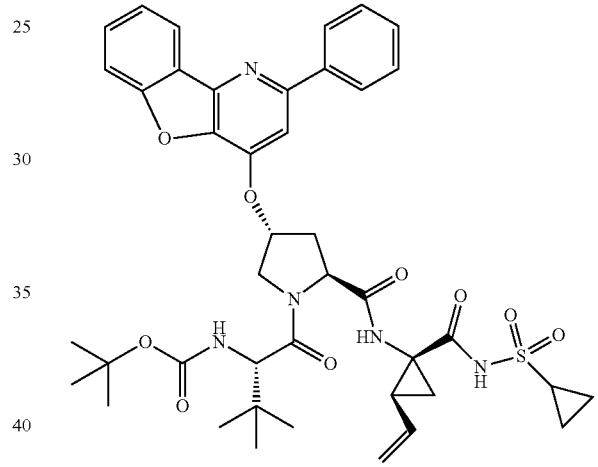
I39
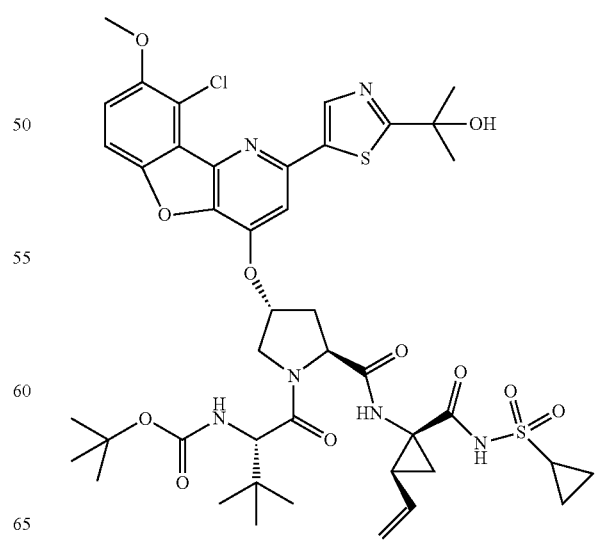

-continued

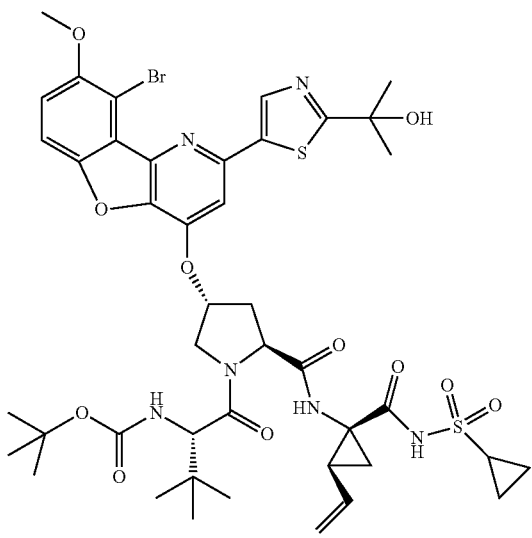

I40

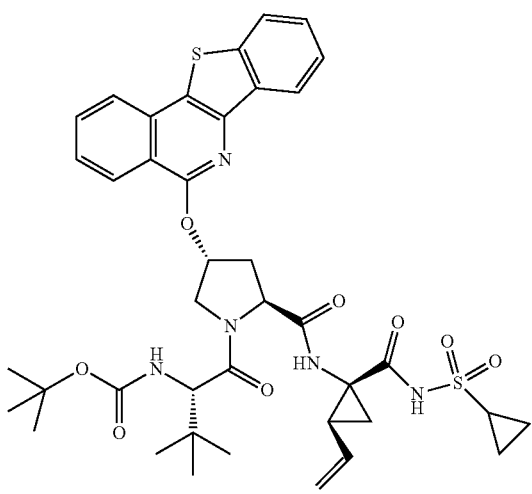

I41

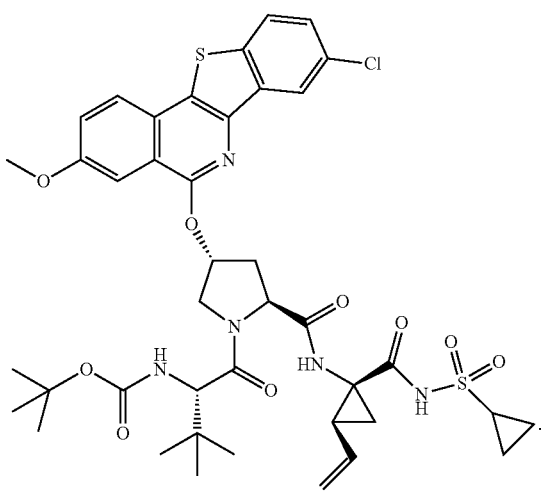

I42

13. The compound as claimed in claim 4, characterized in that Ar is a 6 membered aryl or a 5~6 membered heteroaryl which is substituted optionally by 1 or more $R_{Ar'}$; wherein, $R_{Ar'}$ is selected from the following substituent group: halogen, amino, $C_1$-$C_6$ alkyl, $C_1$-$C_6$ alkoxyl, $C_1$-$C_6$ hydroxyalkyl and ($C_1$-$C_6$) alkylamido.

14. The compound as claimed in claim 4, characterized in that $R'''$ is a substituent which can be substituted by 1~3 $R''''$ selected from the following group: $C_1$-$C_8$ alkyl, N≡C—($C_1$-$C_6$) alkyl, ($C_2$-$C_8$) alkenyl, ($C_2$-$C_8$) alkynyl, ($C_3$-$C_7$) cycloalkyl, ($C_3$-$C_7$ cycloalkyl) ($C_1$-$C_6$) alkyl, and 5~6 membered aryl or heteroaryl having 1-2 heteroatom(s) independently selected from N, O, S; $R''''$ is a substituent selected from the following group: halogen, ($C_1$-$C_6$) alkyl substituted optionally by ($C_1$-$C_6$)alkyl-O— or ($C_3$-$C_6$)cycloalkyl-O—, ($C_1$-$C_6$) haloalkyl, ($C_3$-$C_7$)cycloalkyl, ($C_1$-$C_6$)alkyl-O—, heteroaryl, —NH$_2$, ($C_1$-$C_4$ alkyl)NH— and ($C_1$-$C_4$ alkyl)$_2$N—.

15. The compound as claimed in claim 4, characterized in that $R_1'$ is a substituent which can be substituted by 1 or more $R_1''$ selected from the following group: $C_1$-$C_6$ alkyl, $C_2$-$C_6$ alkenyl, $C_2$-$C_6$ alkynyl, 6-8 membered aryl, (6-8 membered aryl) $C_1$-$C_2$ alkyl, $C_3$-$C_7$ cycloalkyl, ($C_3$-$C_7$ cycloalkyl) $C_1$-$C_2$ alkyl, $C_3$-$C_7$ cycloalkenyl, ($C_3$-$C_7$ cycloalkenyl) $C_1$-$C_2$ alkyl, 4-6 membered heterocycl having 1-3 heteroatoms selected from O, S, and N, (4-6 membered heterocycl having 1-3 heteroatoms selected from O, S and N) $C_1$-$C_2$ alkyl, $C_5$-$C_{10}$ heteroaryl and ($C_5$-$C_{10}$ heteroaryl) $C_1$-$C_2$ alkyl;

$R_1''$ is a substituent selected from the following group: halogen, OH, CN, $C_1$-$X_6$ alkyl, $C_2$-$C_6$ alkenyl, $C_2$-$C_6$ alkynyl, $C_1$-$C_6$ alkoxyl, —NH$_2$, ($C_1$-$C_6$ alkyl)—NH— and —N($C_1$-$C_6$ alkyl)$_2$.

16. The compound as claimed in claim 4, characterized in that $R_1'$ is

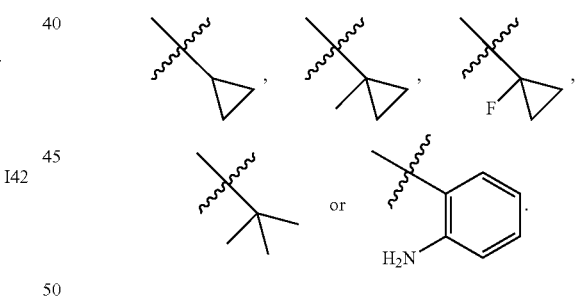

17. The compound as claimed in claim 4, characterized in that $R_1$ linking covalently with $R_3$ together forms a $C_5$ alkane chain.

18. The compound as claimed in claim 4, characterized in that $R_4$ is $C_1$-$C_{10}$ alkoxycarbonyl, ($C_1$-$C_{10}$ alkyl)—NHCO, ($C_1$-$C_{10}$ alkyl)$_2$NCO, 6-8 membered aryl, 5-8 membered heteroaryl having 1-3 heteroatoms selected from O, N and S or formyl substituted by 3~7 membered cycloalkyl, 4-6 membered heterocycl having 1-3 heteroatoms selected from O, S, and N or cycloalkoxy, which can be substituted by 1 or more $R_4'$;

$R_4'$ is a substituent selected from the following group: halogen, OH, CN, $C_1$-$C_6$ alkyl, $C_2$-$C_6$ alkenyl, $C_2$-$C_6$ alkynyl, $C_1$-$C_6$ alkoxyl, —NH$_2$, ($C_1$-$C_6$ alkyl)—NH— and —N($C_1$-$C_6$ alkyl)$_2$, ($C_1$-$C_6$ alkyl)—SO$_2$—.

19. The compound as claimed in claim 4, characterized in that $R_4$ is
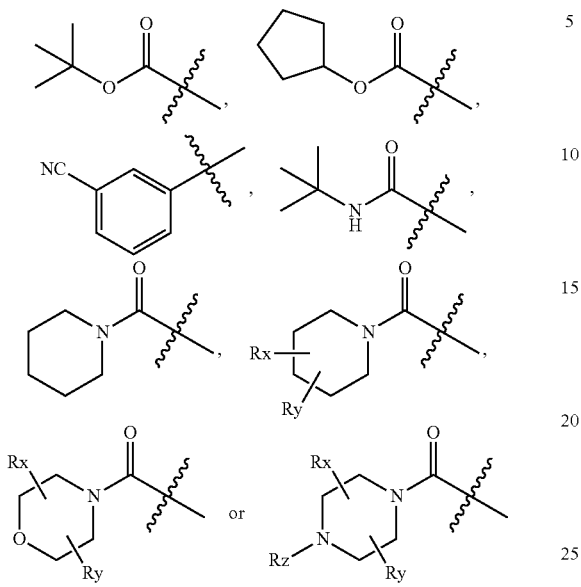
wherein, Rx and Ry independently is F, Cl, $C_1$-$C_6$ alkyl or $C_1$-$C_6$ alkoxyl, Rz is $C_1$-$C_6$ alkyl, $C_1$-$C_6$ alkoxyl, $C_1$-$C_6$ alkylformyl or ($C_1$-$C_6$ alkyl)—$SO_2$—.
* * * * *